US012564494B2

(12) United States Patent (10) Patent No.: US 12,564,494 B2
Dvorsky et al. (45) Date of Patent: Mar. 3, 2026

(54) VALVES AND DELIVERY APPARATUSES EQUIPPED WITH OPTIC FIBER SENSORS

(71) Applicant: Edwards Lifesciences Corporation, Irvine, CA (US)

(72) Inventors: Anatoly Dvorsky, Haifa (IL); Tamir S. Levi, Zikhron Yaakov (IL)

(73) Assignee: Edwards Lifesciences Corporation, Irvine, CA (US)

( * ) Notice: Subject to any disclaimer, the term of this patent is extended or adjusted under 35 U.S.C. 154(b) by 846 days.

(21) Appl. No.: 17/732,707

(22) Filed: Apr. 29, 2022

(65) Prior Publication Data

US 2022/0257379 A1 Aug. 18, 2022

Related U.S. Application Data

(63) Continuation of application No. PCT/US2020/057515, filed on Oct. 27, 2020.

(60) Provisional application No. 62/928,599, filed on Oct. 31, 2019.

(51) Int. Cl.
*A61F 2/24* (2006.01)

(52) U.S. Cl.
CPC ............ *A61F 2/2472* (2013.01); *A61F 2/243* (2013.01); *A61F 2250/0096* (2013.01)

(58) Field of Classification Search
CPC .................... A61F 2/2472; A61F 2/243; A61F 2250/0096; A61F 2/2466; A61F
2250/0002; A61F 2/2427; A61F
2002/9528; A61F 2002/9534; A61F
2250/001; A61F 2/2418; A61F 2/95
See application file for complete search history.

(56) References Cited

U.S. PATENT DOCUMENTS

| | | | |
|---|---|---|---|
| 9,504,392 B2 | 11/2016 | Caron et al. | |
| 2012/0041533 A1 | 2/2012 | Bertolino et al. | |
| 2014/0228943 A1 | 8/2014 | Stigall et al. | |
| 2014/0296962 A1 | 10/2014 | Cartledge et al. | |
| 2015/0209142 A1* | 7/2015 | Paul ..................... | A61F 2/2427 |
| | | | 623/2.11 |
| 2019/0142589 A1 | 5/2019 | Basude | |

FOREIGN PATENT DOCUMENTS

| | | | |
|---|---|---|---|
| WO | WO-2020092251 A1 | 5/2020 | |
| WO | WO-2021113431 A1 | 6/2021 | |
| WO | WO-2022081723 A1 | 4/2022 | |

* cited by examiner

*Primary Examiner* — Jerrah Edwards
*Assistant Examiner* — Jose H. Trevino, III
(74) *Attorney, Agent, or Firm* — Webb & Co.; Rosie H. Kim

(57) ABSTRACT

The present disclosure relates to devices and methods for measuring expansion diameter, radial force exerted against surrounding tissue, and pressure recovery across prosthetic heart valves, during valve implantation procedures.

16 Claims, 38 Drawing Sheets

VALVES AND DELIVERY APPARATUSES EQUIPPED WITH OPTIC FIBER SENSORS

CROSS REFERENCE TO RELATED APPLICATIONS

This application is a continuation of International Application No. PCT/US2020/057515, filed Oct. 27, 2020, which claims benefit of U.S. Provisional Application No. 62/928,599, filed on Oct. 31, 2019, the contents of each of which are herein incorporated by reference in their entirety.

FIELD

The present disclosure relates to devices and methods for measuring expansion diameter, radial force exerted against surrounding tissue, and pressure recovery across prosthetic heart valves, during valve implantation procedures.

BACKGROUND

Native heart valves, such as the aortic, pulmonary, and mitral valves, function to assure adequate directional flow from and to the heart, and between the heart's chambers, to supply blood to the whole cardiovascular system. Various valvular diseases can render the valves ineffective and require replacement with artificial valves. Surgical procedures can be performed to repair or replace a heart valve. Surgeries are prone to an abundance of clinical complications, hence alternative less invasive techniques of delivering a prosthetic heart valve over a catheter and implanting it over the native malfunctioning valve, have been developed over the years.

Mechanically expandable valves are a category of prosthetic valves that rely on a mechanical actuation mechanism for expansion. The actuation mechanism usually includes a plurality of actuation/locking assemblies, releasably connected to respective actuation members of the valve delivery system, controlled via a handle for actuating the assemblies to expand the valve to a desired diameter. The assemblies may optionally lock the valve's position to prevent undesired recompression thereof, and disconnection of the delivery system's actuation member from the valve actuation/locking assemblies, to enable retrieval thereof once the valve is properly positioned at the desired site of implantation.

Real-time feedback during the valve expansion procedure can provide the clinician with adequate data that may assist in decision making regarding different procedural considerations. Such data can include the force exerted by the expanded valve on the surrounding anatomy, and the hemodynamic parameters in the immediate vicinity of the valve. Accordingly, a need exists for improvements in devices, systems and methods for accurately measuring parameters associated with pressure recovery across the prosthetic valve, real-time expansion diameter, and other physiologic parameters to ensure proper prosthetic valve functionality.

SUMMARY

The present disclosure is directed toward devices and assemblies equipped with optic fiber sensors for monitoring parameters during prosthetic valve implantation procedures. The devices and assemblies are primarily intended to monitor in real-time at least one of: a pressure within, or in the vicinity of, a prosthetic valve, pressure drop across the prosthetic valve, expansion diameter of the prosthetic valve and/or radial force of the prosthetic valve. The real-time measurements provided by the optic fibers can be used with a delivery assembly to ensure proper implantation of a prosthetic valve within a designated site of implantation, such as the site of malfunctioning native valve.

According to one aspect, there is provided a delivery assembly comprising a prosthetic valve, a delivery apparatus and at least one optic fiber assembly. The prosthetic valve is radially expandable and compressible between a radially compressed state and a radially expanded state. The prosthetic valve comprises an outflow end portion, an inflow end portion, and at least one actuator assembly. Each actuator assembly comprises an outer member and an inner member. The outer member is defined between an outer member proximal end and an outer member distal end, and is secured to a first location of the valve. The outer member is secured to a second location of the valve, axially spaced from the first location. The prosthetic valve is expandable from the radially compressed state to the radially expanded state upon actuating the at least one actuator assembly to approximate the second location to the first location.

The delivery apparatus comprises a handle and at least one actuation arm assembly extending from the handle. The at least one actuation arm assembly comprises an actuation member and a support sleeve. The actuation member is releasably coupled to the inner member. The support sleeve surrounds the actuation member. The prosthetic valve is releasable from the delivery apparatus by decoupling each of the at least one actuation arm assemblies from each corresponding actuator assembly.

The at least one optic fiber assembly comprises a first optic fiber section, a second optic fiber section, and an interface between the first optic fiber section and the second optic fiber section. The first optic fiber section is connected to the delivery apparatus, and comprises at least one first optic core. The second optic fiber section is connected to the prosthetic valve, and comprises at least one second optic core. The interface is configured to provide detachable optical coupling between the first optic fiber section and the second optic fiber section. The second optic fiber section is configured to be decoupled from the first optic fiber section, upon releasing the prosthetic valve from the delivery apparatus.

According to some embodiments, the at least one second optic fiber section comprises a plurality of axially spaced Fiber Bragg Gratings disposed along at least a portion of its second optic core.

According to some embodiments, the second optic fiber section comprises at least one pressure sensing head.

According to some embodiments, the at least one pressure sensing head of the second optic fiber section is an axial pressure sensing head. The axial pressure sensing head comprises a front diaphragm, and a front cavity between the at least one second optic core and the front diaphragm. Both of the front diaphragm and the front cavity are coaxially aligned with the at least one second optic core.

According to some embodiments, the at least one pressure sensing head of the second optic fiber section is a lateral pressure sensing head, and the at least one second optic core comprises an inclined distal core surface. The lateral pressure sensing head of the second optic fiber section comprises a side diaphragm, and a side cavity between the inclined distal core surface and the side diaphragm. Both of the side diaphragm and the side cavity are cross-axially aligned with the at least one second optic core.

According to some embodiments, the at least one optic fiber assembly is a multi-core optic fiber assembly, comprising a plurality of axially spaced pressure sensing heads.

In such embodiments, the first optic fiber section comprises a plurality of first optic cores.

According to some embodiments, the second optic fiber section comprises a plurality of cores and a plurality of axially spaced pressure sensing heads, wherein at least one of the plurality of pressure sensing heads is positioned in the outflow end portion of the prosthetic valve, and wherein at least another one of the plurality of pressure sensing heads is positioned in the inflow end portion of the prosthetic valve.

According to some embodiments, the first optic fiber section comprises at least two cores and at least one pressure sensing head, wherein the second optic fiber section comprises at least one pressure sensor head.

According to some embodiments, the at least one lateral pressure sensing head of the second optic fiber section is a contact-force sensing head, further comprising a lateral extension.

According to some embodiments, at least two optic fiber assemblies are attached to the same actuator assembly, wherein each optic fiber assembly comprises a lateral pressure sensing head, such that the at least two lateral pressure sensing heads are oriented at diametrically opposing radial directions.

According to some embodiments, the at least one optic fiber assembly is a multi-core optic fiber assembly, which comprises at least two lateral pressure sensing heads, both of which are attached to the same actuator assembly, and oriented at diametrically opposing radial directions.

According to some embodiments, the actuation member comprises an actuation member channel, wherein at least a portion of the at least one first optic fiber section extends through the actuation member channel.

According to some embodiments, the difference between the inner diameter of the actuation member channel and the outer diameter of the first fiber section is not greater than 30% of the diameter of the first optic.

According to some embodiments, the difference between the inner diameter of the actuation member channel and the outer diameter of the first fiber section is not greater than 20% of the diameter of the first optic core.

According to some embodiments, the difference between the inner diameter of the actuation member channel and the outer diameter of the first fiber section is not greater than 10% of the diameter of the first optic core.

According to some embodiments, the inner member comprises an inner member channel, and at least a portion of the at least one second optic fiber section extends through the inner member channel.

According to some embodiments, the difference between the inner diameter of the inner member channel and the outer diameter of the second fiber section is not greater than 30% of the diameter of the second optic core.

According to some embodiments, the difference between the inner diameter of the inner member channel and the outer diameter of the second fiber section is not greater than 20% of the diameter of the second optic core.

According to some embodiments, the difference between the inner diameter of the inner member channel and the outer diameter of the second fiber section is not greater than 10% of the diameter of the second optic core.

According to some embodiments, the interface comprises a physical contact connection between the first optic fiber section and the second optic fiber section.

According to some embodiments, the interface is located at the level of or distal to the outer member proximal end.

According to some embodiments, the first optic fiber section is connected to the handle.

According to some embodiments, the delivery assembly further comprises at least one continuous optic fiber connected to the delivery apparatus. The at least one continuous optic fiber comprises at least one continuous optic core and at least one pressure sensing head.

According to some embodiments, the at least one continuous optic fiber is a multi-core continuous optic fiber, and comprises a plurality of continuous optic cores and a plurality of axially spaced pressure sensing heads.

According to some embodiments, the at least one pressure sensing head of the continuous optic fiber is an axial pressure sensing head. The axial pressure sensing head of the continuous optic fiber comprises a front diaphragm, and a front cavity between the at least one continuous optic core and the front diaphragm, wherein both of the front diaphragm and the front cavity are coaxially aligned with the at least one continuous optic core.

According to some embodiments, the at least one continuous optic core comprises an inclined distal continuous core surface, wherein the at least one pressure sensing head of the continuous optic fiber is a lateral pressure sensing head. The lateral pressure sensing head of the continuous optic fiber comprises a side diaphragm, and a side cavity between the inclined distal core surface and the side diaphragm, such that the side diaphragm and the side cavity are cross-axially aligned with the at least one continuous optic core.

According to some embodiments, the at least one continuous optic fiber is attached to an outer surface of the support sleeve.

According to some embodiments, the at least one continuous optic fiber is attached to the handle.

According to some embodiments, the outer diameter of the first optic fiber section is equal to the diameter of the second optic fiber section.

According to some embodiments, the at least one continuous optic fiber is attached to the actuation arm assembly.

According to some embodiments, the outer diameter of the first optic core is equal to the outer diameter of the second optic core.

According to some embodiments, the at least one optic fiber assembly comprises a plurality optic fiber assemblies, positioned such that the respective pressure sensing heads are circumferentially distanced from each other around the prosthetic valve.

According to some embodiments, the pressure sensing heads are positioned at the outflow end portion.

According to another aspect, there is provided a delivery assembly, comprising a prosthetic valve, a delivery apparatus and at least one continuous optic fiber. The prosthetic valve radially expandable and compressible between a radially compressed state and a radially expanded state. The prosthetic valve comprises an outflow end portion, an inflow end portion, and at least one actuator assembly. Each actuator assembly comprises an outer member and an inner member. The outer member is defined between an outer member proximal end and an outer member distal end, and is secured to a first location of the valve. The outer member is secured to a second location of the valve, axially spaced from the first location. The prosthetic valve is expandable from the radially compressed state to the radially expanded state upon actuating the at least one actuator assembly to approximate the second location to the first location.

The delivery apparatus comprises a handle and at least one actuation arm assembly extending from the handle. The at least one actuation arm assembly comprises an actuation member and a support sleeve. The actuation member is releasably coupled to the inner member. The support sleeve surrounds the actuation member. The prosthetic valve is releasable from the delivery apparatus by decoupling each of the at least one actuation arm assemblies from each corresponding actuator assembly.

The at least one continuous optic fiber attached to the delivery apparatus, and comprises at least one continuous optic core and at least one pressure sensing head. The at least one pressure sensing head of the continuous optic fiber comprises a diaphragm and an optical cavity between the at least one continuous optic core and the diaphragm. Each pressure sensing head of the continuous optic fiber is positioned proximal to the outflow end portion of the prosthetic valve.

According to some embodiments, the at least one continuous optic fiber is attached to the actuation arm assembly.

According to some embodiments, the at least one continuous optic fiber is attached to an outer surface of the support sleeve.

According to some embodiments, the at least one continuous optic fiber comprises a plurality of continuous optic fibers, attached to the delivery apparatus such that the corresponding plurality of pressure sensing heads are axially spaced from each other.

According to some embodiments, the at least one continuous optic fiber is a multi-core continuous optic fiber, which comprises a plurality of continuous optic cores and a plurality of axially spaced pressure sensing heads.

According to some embodiments, the at least one pressure sensing head of the continuous optic fiber is an axial pressure sensing head. The axial pressure sensing head of the continuous optic fiber comprises a front diaphragm, and a front cavity between the at least one continuous optic core and the front diaphragm, wherein both of the front diaphragm and the front cavity are coaxially aligned with the at least one continuous optic core.

According to some embodiments, the at least one continuous optic core comprises an inclined distal continuous core surface, and the at least one pressure sensing head of the continuous optic fiber is a lateral pressure sensing head. The lateral pressure sensing head of the continuous optic fiber comprises a side diaphragm, and a side cavity between the inclined distal core surface and the side diaphragm, wherein both of the side diaphragm and the side cavity are cross-axially aligned with the at least one continuous optic core.

According to some embodiments, the at least one continuous optic fiber is attached to the handle.

According to some embodiments, the at least one continuous optic fiber assembly comprises a plurality continuous optic fiber assemblies, positioned such that the respective pressure sensing heads are circumferentially distanced from each other around the prosthetic valve.

According to some embodiments, the pressure sensing heads are positioned at the outflow end portion.

Certain embodiments described herein may include some, all, or none of the above advantages. Further advantages may be readily apparent to those skilled in the art from the figures, descriptions, and claims included herein. Aspects and embodiments are further described in the specification herein below and in the appended claims.

Unless otherwise defined, all technical and scientific terms used herein have the same meaning as commonly understood by one of ordinary skill in the art. In case of conflict, the patent specification, including definitions, governs. As used herein, the indefinite articles "a" and "an" mean "at least one" or "one or more" unless the context clearly dictates otherwise.

The following embodiments and aspects thereof are described and illustrated in conjunction with systems, tools and methods which are meant to be exemplary and illustrative, but not limiting in scope. In various embodiments, one or more of the above-described problems have been reduced or eliminated, while other embodiments are directed to other advantages or improvements.

BRIEF DESCRIPTION OF THE FIGURES

Some embodiments are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the embodiments described herein. For the sake of clarity, some objects depicted in the figures are not to scale.

In the Figures.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. In order to avoid undue clutter from having too many reference numbers and lead lines on a particular drawing, some components will be introduced via one or more drawings and not explicitly identified in every subsequent drawing that contains that component.

Figure 1:
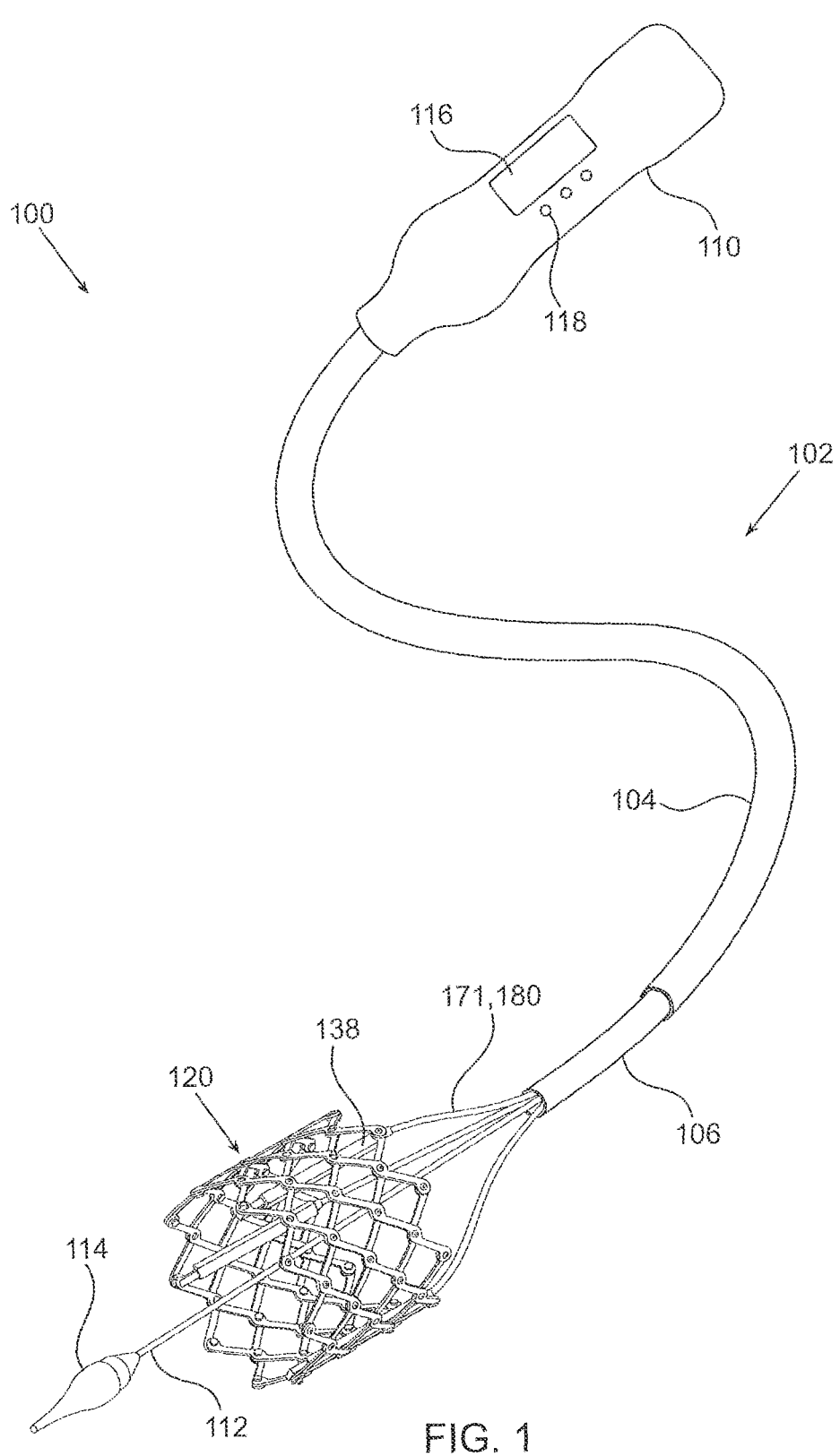
FIG. 1 constitutes a view in perspective of a delivery assembly comprising a delivery apparatus carrying a prosthetic valve, according to some embodiments.

FIG. 1 constitutes a view in perspective of a delivery assembly 100, according to some embodiments. The delivery assembly 100 can include a prosthetic valve 120 and a delivery apparatus 102. The prosthetic valve 120 can be on or releasably coupled to the delivery apparatus 102. The delivery apparatus can include a handle 110 at a proximal end thereof, a nose cone shaft 112 extending distally from the handle 110, a nose cone 114 attached to the distal end of the nosecone shaft 112, a delivery shaft 106 extending over the nose cone shaft 112, and optionally an outer shaft 104 extending over the delivery shaft 106.

The term "proximal", as used herein, generally refers to the side or end of any device or a component of a device, which is closer to the handle 110 or an operator of the handle 110 when in use.

The term "distal", as used herein, generally refers to the side or end of any device or a component of a device, which is farther from the handle 110 or an operator of the handle 110 when in use.

The term "prosthetic valve", as used herein, refers to any type of a prosthetic valve deliverable to a patient's target site over a catheter, which is radially expandable and compressible between a radially compressed, or crimped, state, and a radially expanded state. Thus, a prosthetic valve 120 can be crimped or retained by a delivery apparatus 102 in a compressed state during delivery, and then expanded to the expanded state once the prosthetic valve 120 reaches the implantation site. The expanded state may include a range of diameters to which the valve may expand, between the compressed state and a maximal diameter reached at a fully expanded state. Thus, a plurality of partially expanded states may relate to any expansion diameter between radially compressed or crimped state, and maximally expanded state.

The term "plurality", as used herein, means more than one.

A prosthetic valve 120 of the current disclosure may include any prosthetic valve configured to be mounted within the native aortic valve, the native mitral valve, the native pulmonary valve, and the native tricuspid valve. While a delivery assembly 100 described in the current disclosure, includes a delivery apparatus 102 and a prosthetic valve 120, it should be understood that the delivery apparatus 102 according to any embodiment of the current disclosure can be used for implantation of other prosthetic devices aside from prosthetic valves, such as stents or grafts.

According to some embodiments, the prosthetic valve 120 is a mechanically expandable valve, and the delivery apparatus 102 further comprises a plurality of actuation arm assemblies extending from the handle 110 through the delivery shaft 106. The actuation arm assemblies 171 can generally include actuation members 172 (hidden from view in FIG. 1, visible in FIGS. 4A-4C) releasably coupled at their distal ends to respective actuator assemblies 138 of the valve 120, and support sleeves 180 (annotated in FIG. 3) disposed around the respective actuation members 172. Each actuation member 172 may be axially movable relative to the support sleeve 180 covering it.

The prosthetic valve 120 can be delivered to the site of implantation via a delivery assembly 100 carrying the valve 120 in a radially compressed or crimped state, toward the target site, to be mounted against the native anatomy, by expanding the valve 120 via a mechanical expansion mechanism, as will be elaborated below.

The delivery assembly 100 can be utilized, for example, to deliver a prosthetic aortic valve for mounting against the aortic annulus, to deliver a prosthetic mitral valve for mounting against the mitral annulus, or to deliver a prosthetic valve for mounting against any other native annulus.

The nosecone 114 can be connected to the distal end of the nosecone shaft 112. A guidewire (not shown) can extend through a central lumen of the nosecone shaft 112 and an inner lumen of the nosecone 114, so that the delivery apparatus 102 can be advanced over the guidewire through the patient's vasculature.

A distal end portion of the outer shaft 104 can extend over the prosthetic valve 120 and contact the nosecone 114 in a delivery configuration of the delivery apparatus 102. Thus, the distal end portion of the outer shaft 104 can serve as a delivery capsule that contains, or houses, the prosthetic valve 120 in a radially compressed or crimped configuration for delivery through the patient's vasculature.

The outer shaft 104 and the delivery shaft 106 can be configured to be axially movable relative to each other, such that a proximally oriented movement of the outer shaft 104 relative to the delivery shaft 106, or a distally oriented movement of the delivery shaft 106 relative to the outer shaft 104, can expose the prosthetic valve from the outer shaft 104. In alternative embodiments, the prosthetic valve 120 is not housed within the outer shaft 104 during delivery. Thus, according to some embodiments, the delivery apparatus 102 does not include an outer shaft 104.

As mentioned above, the proximal ends of the nose cone shaft 112, the delivery shaft 106, components of the actuation arm assemblies 171, and when present—the outer shaft 104, can be coupled to the handle 110. During delivery of the prosthetic valve 120, the handle 110 can be maneuvered by an operator (for example, a clinician or a surgeon) to axially advance or retract components of the delivery apparatus 102, such as the nosecone shaft 112, the delivery shaft 106, and/or the outer shaft 104, through the patient's vasculature, as well as to expand or contract the prosthetic valve 120, for example by maneuvering the actuation arm assemblies 171, and to disconnect the prosthetic valve 120 from the delivery apparatus 102, for example—by decoupling the actuation members 172 from the actuator assemblies 138 of the valve 120, in order to retract it once the prosthetic valve is mounted in the implantation site.

The term "and/or" is inclusive here, meaning "and" as well as "or". For example, "delivery shaft 106 and/or outer shaft 104" encompasses, delivery shaft 106, outer shaft 104, and delivery shaft 106 with outer shaft 104; and, such "delivery shaft 106 and/or outer shaft 104" may include other elements as well.

According to some embodiments, the handle 110 can include one or more operating interfaces, such as steerable or rotatable adjustment knobs, levers, buttons (not shown) and other actuating mechanisms, which are operatively connected to different components of the delivery apparatus 102 and configured to produce axial movement of the delivery apparatus 102 in the proximal and distal directions, as well as to expand or contract the prosthetic valve 120 via various adjustment and activation mechanisms as will be further described below.

According to some embodiments, the handle further comprises one or more visual or auditory informative elements configured to provide visual or auditory information and/or feedback to a user or operator of the delivery apparatus 102, such as a display 116, led lights 118, speakers (not shown) and the like.

Figures 2, 3A, 3B:
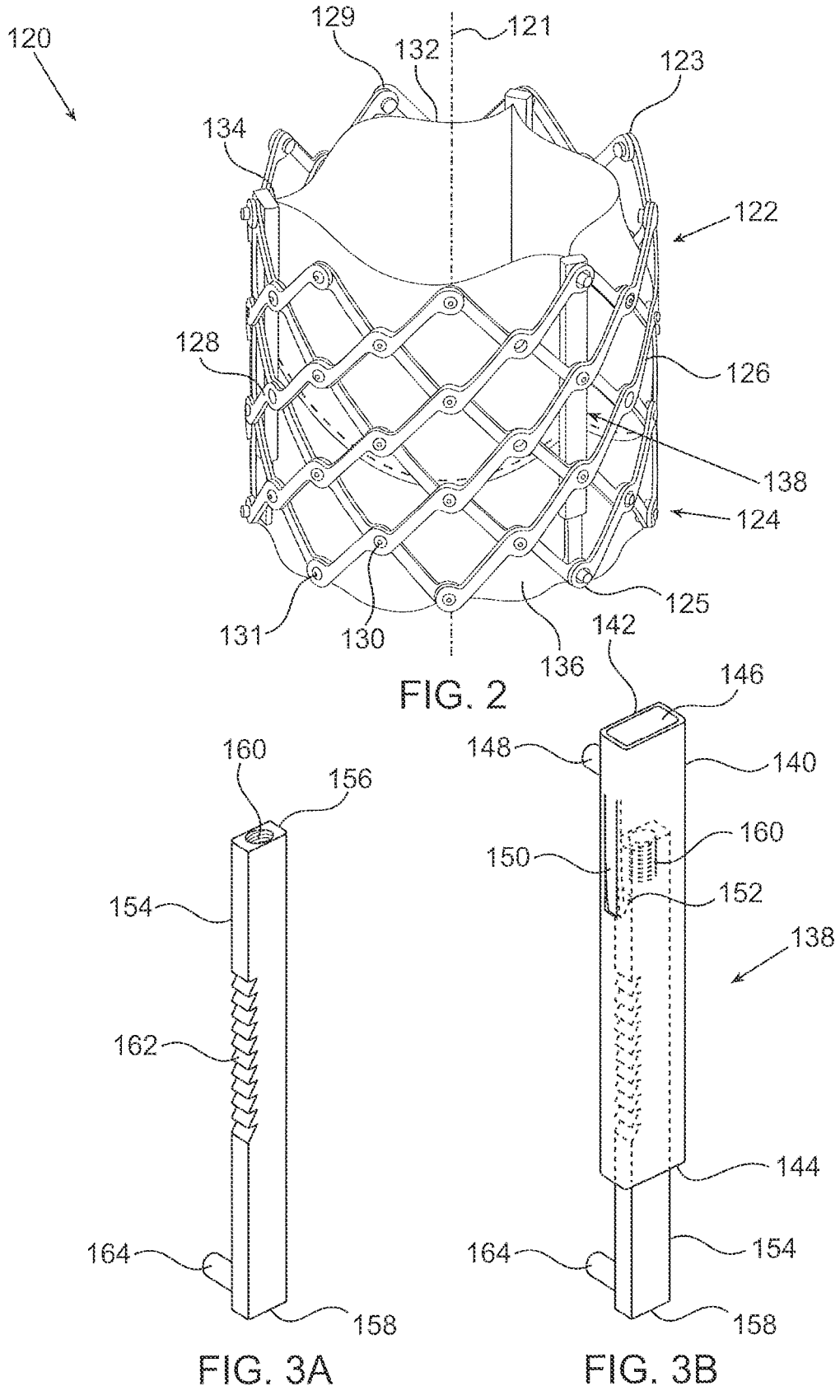
FIG. 2 constitutes a view in perspective of a prosthetic valve, according to some embodiments.
FIG. 3A constitutes a view in perspective of an inner member, according to some embodiments.
FIG. 3B constitutes a view in perspective of an actuator assembly, according to some embodiments.

FIG. 2 shows an exemplary mechanically expandable prosthetic valve 120 in an expanded state, according to some embodiments. The prosthetic valve 120 can comprise an inflow end portion 124 defining an inflow end 125, and an outflow end portion 122 defining an outflow end 123. The prosthetic valve 120 can define a longitudinal axis 121 extending through the inflow end portion 124 and the outflow end portion 122. In some instances, the outflow end 123 is the distal end of the prosthetic valve 120, and the inflow end 125 is the proximal end of the prosthetic valve 120. Alternatively, depending for example on the delivery approach of the valve, the outflow end can be the proximal end of the prosthetic valve, and the inflow end can be the distal end of the prosthetic valve.

The term "outflow", as used herein, refers to a region of the prosthetic valve through which the blood flows through and out of the valve 120, for example between the longitudinal center of the valve and the outflow end 123.

The term "inflow", as used herein, refers to a region of the prosthetic valve through which the blood flows into the valve 120, for example between inflow end 125 and the longitudinal center of the valve.

The valve 120 comprises a frame 126 composed of interconnected struts 128, and may be made of various suitable materials, such as stainless steel, cobalt-chrome alloy (for example, MP35N alloy), or nickel titanium alloy such as Nitinol. According to some embodiments, the struts 128 are arranged in a lattice-type pattern. In the embodiment illustrated in FIG. 2, the struts 128 are positioned diagonally, or offset at an angle relative to, and radially offset from, the longitudinal axis 121 when the valve is in an expanded position. It will be clear that the struts 128 can be offset by other angles than those shown in FIG. 2, such as being oriented substantially parallel to the longitudinal axis 121.

According to some embodiments, the struts 128 are pivotably coupled to each other. In the exemplary embodiment shown in FIG. 2, the end portions of the struts 128 are forming apices 129 at the outflow end 123 and apices 131 at the inflow end 125. The struts 128 can be coupled to each other at additional junctions 130 formed between the outflow apices 129 and the inflow apices 131. The junctions 130 can be equally spaced apart from each other, and/or from the apices 129, 131 along the length of each strut 128. Frame 126 may comprise openings or apertures at the regions of apices 129, 131 and junctions 130 of the struts 128. Respective hinges can be included at locations where the apertures of struts 128 overlap each other, via fasteners, such as rivets or pins, which extend through the apertures. The hinges can allow the struts 128 to pivot relative to one another as the frame 126 is radially expanded or compressed.

In alternative embodiments, the struts are not coupled to each other via respective hinges, but are otherwise pivotable or bendable relative to each other, so as to permit frame expansion or compression. For example, the frame can be formed from a single piece of material, such as a metal tube, via various processes such as, but not limited to, laser cutting, electroforming, and/or physical vapor deposition, while retaining the ability to collapse/expand radially in the absence of hinges and like.

A prosthetic valve 120 further comprises one or more leaflets 132, e.g., three leaflets, configured to regulate blood flow through the prosthetic valve 120 from the inflow end to the outflow end. While three leaflets 132 arranged to collapse in a tricuspid arrangement, are shown in the exemplary embodiment illustrated in FIG. 2, it will be clear that a prosthetic valve 120 can include any other number of leaflets 132. The leaflets 132 are made of a flexible material, derived from biological materials (for example, bovine pericardium or pericardium from other sources), bio-compatible synthetic materials, or other suitable materials. The leaflets may be coupled to the frame 126 via commissures 134, either directly or attached to other structural elements connected to the frame 126 or embedded therein, such as commissure posts. Further details regarding prosthetic valves, including the manner in which leaflets may be mounted to their frames, are described in U.S. Pat. Nos. 6,730,118, 7,393, 360, 7,510,575, 7,993,394 and 8,252,202, and U.S. Patent Application No. 62/614,299, all of which are incorporated herein by reference.

According to some embodiments, the prosthetic valve 120 may further comprise at least one skirt or sealing member, such as the inner skirt 136 shown in the exemplary embodiment illustrated in FIG. 2. The inner skirt 136 can be mounted on the inner surface of the frame 126, configured to function, for example, as a sealing member to prevent or decrease perivalvular leakage. The inner skirt 136 can further function as an anchoring region for the leaflets 132 to the frame 126, and/or function to protect the leaflets 132 against damage which may be caused by contact with the frame 126, for example during valve crimping or during working cycles of the prosthetic valve 120. Additionally, or alternatively, the prosthetic valve 120 can comprise an outer skirt (not shown) mounted on the outer surface of the frame 126, configure to function, for example, as a sealing member retained between the frame 126 and the surrounding tissue of the native annulus against which the prosthetic valve 120 is mounted, thereby reducing risk of paravalvular leakage past the prosthetic valve 120. Any of the inner skirt 136 and/or outer skirt can be made of various suitable biocompatible materials, such as, but not limited to, various synthetic materials (for example, PET) or natural tissue (for example pericardial tissue).

According to some embodiments, a prosthetic valve 120, which can be a mechanical prosthetic valve, comprises a plurality of actuator assemblies 138, configured to facilitate expansion of the valve 120, and in some instances, to lock the valve at an expanded state, preventing unintentional recompression thereof, as will be further elaborated below. Although FIG. 2 illustrates three actuator assemblies 138, mounted to, and equally spaced, around an inner surface of the frame 126, it should be clear that a different number of actuator assemblies 138 may be utilized, that the actuator assemblies 138 can be mounted to the frame 126 around its outer surface, and that the circumferential spacing between actuator assemblies 138 can be unequal.

FIGS. 3A-3B show an exemplary embodiment of an actuator assembly 138. An actuator assembly 138 may include a hollow outer member 140, secured to a component of the valve 120, such as the frame 126, at a first location, and an inner member 154 secured to a component of the valve 120, such as the frame 126, at a second location, axially spaced from the first location.

FIG. 3A constitutes a view in perspective of an exemplary inner member 154, having an inner member proximal end 156 and an inner member distal end 158. The inner member 154 comprises an inner member coupling extension 164 proximate to its distal end 158, which may be formed as a pin extending radially outward from the inner member 154, configured to be received within respective openings or apertures of struts 128 intersecting at a junction 130 or an apex 129, 131. The inner member 154 may further comprise a linear rack having a plurality of teeth 162 along at least a portion of its length. According to some embodiments, one surface of the inner member 154 comprises a plurality of teeth 162.

The terms "including" and/or "having", as used herein (including the specification and the claims), are defined as comprising (that is, open language).

FIG. 3B shows the actuation inner member 154 disposed within a lumen 146 of the outer member 140. The outer member 140 is shown with partial transparency in FIG. 3B for sake of clarity. The outer member 140 comprises an outer member proximal end 142 defining a proximal opening, and an outer member distal end 144 defining a distal opening. The outer member 140 can further comprise an outer member coupling extension 148 proximate to its proximal end 142, which may be formed as a pin extending radially outward from the external surface of the outer member 140, configured to be received within respective openings or apertures of struts 128 intersecting at a junction 130 or an apex 129, 131.

The outer member 140 may further comprise a spring biased arm 150, attached to or extending from one sidewall of the outer member 140 and having a tooth or pawl 152 at its opposite end, biased inwards toward the actuation inner member 154 when disposed within the outer member lumen 146.

At least one of the inner or outer member 154 or 140, respectively, is axially movable relative to its counterpart. The actuator assembly 138 in the illustrated embodiments, comprises a ratchet mechanism or a ratchet assembly, wherein the pawl 152 of the outer member 140 is configured to engage with the teeth 162 of the inner member 154. The pawl 152 can have a shape that is complementary to the shape of the teeth 162, such that the pawl 152 allows a sliding movement of the inner member 154 in one direction relative to the outer member 140, for example in a proximally oriented direction, and resists sliding movement of the inner member 154 in the opposite direction, such as a distally oriented direction, when the pawl 152 is in engagement with the teeth 162 of the inner member 154.

The arm 150 can be formed of a flexible or resilient portion of the outer member 140 that extends over and contact, at pawl 152, an opposing side of the outer surface of the inner member 154. According to some embodiments, the arm 150 can be in the form of a leaf spring that can be integrally formed with the outer member 140 or separately formed and subsequently connected to the outer member 140. The arm 150 is configured to apply a biasing force against the outer surface of the inner member 154, so as to ensure that under normal operation, the pawl 152 stays engaged with the teeth 162 of the inner member 154.

Figure 3C:
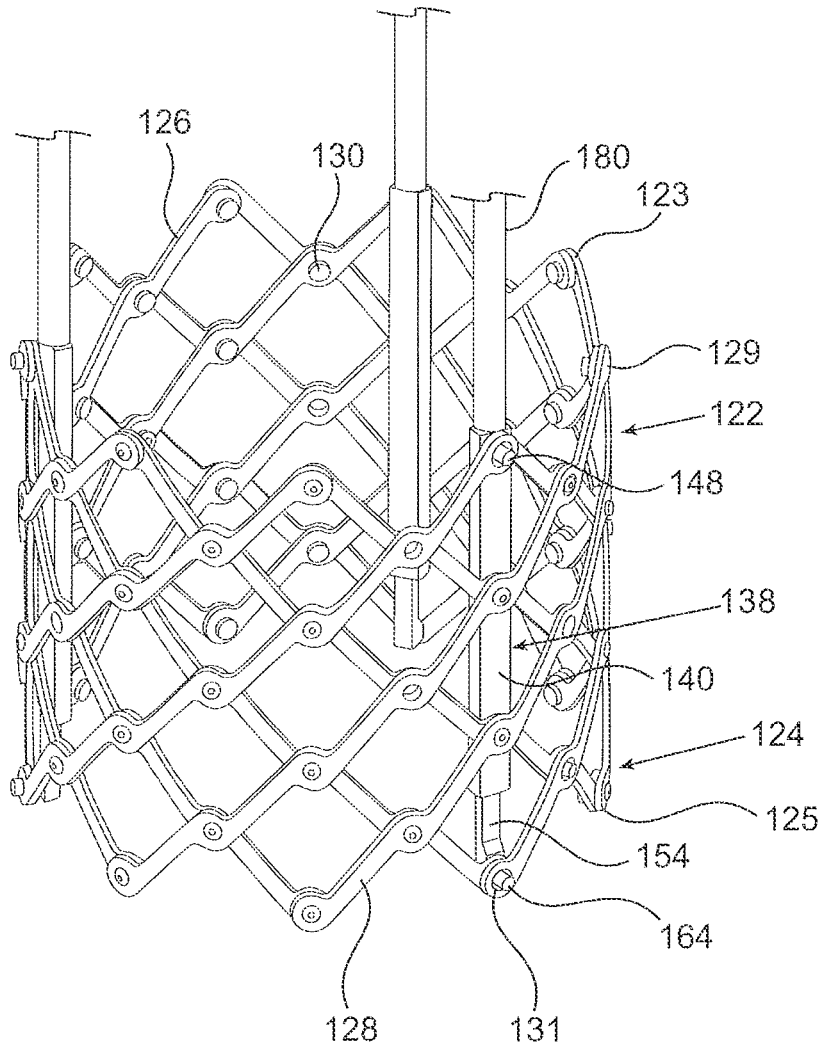
FIG. 3C constitutes a view in perspective of a prosthetic valve including multiple actuator assemblies of the type shown in FIG. 3B.

According to some embodiments, the inner member 154 further comprises an inner member threaded bore 160 extending from its proximal end 156, configured to receive and threadedly engage with a threaded portion 174 (shown for example in FIGS. 4B-4C) of a corresponding actuation member 172. FIG. 3C shows a view in perspective of a valve 120 in an expanded state, having its actuator assemblies 138 connected to actuation members 172 (hidden from view within the support sleeves 180) of the delivery apparatus 102. The leaflets 132 and skirt 136 are omitted from FIG. 3C to expose the actuator assemblies 138 attached to the frame 126. When actuation members 172 are threaded into the inner members 154, axial movement of the actuation members 172 causes axial movement of the inner members 154 in the same direction.

Figure 4A:
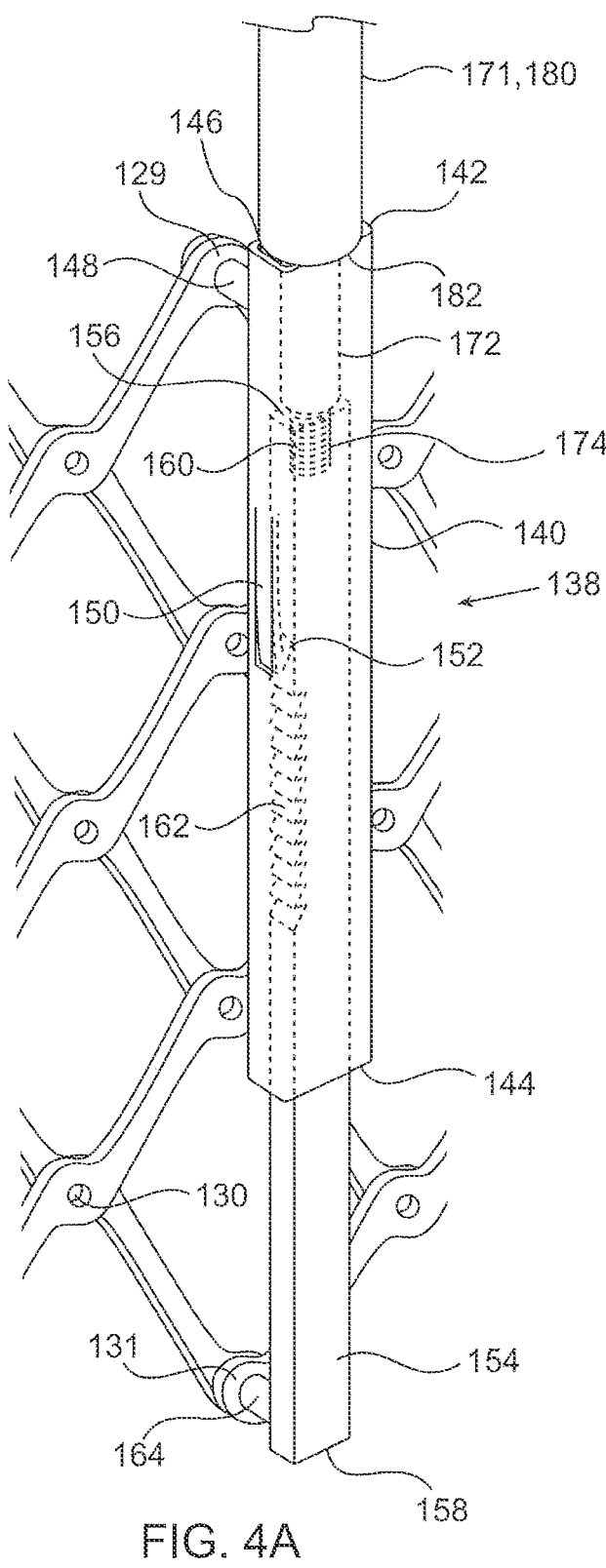
FIGS. 4A-4C show an actuator assembly of the type shown in FIG. 3B in different operational states thereof.
Figure 4B:
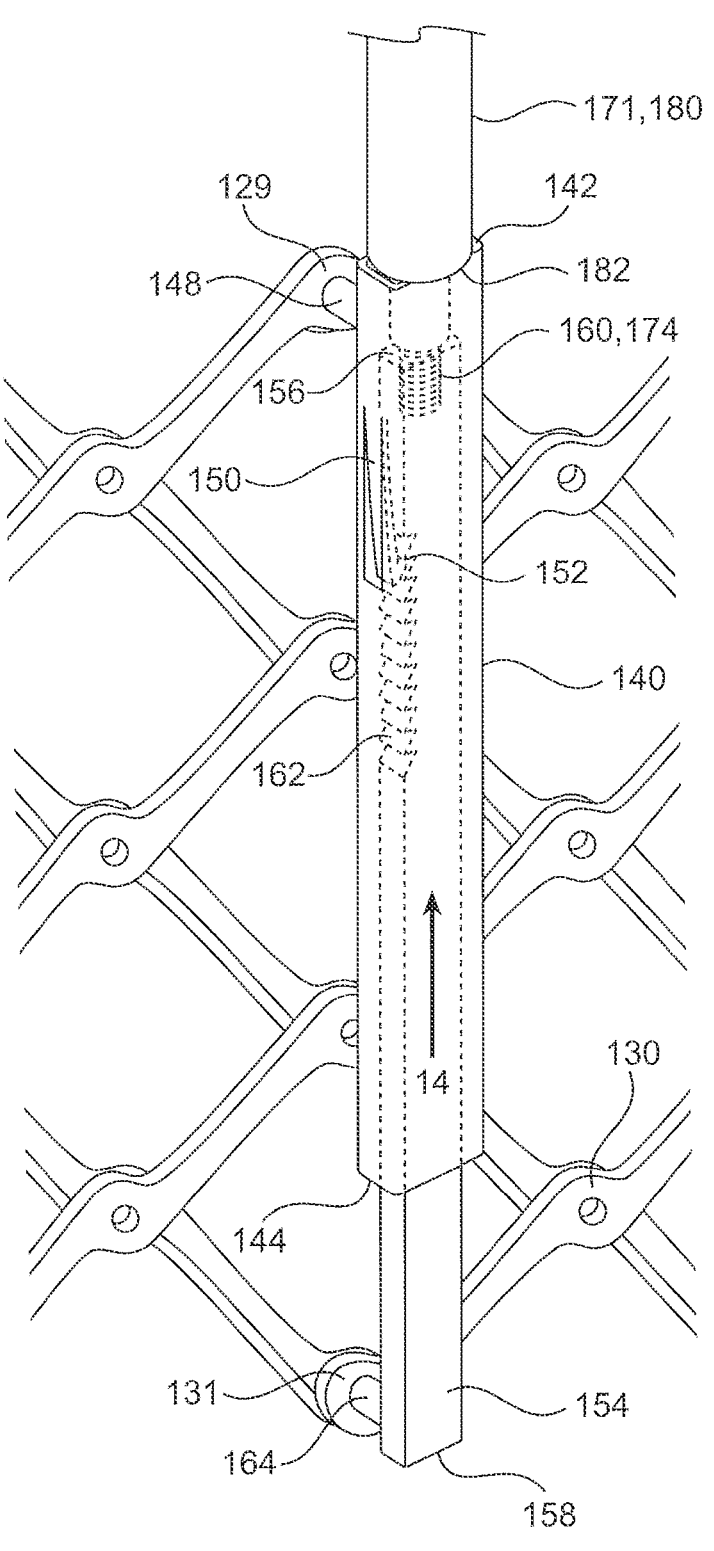
Figure 4C:
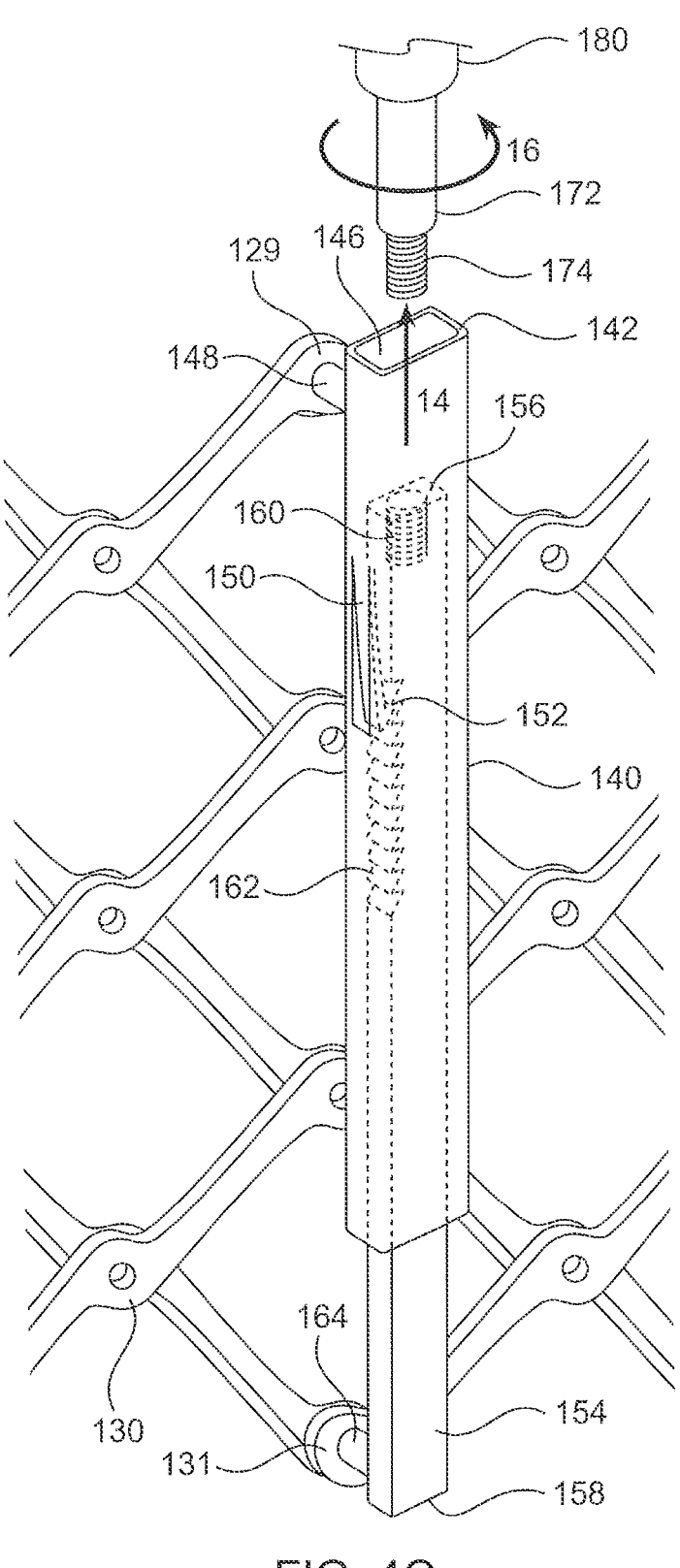

FIGS. 4A-4C illustrate a non-binding configuration representing actuation of the actuator assemblies 138 via the actuation arm assemblies 171 to expand the prosthetic valve 120 from a radially compressed state to a radially expanded state. FIG. 4A shows an actuator assembly 138, having an outer member 140, secured to the frame 126 at a first location, and an inner member 154 secured to the frame 126 at a second location. According to some embodiments, the first location can be positioned at an outflow end portion 122, and the second location can be positioned at the inflow end portion 124. In the illustrated embodiment, the outer member 140 is secured to an outflow apex 129 via outer member coupling extension 148, and the inner member 154 is secured to an inflow apex 131 via inner member coupling extension 164. A proximal portion of the inner member 154 extends, through the distal opening of the outer member distal end 144, into the outer member lumen 146.

The actuator assembly 138 is shown in FIG. 4A in a radially compressed state of the frame valve 120, wherein the outflow and inflow apices 129 and 131, respectively, are relatively distanced apart from each other along the axial direction, and the inner member proximal end 156 is positioned distal to the outer member proximal end 142.

As further shown in FIG. 4A, the distal portion 174 of the actuation member 172 is threadedly engaged with the proximal threaded bore 160 at the proximal end 156 of the inner member 154. According to some embodiments, as shown in FIGS. 4A-4C, the distal portion 174 of the actuation member 172 includes external threads, configured to engage with internal threads of the proximal bore 160 of the inner member 154. According to alternative embodiments, an inner member may include a proximal extension provided with external threads, configured to be received in and engage with internal threads of a distal bore formed within the actuation member (embodiments not shown).

The support sleeve 180 surrounds the actuation member 172 and may be connected to the handle 110. The support sleeve 180 and the outer member 140 are sized such that the distal lip 182 of the support sleeve 180 can abut or engage the outer member proximal end 142, such that the outer member 140 is prevented from moving proximally beyond the support sleeve 180.

In order to radially expand the frame 126, and therefore the valve 120, the support sleeve 180 can be held firmly against the outer member 140. The actuation member 172 can then be pulled in a proximally oriented direction 14, as shown in FIG. 4B. Because the support sleeve 180 is being held against the outer member 140, which is connected to an outflow apex 129, the outflow end 123 of the frame 126 is prevented from moving relative to the support sleeve 180. As such, movement of the actuation member 172 in a proximally oriented direction 14 can cause movement of the inner member 154 in the same direction, thereby causing the frame 126 to foreshorten axially and expand radially.

More specifically, as shown for example in FIG. 4B, the inner member coupling extension 164 extends through openings in two struts 128 interconnected at an inflow apex 131, while the outer member coupling extension 148 extends through openings in two struts 128 interconnected at an outflow apex 129. As such, when the inner member 154 is moved axially, for example in a proximally oriented direction 14, within the outer member 140, the inner member coupling extension 164 moves along with the inner member 154, thereby causing the portion to which the inner member coupling extension 164 is attached to move axially as well, which in turn causes the frame 126 to foreshorten axially and expand radially.

The struts 128 to which the inner member coupling extension 164 is connected are free to pivot relative to the coupling extension 164 and to one another as the frame is expanded or compressed. In this manner, the inner member coupling extension 164 serves as a fastener that forms a pivotable connection between those struts 128. Similarly, struts 128 to which the outer member coupling extension 148 is connected are also free to pivot relative to the coupling extension 148 and to one another as the frame is expanded or compressed. In this manner, the outer member coupling extension 148 also serves as a fastener that forms a pivotable connection between those struts 128.

When the pawl 152 is engaged with the teeth 162, the inner member 154 can move in one axial direction, such as the proximally oriented direction 14, but cannot move in the opposite axial direction. This ensures that while the pawl 152 is engaged with the teeth 162, the frame 126 can radially expand but cannot be radially compressed. Thus, after the prosthetic valve 120 is implanted in the patient, the frame 126 can be expanded to a desired diameter by pulling the actuation member 172. In this manner, the actuation mechanism also serves as a locking mechanism of the prosthetic valve 120.

Once the desired diameter of the prosthetic valve 120 is reached, the actuation member 172 may be rotated in direction 16 to unscrew the actuation member 172 from the inner member 154, as shown in FIG. 4C. This rotation serves to disengage between the distal threaded portion 174 of the actuation member 172 and the inner member threaded bore 160, enabling the actuation arm assemblies 171 to be pulled away, and retracted, together with the delivery apparatus 102, from the patient's body, leaving the prosthetic valve 120 implanted in the patient. The patient's native anatomy, such as the native aortic annulus in the case of transcatheter aortic valve implantation, may exert radial forces against the prosthetic valve 120 that would strive to compress it. However, the engagement between the pawl 152 and the teeth 162 of the inner member 154 prevents such forces from compressing the frame 126, thereby ensuring that the frame 126 remains locked in the desired radially expanded state.

Thus, the prosthetic valve 120 is radially expandable from the radially compressed state shown in FIG. 4A to the radially expanded state shown in FIG. 4B upon actuating the actuator assemblies 138, wherein such actuation includes approximating the second locations to the first locations of the valve. The prosthetic valve 120 is further releasable from the delivery apparatus 102 by decoupling each of the actuation arm assemblies 171 from each corresponding actuator assemblies 138 that was attached thereto.

While the inner member 154 and the outer member 140 are shown in the illustrated embodiment connected to an inflow apex 131 and an outflow apex 129, respectively, it should be understood that they can be connected to other junctions 130 of the frame 126. For example, the inner member coupling extension 164 can extend through openings formed in interconnected struts at a junction 130 at the inflow end portion 124, proximal to the inflow apices 131. Similarly, the outer member coupling extension 148 can extend through openings formed in interconnected struts at a junction 130 at the outflow end portion 122, distal to the outflow apices 129.

While the frame is shown above to expand radially outward by axially moving the inner member 154 in a proximally oriented direction, relative to the outer member 140, it will be understood that similar frame expansion may be achieved by axially pushing an outer member 140 in a distally oriented direction, relative to an inner member 154. Moreover, while the illustrated embodiments show the outer member 140 affixed to an outflow end portion 122 of the frame 126, and an inner member 154 affixed to an inflow end portion 124 of the frame 126, in alternative embodiments, the outer member 140 may be affixed to the inflow end portion 124 of the frame 126, while the inner member 154 may be affixed to the outflow end portion 122 of the frame 126.

According to some embodiments, the handle 110 can comprise control mechanisms which may include steerable or rotatable knobs, levers, buttons, and such, which are manually controllable by an operator to produce axial and/or rotatable movement of different components of the delivery apparatus 102. For example, the handle 110 may comprise one or more manual control knobs, such as a manually rotatable control knob that is effective to pull the actuation members 172 when rotated by the operator.

According to other embodiments, control mechanisms in handle 110 and/or other components of the delivery apparatus 102 can be electrically, pneumatically and/or hydraulically controlled. According to some embodiments, the handle 110 can house one or more electric motors which can be actuated by an operator, such as by pressing a button or switch on the handle 110, to produce movement of components of the delivery apparatus 102. For example, the handle 100 may include one or more motors operable to produce linear movement of components of the actuation arm assemblies 171, and/or one or more motors operable to produce rotational movement of the actuation members 172 to disconnect the actuator member distal threaded portion 174 from the actuation inner member threaded bore 160. According to some embodiments, one or more manual or electric control mechanism is configured to produce simultaneous linear and/or rotational movement of all the actuation members 172.

While a specific actuation mechanism is described above, utilizing a ratcheting mechanism between the inner and the outer members of the actuation assemblies 138, other mechanisms may be employed to promote relative movement between inner and outer members of actuation assemblies, for example via threaded or other engagement mechanisms. Further details regarding the structure and operation of mechanically expandable valves and delivery system thereof are described in U.S. Pat. No. 9,827,093, U.S. Patent Application Publication Nos. 2019/0060057, 2018/0153689 and 2018/0344456, and U.S. Patent Application Nos. 62/870,372 and 62/776,348, all of which are incorporated herein by reference.

Prosthetic valve 120 expansion against the surrounding tissue may pose a variety of risks associated with a mismatch between the valve's expansion diameter and the surrounding tissue. One complication is related to valve over-expansion, which may exert excessive radial forces on the surrounding anatomy, resulting in potential damage to the tissue or even annular rupture. On the other hand, valve under-expansion might increase the risk of aortic valve or mitral valve regurgitation. Inappropriate expansion may also result in unfavorable hemodynamic performance across the valve 120, such as increased pressure gradients or flow disturbances resulting from diameter mismatch, which may be associated with increased risk of thrombus formations.

Thus, in order to avoid the deleterious effects of either annular rupture, inferior hemodynamic performance or valve regurgitation, arising due to either over-expansion or under-expansion, respectively, of the valve frame 126, a clinician should be able to control the degree of frame 126 expansion according to real-time feedback received during the procedure, indicating, for example, current valve diameter and/or current forces exerted by the valve on its surroundings, or reactive forces of the surrounding tissue, resisting valve expansion.

According to an aspect, there is provided a delivery assembly 100 equipped with at least one optic fiber sensor attached to at least one component of the delivery assembly 100, such as to the prosthetic valve 120, to the delivery apparatus 102, or to both. Utilization of optic fiber sensors may be advantageous due to their light weight, miniature dimension, low power consumption, high sensitivity, environmental ruggedness, and low cost.

For the sake of simplicity, prosthetic valves 120 will be shown throughout FIGS. 5A-15C without the leaflets 132 or the skirt 136. Moreover, partial sectional views of actuation arm assemblies 171 and/or actuator assemblies 138 will be shown in otherwise perspective views of prosthetic valves 120 in FIGS. 5A-15C, to expose inner structural configurations of optic fibers attached to and/or extending through components of the arm assemblies 171 and/or actuator assembly 138.

Figure 5A:
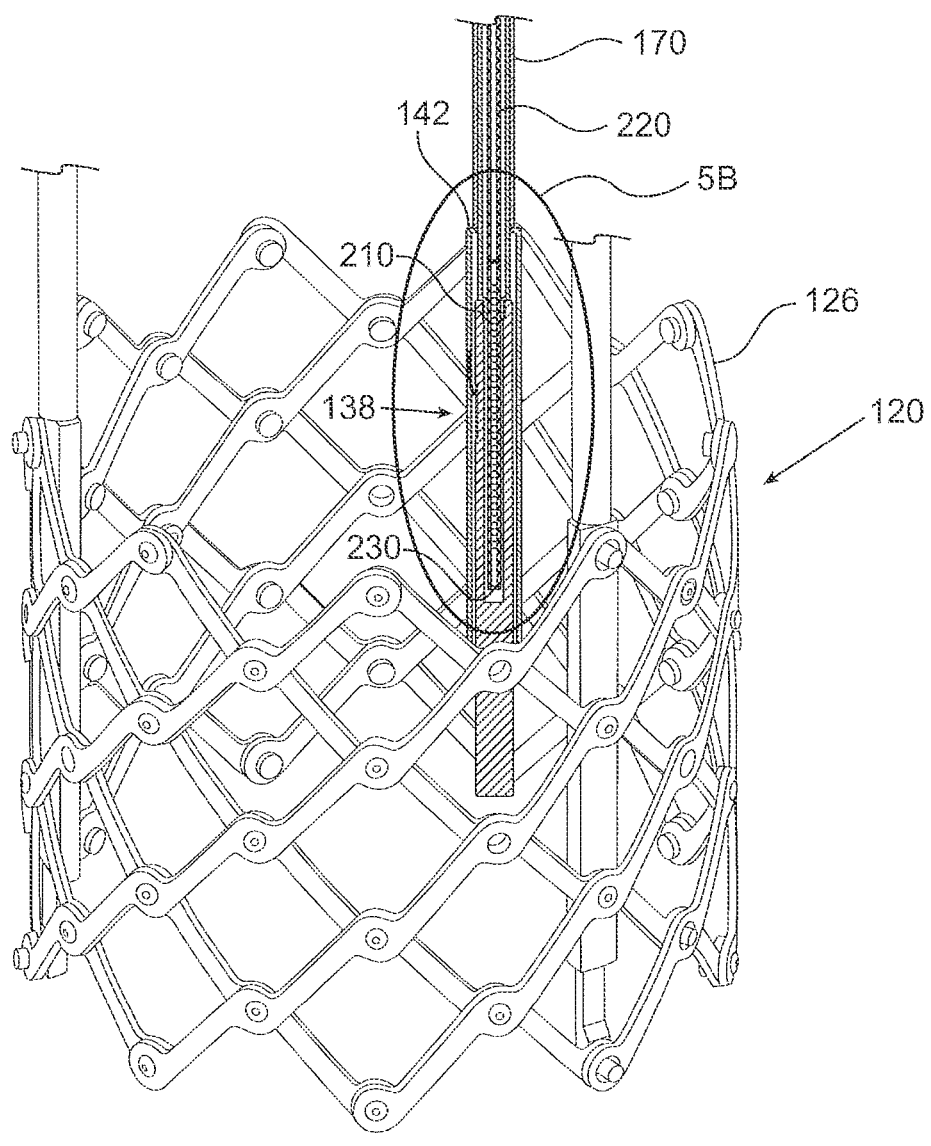
FIGS. 5A-5C show different views of a delivery assembly equipped with an optic fiber assembly, according to some embodiments.
Figure 5C:
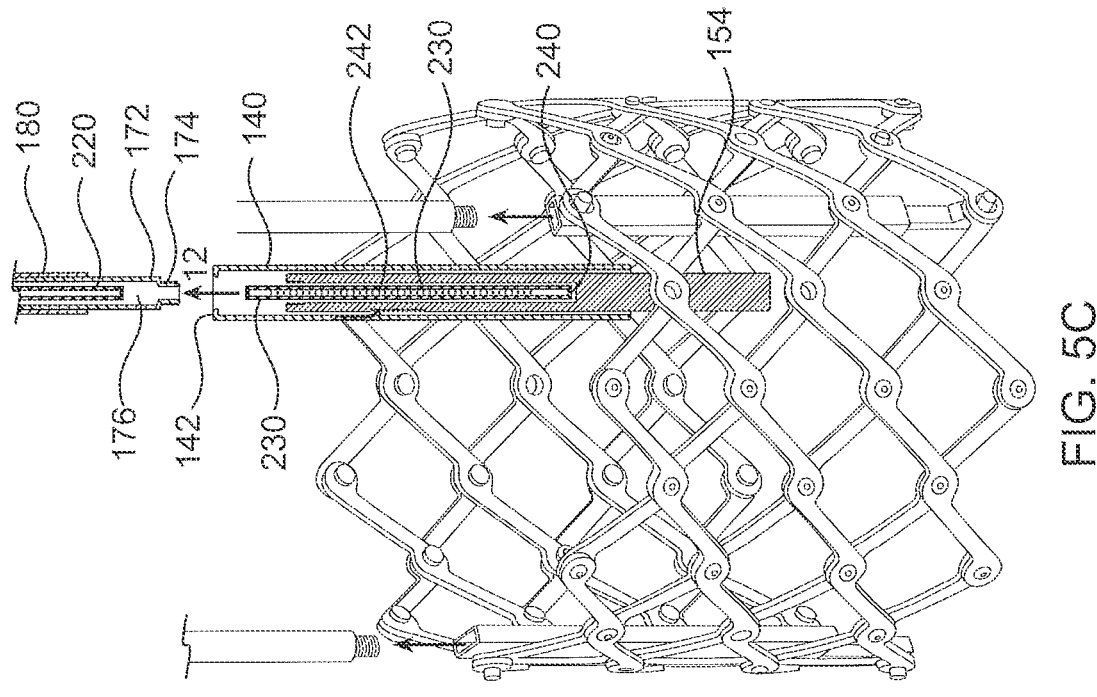
Figure 5B:
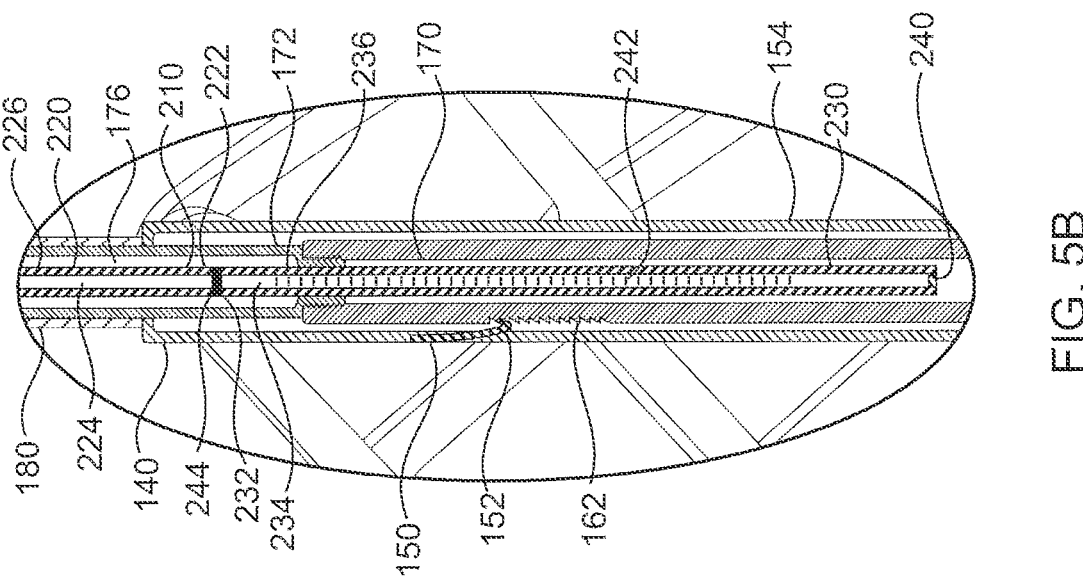

Reference is now made to FIGS. 5A-5C, showing an embodiment of a delivery assembly 100 equipped with a mechanically expandable valve 120, having at least one optic fiber assembly 210 extending through the delivery apparatus 102 and attached at its distal portion to the frame 126. In some instances, the optic fiber assembly 210 can extend from the handle 110, through or along at last one of the components of an actuation arm assembly 171, such as the support sleeve 180 or the actuation member 172 retained therein, toward the actuator assembly 138, having its distal portion attached to a component of the actuator assembly 138, such as the inner member 154.

FIG. 5A shows a view in perspective of a mechanically expandable valve 120 having its actuation assemblies 138 connected to actuation members 172, wherein a fiber optic assembly 210 extends through an actuation member 172 toward the inner member 154. The leaflets 132 and skirt 136 are omitted from FIGS. 5A-5C for purposes of clarity, and the actuator assembly 138 and the respective actuation member 172 attached thereto are shown in partially sectional view to expose the fiber optic assembly 210 extending there-through. FIG. 5B shows a zoomed-in view of region 5B in FIG. 5A.

According to some embodiments, the optic fiber assembly 210 comprises two optic fiber sections, detachably optically coupled to each other. Specifically, the optic fiber assembly 210 comprises a first optic fiber section 220, extending from the handle 110 through or along the actuation arm assembly 171, up to a first fiber distal end 222, and a second optic fiber section 230 distal to the first optic fiber section 220, connected to a component of the valve 120, such as a component of the actuator assembly 138. According to some embodiments, the second optic fiber section 230 is connected to the inner member 154.

The second optic fiber section 230 extends between a second fiber proximal end 232, positioned at or distal to the valve proximal end 122, and a second fiber distal end 240. According to some embodiments, the second fiber distal end 240 is positioned at, or proximal to, the inflow end portion 124. According to alternative embodiments, the second fiber distal end 240 is positioned at other regions of the valve 120, including any region distal to the second fiber proximal end 232, or even a region of the valve 120 which is lateral to the second fiber proximal end 232.

The first optic fiber section 220 can include at least one first optic core, and the second optic fiber section 230 can include at least one second core. In the embodiment illustrated in FIGS. 5A-5C, the first optic fiber section 220 comprises a first optic core 224 surrounded by a first fiber cladding 226, and the second optic fiber section 230 comprises a second optic core 234 surrounded by a second fiber cladding 236. Each of the first and/or second optic fiber sections 220 and 230 can further include a surrounding polymeric buffer coating (not shown) around the cladding 226, 236, serving as a protective buffer from the surrounding environment.

The first optic fiber section 220 is connected to the delivery apparatus 102. According to some embodiments, the first optic fiber section 220 is connected to the handle 110 or to any component connected to or retained within the handle 110. According to some embodiments, the first optic fiber section 220 is connected to a component of the actuation arm assembly 171, such as the support sleeve 180 and/or the actuation member 172.

According to some embodiments, the outer diameter of the first optic fiber section 220 is substantially equal to the outer diameter of the second optic fiber section 230. According to some embodiments, the outer diameter of the first optic core 224 is substantially equal to the outer diameter of the second optic core 234.

The term 'substantially equal', when referring to a specific measure as used herein, means no more and no less than 10% of the measure. For example, a diameter of one component is substantially equal to the diameter of a second component, if the diameter of the first component is within the boundaries of 90%-110% of the second diameter.

In the embodiment illustrated in FIGS. 5A-5B, the first optic fiber section 220 extends through an internal channel 176 formed within the actuation member 172, and at least a portion of the second optic fiber section 230 extends through a channel 170 formed within the inner member 154 of the actuator assembly 138.

According to some embodiments, the channels 176 and 170 are dimensioned to accommodate the first and second optic fiber sections 220 and 230, respectively, in a relatively tight manner, so as to prevent or nearly prevent lateral movement of the fiber sections 220, 230 within the channels 176, 170, respectively. According to some embodiments, the difference between the inner diameter of each of channels 176, 170 and the outer diameter of each of fiber sections 220, 230 is not greater than 30% of the diameter of optic cores 224, 234, respectively. According to some embodiments, the difference between the inner diameter of each of channels 176, 170 and the outer diameter of each of fiber sections 220, 230 is not greater than 20% of the diameter of optic cores 224, 234, respectively. According to some embodiments, the difference between the inner diameter of each of channels 176, 170 and the outer diameter of each of fiber sections 220, 230 is not greater than 10% of the diameter of cores 224, 234, respectively.

According to some embodiments, as further shown in FIGS. 5A-5B, the first optic fiber section 220 is detachably optically coupled to the second optic fiber section 230 when the actuation members 172 are connected to the actuator assemblies 138. Specifically, the first fiber distal end 222 is optically coupled to the second fiber proximal end 232 when the actuation member distal portion 174 is fully engaged with the inner member threaded bore 160.

The term 'fully engaged' relates to a state of engagement between the actuation member distal portion 174 and the inner member threaded bore 160 wherein actuation member 172 cannot move further in a distally oriented direction relative to the inner member 154, as opposed to a 'partially engaged' state, in which the actuation member distal portion 174 may be partially rotated to translate in a proximally oriented direction relative to the inner member 154, prior to disengagement therefrom.

According to some embodiments, the optic fiber assembly 210 further comprises an interface 244 between the first fiber distal end 222 and the second fiber proximal end 232. The interface is configured to provide detachable optical coupling between the first and second fiber optic sections 220 and 230, such that signals may be communicated between the first and second fiber optic sections 220 and 230, when optically coupled to each other, and wherein both are optically decoupled when the first fiber distal end 222 is detached from the second fiber proximal end 232. Decoupling of the first fiber optic section 220 from the second fiber optic section 230 may be controlled by the handle 110, and may be a passive decoupling which occurs once the delivery apparatus 102 is detached from the prosthetic valve 120, for example by unscrewing the actuation members 172 from the actuator assemblies 138.

According to some embodiments, the interface 244 comprises an optical connector, configured to releasably couple the first fiber distal end 222 and the second fiber proximal end 232 and allow signal communication there between. When communicating signals between different optic fiber sections, alignment of the optic fiber sections may be desirable, as even a slight misalignment may lead to signal losses. According to some embodiments, an optical connector 244 includes alignment features configured to align the first fiber distal end 222 and the second fiber proximal end 232.

According to some embodiments, optical coupling between the first optic fiber section 220 and the second optic fiber section 230 is achieved by placement of the first fiber distal end 222 in contact with the second fiber proximal end 232, and optical decoupling is achieved by pulling the first fiber distal end 222 away from the second fiber proximal end 232. In such embodiments, the interface 244 between the first optic fiber section 220 and the second optic fiber section 230 is not realized as a distinct physical component, but rather may be defined as the contact area between the first fiber distal end 222 and the second fiber proximal end 232.

According to some embodiments, the optical coupling of the interface 244 is realized as a physical contact (PC) connection between the first fiber distal end 222 and the second fiber proximal end 232, wherein the first optic core 224 and the second optic core 234 are aligned with each so as to optimize performance and minimize optic light loss at the interface 244 there between.

According to some embodiments, the optical coupling 244 is realized as a flat PC, when the first fiber distal end 222 and the second fiber proximal end 232 comprise flat, and preferably polished, end faces. According to some embodiments, the optical coupling 244 is realized as an angled PC, when the first fiber distal end 222 and the second fiber proximal end 232 comprise complementary angled end faces, for example at an angle of about 8 degrees (embodiment not shown).

The term 'about', as used herein, means in a range of ±10% from a referred value.

FIG. 5C shows the actuation member 172 released or disengaged from the actuator assembly 138, for example after being rotated around its longitudinal axis and pulled in a proximally oriented direction 12. In this state, the first optic fiber section 220, which is connected to the delivery apparatus 102, is pulled therewith and is disconnected from the second optic fiber section 230, which remains connected to the valve 120, and more specifically, to the inner member 154.

According to some embodiments, the fiber optic assembly 210 comprises a fiber optic strain sensor. According to some embodiments, the second optic fiber section 230 comprises a fiber optic strain sensor, configured to measure the axial strain of the inner member 154, for example.

According to some embodiments, the second optic fiber section 230 comprises a plurality of axially spaced Fiber Bragg Gratings (FBGs) 242, disposed along at least a portion of the second optic core 234, utilized to determine the strain experienced by the second optic fiber section 230. Tension or compression loads exerted on the second optic fiber section 230 cause the spacing between the FBGs 242 to change, which in turn shifts the wavelengths of light waves reflected back by the FBGs. Quantitative and/or qualitative strain values of the strain experienced by the second optic fiber section 230, can be calculated from such changes. According to some embodiments, all of the FBGs may be equally spaced from each other along the axial direction.

Since the second optic fiber section 230 is attached to the actuation inner member 154, the strain sensed by the optic fiber assembly 210 is the strain at the actuation inner member 154.

Assuming that the stress-strain relationship for the actuation inner member 154 is known, the axial stress experienced by the actuation inner member 154 can be derived from the measured axial strain. In some instances, the stress-strain relationship may be a linear or nearly-linear relationship.

Further assuming that the relationship between axial stress and radial stress is known for the specific valve type, the radial stress can then be derived from the calculated axial stress. In some instances, a linear or nearly linear relationship exists between axial stress and radial stress for a prosthetic valve 120, wherein the linear coefficient may be derived for each prosthetic valve diameter.

Thus, based on the assumptions of known relationships as elaborated above, a fiber optic strain assembly 210 may be utilized to provide an indication, qualitative or quantitative evaluation, or any other feedback regarding the stress experienced by the valve 120, in real-time, in-vivo, during a valve 120 implantation procedure.

According to some embodiments, an optic fiber strain assembly 210 may be utilized to provide real-time estimation of the valve's current expansion diameter. One configuration that may enable diameter estimation, includes a portion of the second optic fiber section 230 attached to the frame 126, or to components affixed to the frame 126, in a circumferential direction instead of being affixed to a component of the actuator assembly 138 only in an axial direction. In such configurations (not shown), wherein the FBGs 242 are circumferentially spaced from each other, the change in shift of light wavelengths results from the change in the valve's diameter, can provide an estimate and/or quantitative evaluation of the current valve diameter.

According to some embodiments, the delivery assembly 100 comprises a plurality of optic fiber strain assemblies 210, for example three optic fiber strain assemblies 210, each of which is attached to a respective actuator member 172 and actuation assembly 138. Advantageously, a plurality of fiber optic strain sensors 210 disposed at different regions around the valve 120 can provide feedback regarding radial stresses experienced at different regions along the circumference of the valve 120.

In use, a delivery assembly 100 may be utilized to deliver a mechanically expandable prosthetic valve 120 toward a desired implantation site in a crimped state, having the actuation members 172 attached to the actuator assemblies 138 of the valve 120, and the first optic fiber section 220 optically coupled to the second optic fiber section 230.

Once the crimped valve 120 is positioned at the desired implantation site, the handle 110 may be maneuvered to pull the actuation members 172 to gradually expand the valve 120. During the expansion of the valve 120, at least one fiber optic strain assembly 210 provides real-time feedback regarding either the stress experienced by the valve 120 due to the resistance of the surrounding tissue against which it is expanded, or the valve diameter. The feedback can be visual, for example via a display 116 or LED lights 118 positioned at the handle 110. Such indication may assist the clinician in decision making regarding the next required steps of the implantation procedure.

Once the valve 120 is sufficiently expanded, the handle 110 can be further maneuvered to rotate the actuation members 172 around their central axes, thereby optically decoupling the first and second optic fiber sections 220 and 230. Further rotation of the actuation members 172 serves to disengage them from the actuator assemblies 138, such that the delivery apparatus 102, including the actuation members 172 and the first optic fiber section 220, can be retracted from the patient's body.

The expanded valve 120 remains in the implantation site, having the second optic fiber section 230 attached thereto in a dysfunctional state. Advantageously, the small dimensions of optical fibers, usually in the range of 100-200 microns, enable the second optic fiber section 230 to remain in the valve 120 in a dysfunctional state, without interfering with the valve's functioning and without externally modifying its structure or dimensions.

A further advantage of utilizing optical fibers is that one section thereof, attached to external powering and control components, for example—at the handle 110, can be safely decoupled within a patient's body from a second section, configured to measure a desired parameter within the patient's body, without posing a risk of exposing the patient to electrical current, as no electrical current is involved.

FIGS. 5A-5C show an exemplary configuration in which the interface 244 is located within the distal portion of the actuation member channel 176, for example in the vicinity of the actuation member distal threaded portion 174, such that at least a portion of the second fiber optic section 230 extends from the inner member channel 170 into the actuation member channel 176. In alternative configurations, the interface 244 can be positioned in other regions, such as, for example, the inner member channel 170, having the first fiber optic section 220 extending from the actuation member channel 176 into the inner member channel 170 (configuration not shown).

In all configurations pertaining to the position of the interface 244, it is preferable that the interface 244 is located at the level of, or distal to, the outer member proximal end 142, so that once the first fiber optic section 220 is optically decoupled and retracted from the patient's body along with the remainder of the delivery apparatus 102, the second fiber optic section 230 remains hidden within the actuator assembly 138 and does not have a proximal portion thereof freely extending out of the actuator assembly 138. Stated otherwise, it is preferable that the first fiber optic section 220 does not extend beyond the outer member proximal end 142.

While the interface 244 between the optically coupled first and second optical sensor sections 220 and 230 is exemplified above as a simple contact between their end faces, it will be clear that other interfaces may be utilized for detachable optical coupling. For example, the interface may include a gap configured to transfer light between the first and second optic cores 224 and 234, with minimal interference. For example, the first fiber distal end 222 may be glued or fused to the second fiber proximal end 232 in a manner that application of a selected amount of pull force, or alternatively, rotational force, that may be exerted thereon during rotation of the actuation member 172, can break the adhesive bonds and allow the first fiber optic section 220 to be withdrawn, and optically decoupled from the first fiber optic section 230.

An implanted prosthetic valve 120 might form a stenotic region at the site of implantation, which is usually narrower than the native annulus. The narrower orifice results in a portion of the blood flow's potential energy, namely pressure, being converted into kinetic energy, namely velocity, resulting in flow acceleration and pressure drop. Some of the energy may be irreversibly dissipated as heat, for example due to flow turbulences. The remaining portion of kinetic energy, which is recovered back as potential energy, is termed the 'pressure recovery'. Pressure recovery at the outflow region of the valve 120 may be correlated with clinical outcomes. Thus, it is desirable to provide means for measuring the profile of valve pressure recovery, therefore providing a valuable decision supporting measure for a clinician during valve deployment.

According to an aspect, there is provided a delivery assembly 100 comprising a plurality of optic fibers equipped with axially spaced optic fiber sensors or sensor heads, for example at their distal ends, configured to provide pressure data at two axially spaced measurement points, from which the pressure drop of pressure recovery can be derived. Such a delivery assembly 100 is capable of measuring blood pressure simultaneously at several points. Time-resolved pressure measurement can be correlated to flow using known empirical relationships established in clinical literature. Alternatively or additionally, a delivery assembly 100 may comprise at least one multi-core optic fiber, equipped with axially spaced optic fiber sensors or sensor heads, for example at the distal ends of each of the cores.

Reference is now made to FIGS. 6A-6D, showing an embodiment of a delivery assembly 100 equipped with a mechanically expandable valve 120, having at least one optic fiber assembly 310 extending through the delivery apparatus 102 and attached at its distal portion to the frame 126, and at least one continuous optic fiber 370 extending through the delivery apparatus 102 and attached at its distal portion to at last one of the components of an actuation arm assembly 171, such as the support sleeve 180 or the actuation member 172. In some instances, the optic fiber assembly 310 can extend from the handle 110, through or along at last one of the components of an actuation arm assembly 171, such as the support sleeve 180 or the actuation member 172, toward the actuator assembly 138, having its distal portion attached to a component of the actuator assembly 138, such as the inner member 154.

Figure 6A:
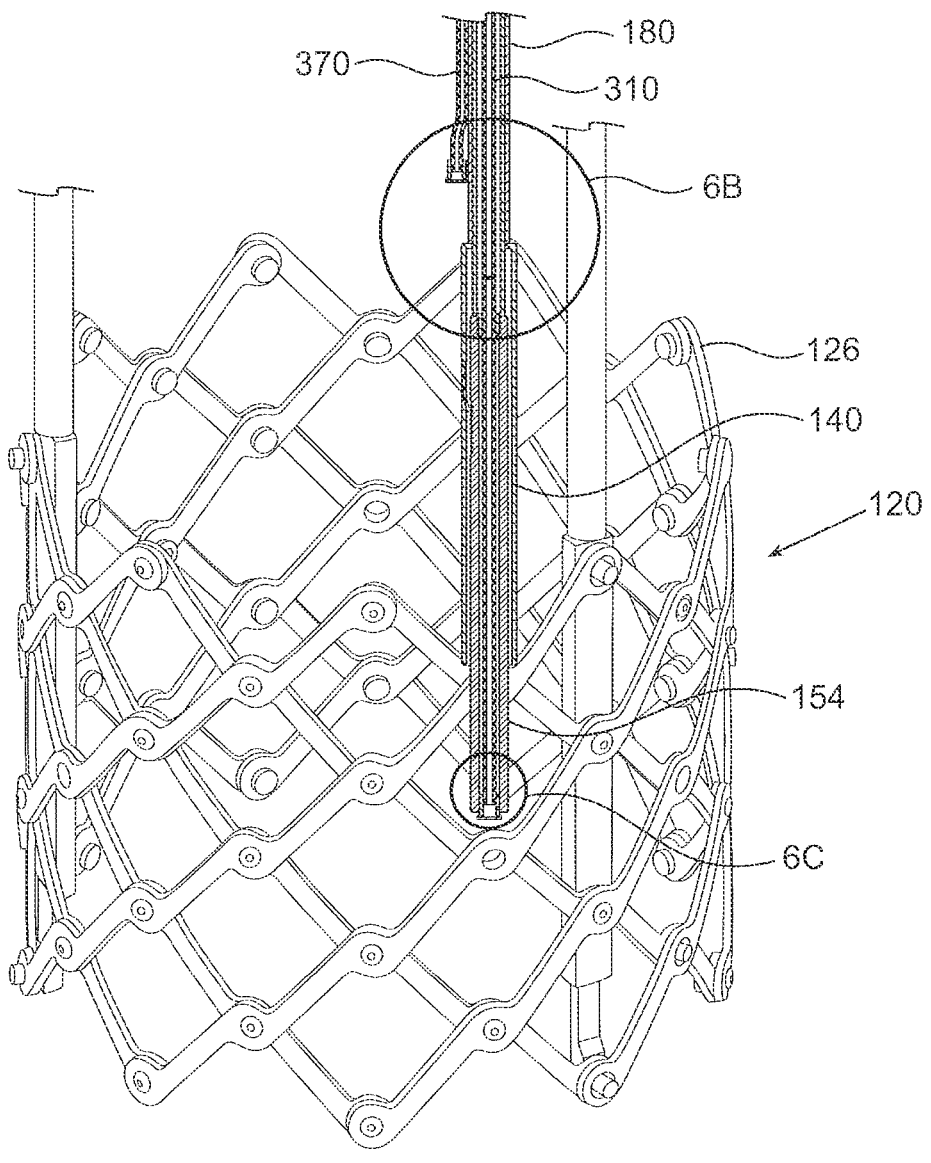
FIGS. 6A-6D show different views of a delivery assembly equipped with an optic fiber assembly and a continuous optic fiber, according to some embodiments.
Figure 6B:
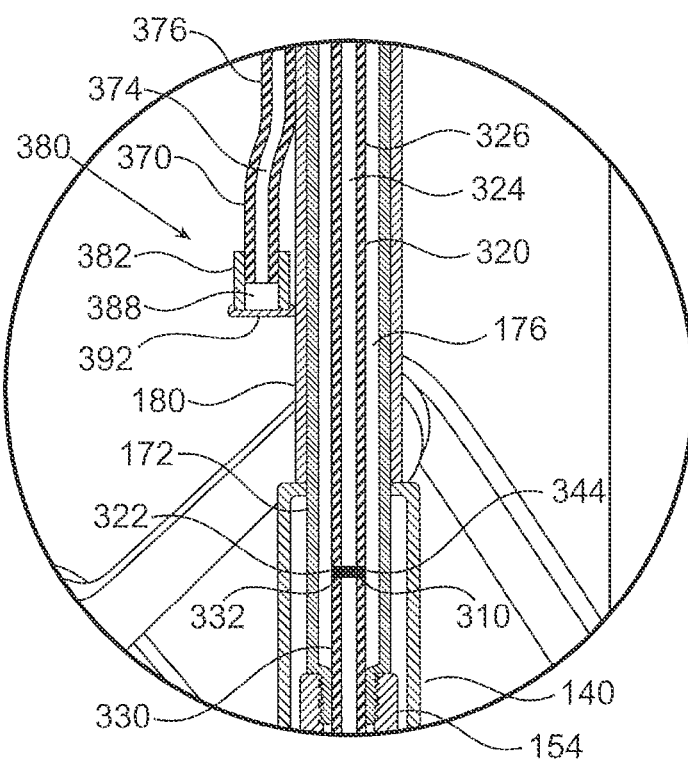
Figure 6C:
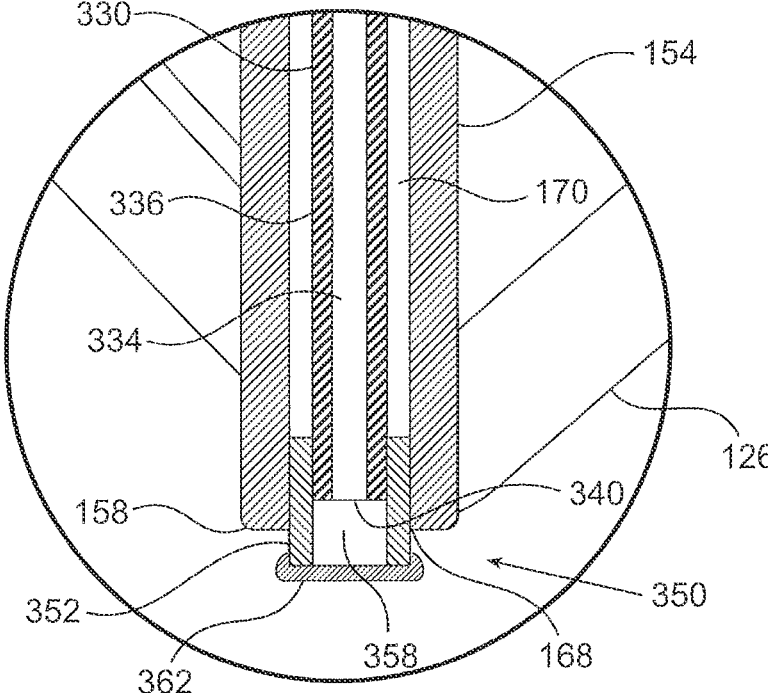

FIG. 6A shows a view in perspective of a mechanically expandable valve 120 having its actuation assemblies 138 connected to actuation members 172, wherein a fiber optic assembly 310 extends through an actuation member 172 toward the inner member 154, and wherein a continuous optic fiber 370 is attached to, and extends along, a support sleeve 180. FIG. 6B shows a zoomed in view of region 6B in FIG. 6A, and FIG. 6C shows a zoomed in view of region 6C in FIG. 6A.

Fiber optic assembly 310 is generally similar in structure to fiber optic assembly 210, comprising a first optic fiber section 320 detachably optically coupled to a second optic fiber section 330. The first optic fiber section 320 can be identical to the first optic fiber section 220, extending from the handle 110 up to a first fiber distal end 322, comprising a first optic core 324 surrounded by a first fiber cladding 326.

The second optic fiber section 330 is generally similar to the second optic fiber section 230, extending between a second fiber proximal end 332 positioned at, or distal to, the outflow end 123, and a second fiber distal end 340. According to alternative embodiments, the second fiber distal end 340 is positioned at, or proximal to, the outflow end 123. Unlike second optic fiber section 230 illustrated and described in accordance with FIGS. 5A-5C above, the second optic fiber section 330 further comprises an axial pressure sensing head 350 at its distal end 340, enabling the fiber optic assembly 310 to function as an optic fiber pressure sensor.

According to some embodiments, the axial sensing head 350 is a Fabry-Perot cavity based sensing head. Fabry-Perot sensors are attractive due to their miniature size and low costs of the sensing elements. The Fabry-Perot axial sensing head 350 may include a housing 352 attached to the second fiber distal end 340 having a front diaphragm 362 attached to the distal edges of housing 352. A front cavity 358, defined as an optical cavity, may be formed between the distal edge of a second fiber core 334 and the front diaphragm 362. Pressure may be monitored by detecting and measuring the deflection of the front diaphragm 362 to which pressure is applied.

A Fabry-Perot sensor detects pressure applied to the diaphragm in a direction perpendicular to the surface of the diaphragm. In an axial sensing head 350 configuration, the front cavity 358 and the front diaphragm 362 are coaxially aligned with the second fiber core 334. In this configuration, the optical characteristics of the light traveling along the fiber optic assembly 310 are responsive to the optical axis of the second fiber core 334. Specifically, when pressure is applied to the front diaphragm 362, the front diaphragm 362 bends into the front cavity 358, thereby changing the optical path of the light traveling through the second fiber core 334. The change in the optical path of the light in turn changes the phase of the reflected signal in the optic cores 334, 324, and subsequently modifies the optical characteristics of the output signal detected. The output signal can be detected, for example, by a spectrometer, an optical spectrum analyzer, or a photo diode (not shown), which can be located within the handle 110.

According to some embodiments, the handle 110 may be equipped with a microcontroller or a microprocessor (not shown), configured to process the optical signal characteristics to produce a corresponding quantitative or qualitative measure of the applied pressure.

According to some embodiments, the sensing head 350 may be provided without a housing 352, such that the front cavity 358 is formed at the end of the second fiber core 334, surrounded by the second fiber cladding 336 and covered by a front diaphragm 362 (embodiments not shown). The diaphragm can be connected directly to the distal edges of the second fiber cladding 336 in such embodiments.

The continuous optic fiber 370 is generally similar to the optic fiber assembly 310, except that the continuous optic fiber 370 is formed from a continuous optic fiber instead of from two detachable sections. The continuous optic fiber 370 may extend from the handle 110 up to a fiber distal end 372, attached to a component of the delivery apparatus 102, such as an actuation member 172 or a support sleeve 180.

The continuous optic fiber 370 comprises a continuous optic core 374 surrounded by fiber cladding 376, and an axial sensing head 380 which is similar in structure and function to axial sensing head 350, for example having a front cavity 388 formed at the end of the optic core 374, surrounded by a housing 382 and covered by a front diaphragm 392 in a co-axial configuration.

In the embodiment illustrated in FIGS. 6A-6C, the continuous optic fiber 370 extends along the outer surface of the support tube 180, attached thereto such that the axial sensing head 380 is positioned proximal to the valve proximal end 122. The first optic fiber section 320 extends through an internal channel 176 formed within the actuation member 172, and at least a portion of the second optic fiber section 330 extends through a channel 170 formed within the inner member 154 all the way up to the inner member distal end 158. The channel 170 extends up to an inner member distal opening 168 at the inner member distal end 158, such that the front diaphragm 362 is at least flush with the inner member distal opening 168, or alternatively extends distally beyond the inner member distal opening 168.

The detachable optical coupling between the first optic fiber section 320 and the second optic fiber section 330, including the function and structure interface 344, are similar to the detachable optical coupling, including interface 244, shown and described above in conjunction with FIGS. 5A-5C, and are thus not described again herein.

Figure 6D:
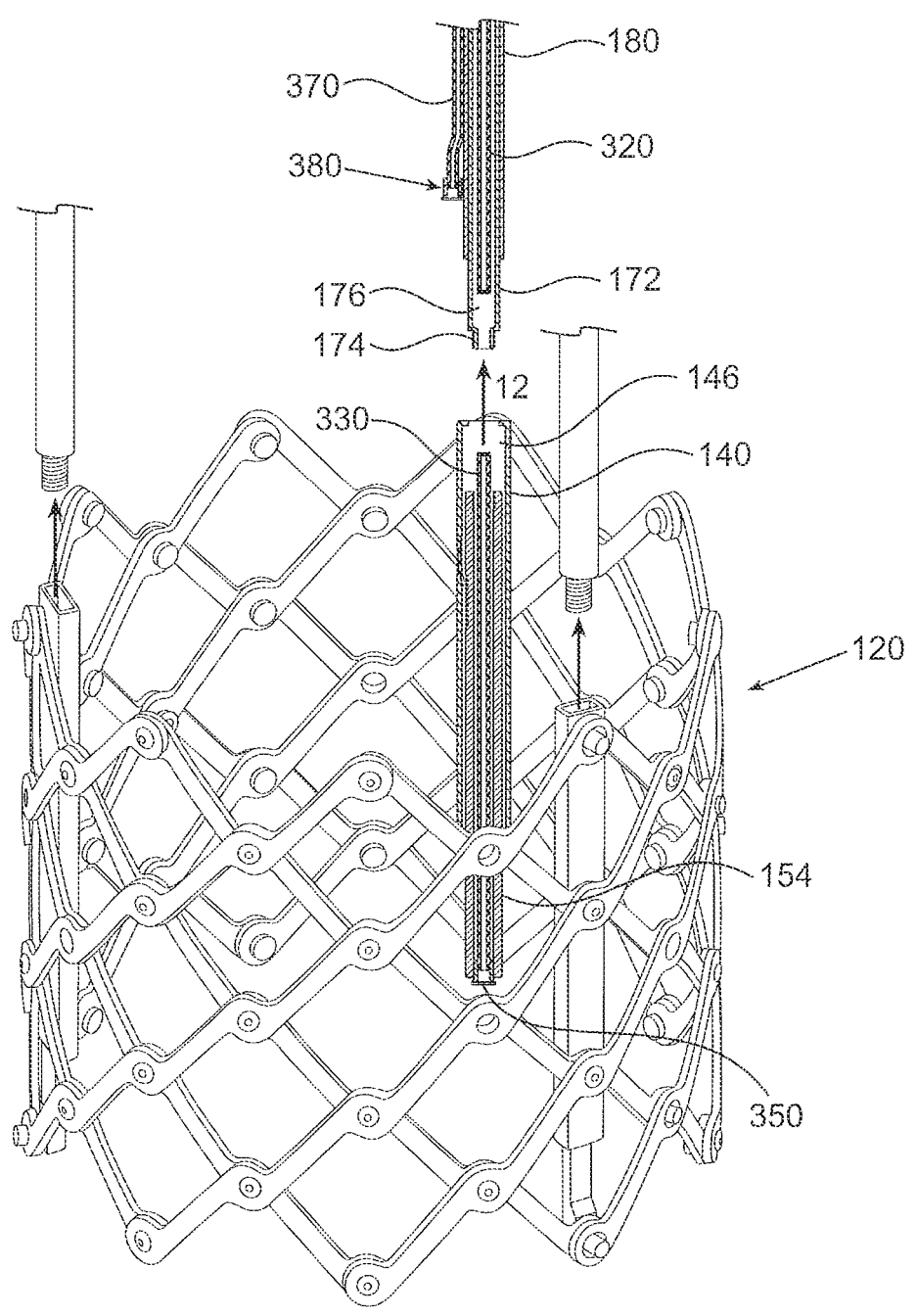

FIG. 6D shows the actuation member 172 disengaged from the actuator assembly 138, for example after being rotated around its longitudinal axis and pulled in a proximally oriented direction 12. In this state, both the continuous optic fiber 370 and the first optic fiber section 320, which are connected to the delivery apparatus 102, are pulled therewith, having the first optic fiber section 320 disconnected from the second optic fiber section 330, which remains connected to the valve 120, and more specifically, to the inner member 154.

In use, a delivery assembly 100 may be utilized to deliver a mechanically expandable prosthetic valve 120 toward a desired implantation site in a crimped state, having the continuous optic fiber 370 attached to the support sleeve 180, the actuation members 172 attached to the actuator assemblies 138 of the valve 120, and the first optic fiber section 320 optically coupled to the second optic fiber section 330.

Once the crimped valve 120 is positioned at the desired implantation site, the handle 110 may be maneuvered to pull the actuation members 172 to expand the valve 120. The axial Fabry-Perot pressure sensing heads 350 and 380 provide real-time feedback regarding the pressure levels sensed at the two axially-distanced locations, from which the pressure drop across the valve or pressure recovery can be derived. The feedback can be visually indicated, for example via a digital display 116 or LED lights 118 positioned at the handle 110. Such indication may assist the clinician in decision making regarding the next required steps of the implantation procedure, for example by repositioning or readjusting the valve's frame expansion, according to such measurements.

Once the valve 120 is expanded as desired and the real-time pressure readings are satisfactory, the handle 110 can be further maneuvered to rotate the actuation members 172 around their central axes, thereby optically decoupling the first and second optic fiber sections 320 and 330. Further rotation of the actuation members 172 serves to disengage them from the actuator assemblies 138, such that the delivery apparatus 102, including the support sleeve 180 with the continuous optic fiber 370 attached thereto, and the actuation members 172 with the first optic fiber section 320 attached thereto, can be retracted from the patient's body.

Although both the optic fiber assembly 310 and the continuous optic fiber 370 are shown in FIGS. 6A-6D extending along the same actuation arm assembly 171, having the optic fiber assembly 310 further extending along the actuation assembly 138 attached thereto, alternative configurations are acceptable. For example, the optic fiber assembly 310 may extend along one actuation arm assembly 171 and the actuation assembly 138 assembly attached thereto, while the continuous optic fiber 370 may extend along another actuation arm assembly 171 (alternative configuration not shown). Such a configuration may be feasible as pressure is substantially homogenous across the circumferential area at each axial position under ideal conditions.

Embodiments of a modified optic fiber assembly 410 and a modified continuous optic fiber 470 are illustrated in FIGS. 7A-7D, showing views similar to those of FIGS. 6A-6D, respectively. Optic fiber assembly 410 and continuous optic fiber 470 may be similar to optic fiber assembly 310 and continuous optic fiber 370, respectively, with the exceptions that the optic fiber assembly 410 comprises a lateral pressure sensing head 450 instead of an axial pressure sensing head 350, and the continuous optic fiber 470 comprises a lateral pressure sensing head 480 instead of an axial pressure sensing head 380. Each of the lateral pressure sensing heads 450 and 480 is configured to detect pressure applied to their respective side diaphragms 462 and 492 in a direction perpendicular to the longitudinal axis of optic cores 434 and 474, respectively.

Figure 7A:
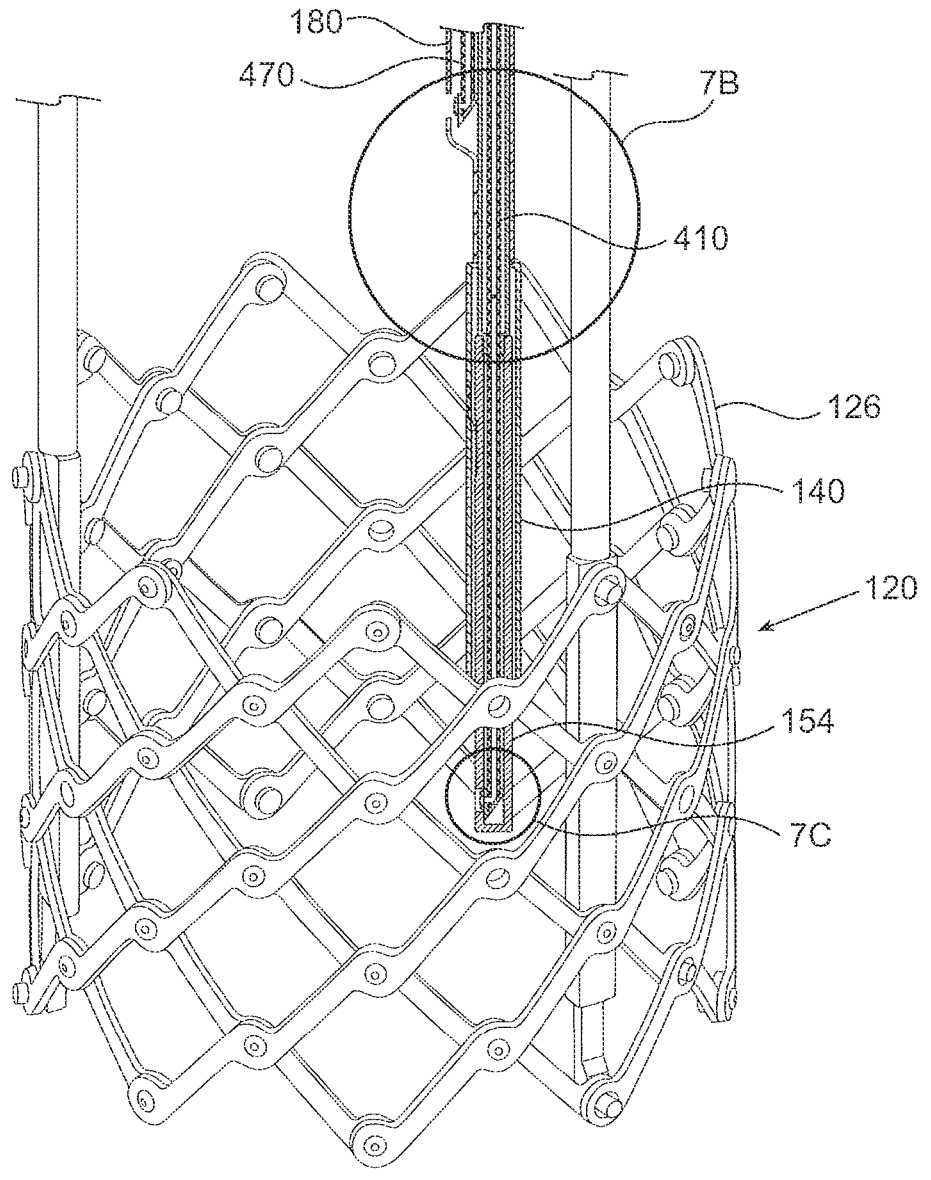
FIGS. 7A-7D show different views of a delivery assembly equipped with an optic fiber assembly and a continuous optic fiber, according to some embodiments.
Figure 7B:
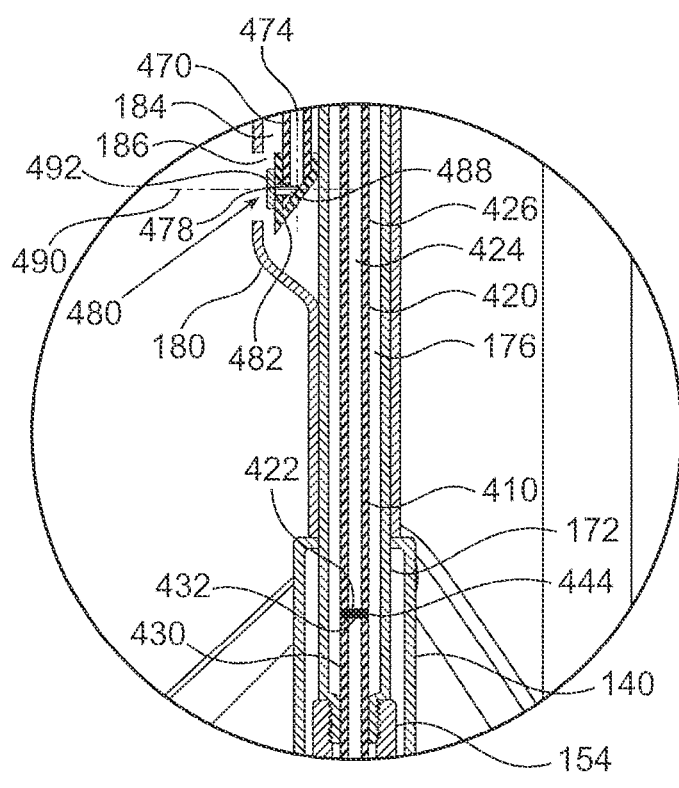
Figure 7C:
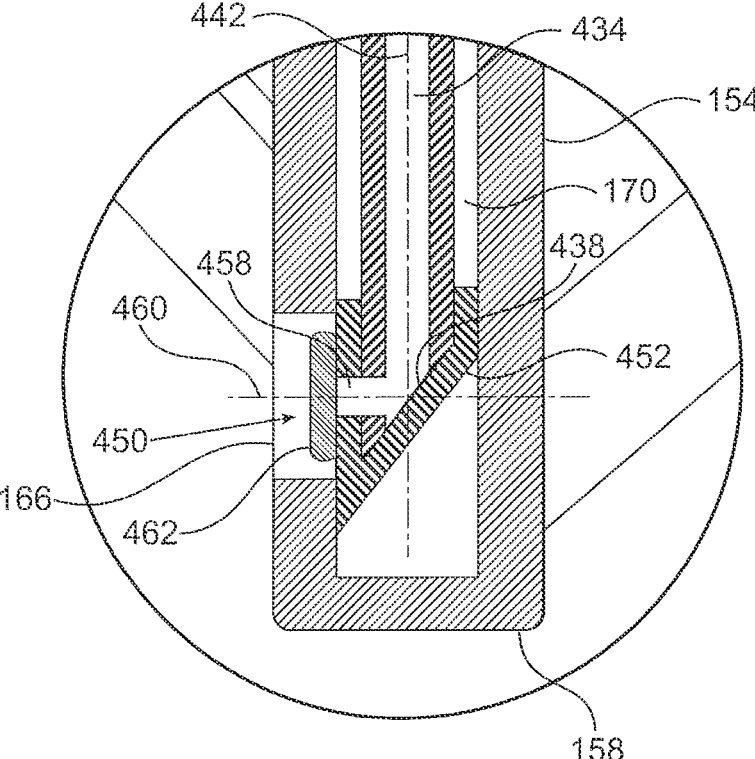

As shown in FIG. 7C, the second optic core 434 of the second optic fiber section 430 terminates at an inclined surface 438, which is angled relative to the optical axis 442 of the second optic core 434. An optical side cavity 458 extends through the second fiber cladding 436 and the housing 452, overlaid by a side diaphragm 462. In other words, the side cavity 458 extends between the second fiber inclined distal core surface 438 and the side diaphragm 462. According to some embodiments, the lateral pressure sensing head 450 is devoid of a housing 452, such that the optical side cavity 458 extends through the fiber cladding 436, and the side diaphragm 462 is attached to the outer surface of the fiber cladding 436, or any protective layer surrounding the cladding 436 if present (embodiments not shown).

The inclined surface 438 is preferably angled to provide a critical incidence angle for a light beam passing along the second optic core 434, in order to ensure a full reflection from the surface 438. Preferably, the inclined surface 438 is angled at a 45° angle relative to the optical axis 442.

However, it should be understood that other angles between the inclined surface 438 and the optical axis 442 may be applicable, as long as a critical incidence angle is provided for the light beam passing through the optic core 434.

As further shown in FIG. 7B, since the inclined surface 438 is angled relative to the optical axis 442, a light beam passing through second optic core 434 is redirected by 90° relative to the optical axis 442. When a redirected light beam impinges on the side diaphragm 462, it reflects and is returned to the inclined surface 438 to be redirected back through the optic fiber assemble 410, for example toward an input apparatus in the handle 110. Stated otherwise, the side diaphragm 462 and the side cavity 458 are cross-axially aligned with the second optic core 434.

When pressure is applied to the side diaphragm 462, the diaphragm 462 bends into the side cavity 458, thereby changing the path of the light beam, which changes the phase of the reflected signal.

The structure and function of the lateral pressure sensing head 480 at the distal end 472 of the continuous optic fiber 470, shown in FIG. 7C, is similar to that of lateral pressure sensing head 450 described above in conjunction with FIG. 7B, including the optic core 474 terminating at an inclined distal continuous core surface 478. Accordingly, description of these elements and their operation will not necessarily be repeated with respect to the embodiments presented and discussed in conjunction with FIGS. 7A-7D.

According to some embodiments, as illustrated in FIGS. 7A-7C, the continuous optic fiber 470 extends through a lumen 184 of the support sleeve 180, for example attached to the outer surface of the actuation member 172, such that the lateral sensing head 470 is positioned proximal to the outflow end 123. The support sleeve 180 comprises a support sleeve side opening 186 extending radially outwards from the support sleeve lumen 184 at a position such that the side diaphragm 492 of the continuous optic fiber's lateral pressure sensing head 480, is co-axially aligned with the support sleeve side opening 186 along its side cavity axis 490. The support sleeve side opening 186 is dimensioned so as to expose the side diaphragm 492 of the continuous optic fiber's lateral pressure sensing head 480 to the surrounding environment, such as the blood flow.

According to some embodiments, the side diaphragm 492 is flush with the outer surface of the support sleeve 180. According to alternative embodiments, the side diaphragm 492. can be positioned at a radially inward location relative to the outer surface of the support sleeve 180, or alternatively it may extend radially out of the support sleeve side opening 186.

The circumferential orientation of the continuous optic fiber's lateral pressure sensing head 480 is preferably chosen such that in use, its side diaphragm 492 will not be blocked by surrounding tissue, such as arterial walls. According to some embodiments, the continuous optic fiber's lateral pressure sensing head 480 is oriented such that its side diaphragm 492 faces away from the blood vessel wall or lateral to the blood vessel wall when in use. Such configurations may help, for example, to avoid interference between the side diaphragm 492 and portions of the native anatomy that would otherwise contact the continuous optic fiber's lateral pressure sensing head 480.

According to some embodiments, as further illustrated in FIGS. 7A-7C, the first optic fiber section 420 extends through the actuation member internal channel 176, and at least a portion of the second optic fiber section 430 extends through a channel 170 formed within the inner member 154.

As further shown, the inner member 154 comprises an inner member side opening 166 extending radially outwards from the inner member channel 170 at a position proximal to the inner member distal end 158. Thus, in such embodiments, contrary to the embodiments illustrated and described in conjunction with FIGS. 6A-6C, the channel 170 of the embodiment shown in FIGS. 7A-7C is not required to extend all the way up to the inner member distal end 158, but may rather terminate at a position proximal to the inner member distal end 158. While this is not a mandatory requirement in embodiments that include an inner member side opening 166, it will be clear that the inner member distal end 158 may still extend all the way to the inner member distal end 158 and terminate at an inner member distal opening 168.

According to some embodiments, the side diaphragm 462 is co-axially aligned with the inner member side opening 166 along its side cavity axis 460. The inner member side opening 166 is dimensioned so as to expose the side diaphragm 462 of the optic fiber assembly lateral pressure sensing head 450 to the surrounding environment, such as the blood flow.

According to some embodiments, the side diaphragm 462 of the optic fiber assembly lateral pressure sensing head 450 is flush with the outer surface of the inner member 154. According to alternative embodiments, the side diaphragm 462 of the optic fiber assembly lateral pressure sensing head 450 can be positioned at a radially inward location relative to the outer surface of the inner member 154, or alternatively it may extend radially out of the inner member side opening 166.

The circumferential orientation of the optic fiber assembly lateral pressure sensing head 450 is preferably chosen such that in use, its side diaphragm 462 will not be blocked by surrounding tissue such as arterial walls, or other components of the prosthetic valve 120 such as a skirt 136. According to some embodiments, the optic fiber assembly lateral pressure sensing head 450 is oriented such its side diaphragm 462 faces away from the blood vessel's wall when in use, and/or away from potentially blocking components of the prosthetic valve 120. According to some embodiments, the optic fiber assembly lateral pressure sensing head 450 is oriented such its side diaphragm 462 is facing radially inward toward a longitudinal axis 121, or substantially tangential to the circumference of the valve 120. Such configurations may help, for example, to avoid interference between the side diaphragm 462 and portions of the native anatomy that would otherwise contact the optic fiber assembly lateral pressure sensing head 450.

The lateral orientation of the lateral pressure sensing heads, such as the optic fiber assembly lateral pressure sensing head 450, advantageously allows positioning thereof at any desired measurement point along the axial path of the valve, which would be otherwise restricted to the inner member distal end 158 if an optic fiber assembly axial pressure sensing head 350 is utilized.

The detachable optical coupling between the first optic fiber section 420 and the second optic fiber section 430, including the function and structure interface 444, are similar to the detachable optical coupling, including interface 244, shown and described above in conjunction with FIGS. 5A-5C, and are thus not described again herein.

Figure 7D:
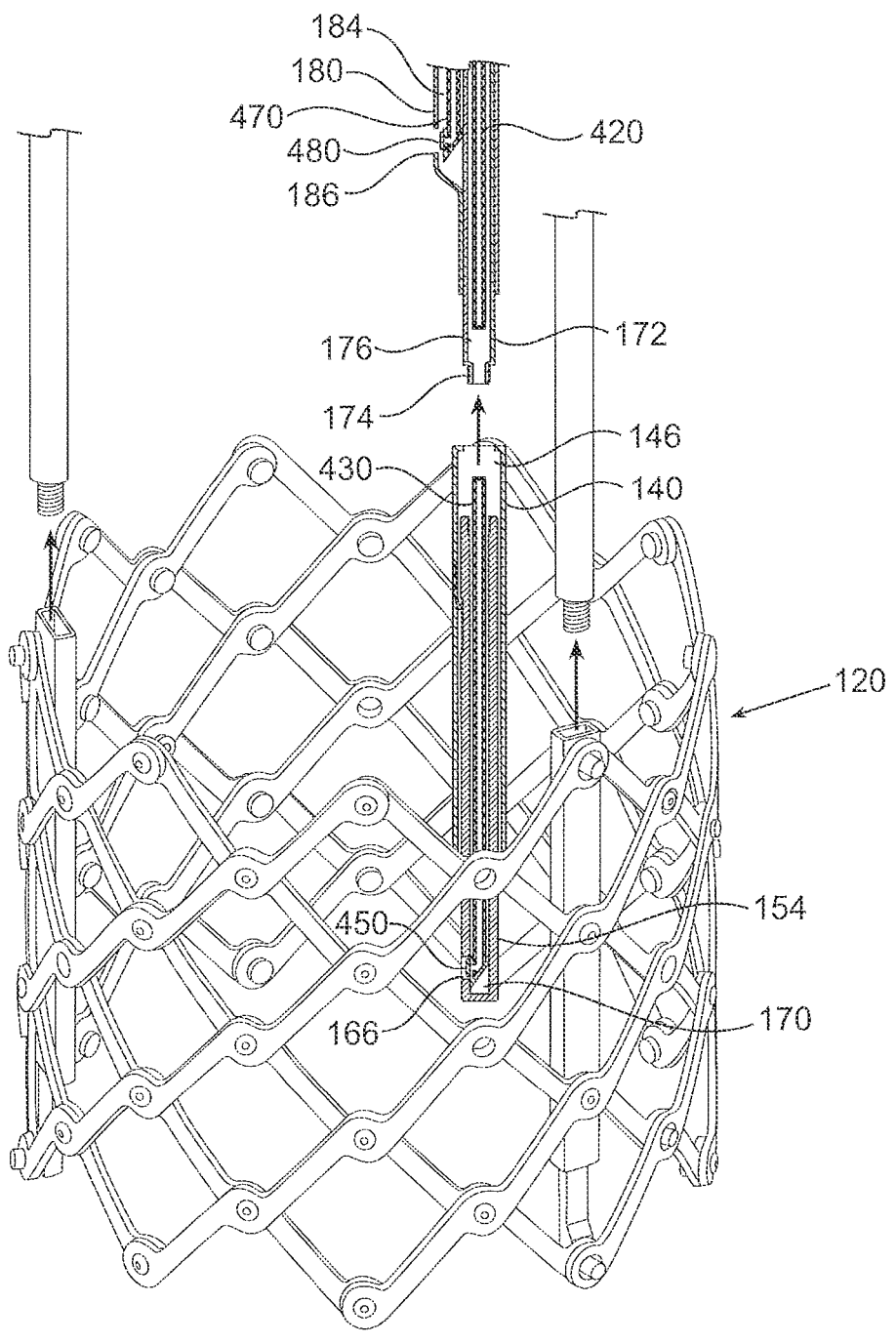

FIG. 7D shows the actuation member 172 disengaged from the actuator assembly 138, for example after being rotated around its longitudinal axis and pulled in a proximally oriented direction 12. In this state, both the continuous optic fiber 470 and the first optic fiber section 420, which are connected to the delivery apparatus 102, are pulled therewith, having the first optic fiber section 420 disconnected from the second optic fiber section 430, which remains connected to the valve 120, and more specifically, to the inner member 154.

In use, a delivery assembly 100 may be utilized to deliver a mechanically expandable prosthetic valve 120 toward a desired implantation site in a crimped state, having the continuous optic fiber 470 attached to the delivery apparatus and extending through a support sleeve lumen 184 such that the side diaphragm is co-axially aligned with the support sleeve side opening 186. The actuation members 172 are attached to the actuator assemblies 138 of the valve 120, and the first optic fiber section 420 is optically coupled to the second optic fiber section 430.

Once the crimped valve 120 is positioned at the desired implantation site, the handle 110 may be maneuvered to pull the actuation members 172 to expand the valve 120. The lateral Fabry-Perot pressure sensing heads 450 and 480 provide real-time feedback regarding the pressure levels sensed at the two axially-distanced locations, from which the pressure drop across the valve or pressure recovery can be derived. The feedback can be visually indicated, for example via a digital display 116 or LED lights 118 positioned at the handle 110. Such indication may assist the clinician in decision making regarding the next required steps of the implantation procedure, for example by repositioning or readjusting the valve's frame expansion, according to such measurements.

Once the valve 120 is expanded as desired and the pressure readings are satisfactory, the handle 110 can be further maneuvered to rotate the actuation members 172 around their central axes, thereby optically decoupling the first and second optic fiber sections 420 and 430. Further rotation of the actuation members 172 serves to disengage them from the actuator assemblies 138, such that the delivery apparatus 102, including the support sleeve 180 with the continuous optic fiber 470 attached thereto, and the actuation members 172 with the first optic fiber section 420 attached thereto, can be retracted from the patient's body.

Although both the optic fiber assembly 410 and the continuous optic fiber 470 are shown in FIGS. 7A-7D extending along the same actuation arm assembly 171, having the optic fiber assembly 410 further extending along the actuation assembly 138 attached thereto, alternative configurations may include an optic fiber assembly 410 extending along one actuation arm assembly 171 and the actuation assembly 138 assembly attached thereto, while the continuous optic fiber 470 extends along another actuation arm assembly 171 (alternative configuration not shown). As stated above in relation with FIGS. 6A-6D, such configurations may be feasible as pressure is substantially homogenous across the circumferential area at each axial position under ideal conditions.

According to some embodiments, although not shown explicitly, the continuous optic fiber 470 may extend through an internal channel 176 formed within the actuation member 172 instead of being attached to the external surface of the actuation member 172, such that the lateral sensing head 470 is positioned proximal to the valve's outflow end 123. In such embodiments (not shown), the actuation member 172 comprises an actuation member side opening (similar to side openings 178 shown in FIG. 11B) extending radially outward from the actuation member internal channel 176, and the support sleeve 180 comprises a corresponding support sleeve side opening (similar to side openings 186 shown in FIG. 11B) extending radially outward, at a position such that the side diaphragm 492 of the continuous optic fiber's lateral pressure sensing head 480 is co-axially aligned with both the actuation member side opening 178 and the support sleeve side opening 186 along its side cavity axis 490. The actuation member side opening 178 and the support sleeve side opening 186 are dimensioned so as to expose the side diaphragm 492 of the continuous optic fiber's lateral pressure sensing head 480 to the surrounding environment, such as the blood flow.

Reference is now made to FIGS. 8A-8D, showing further embodiments of a delivery assembly 100 equipped with a mechanically expandable valve 120, having at least one multi-core optic fiber assembly 510 extending through the delivery apparatus 102 and attached at its distal portion to the frame 126. In some instances, the optic fiber assembly 510 can extend from the handle 110, through or along an actuation arm assembly 171 toward the actuator assembly 138, having its distal portion attached to a component of the actuator assembly 138, such as the inner member 154.

Figure 8A:
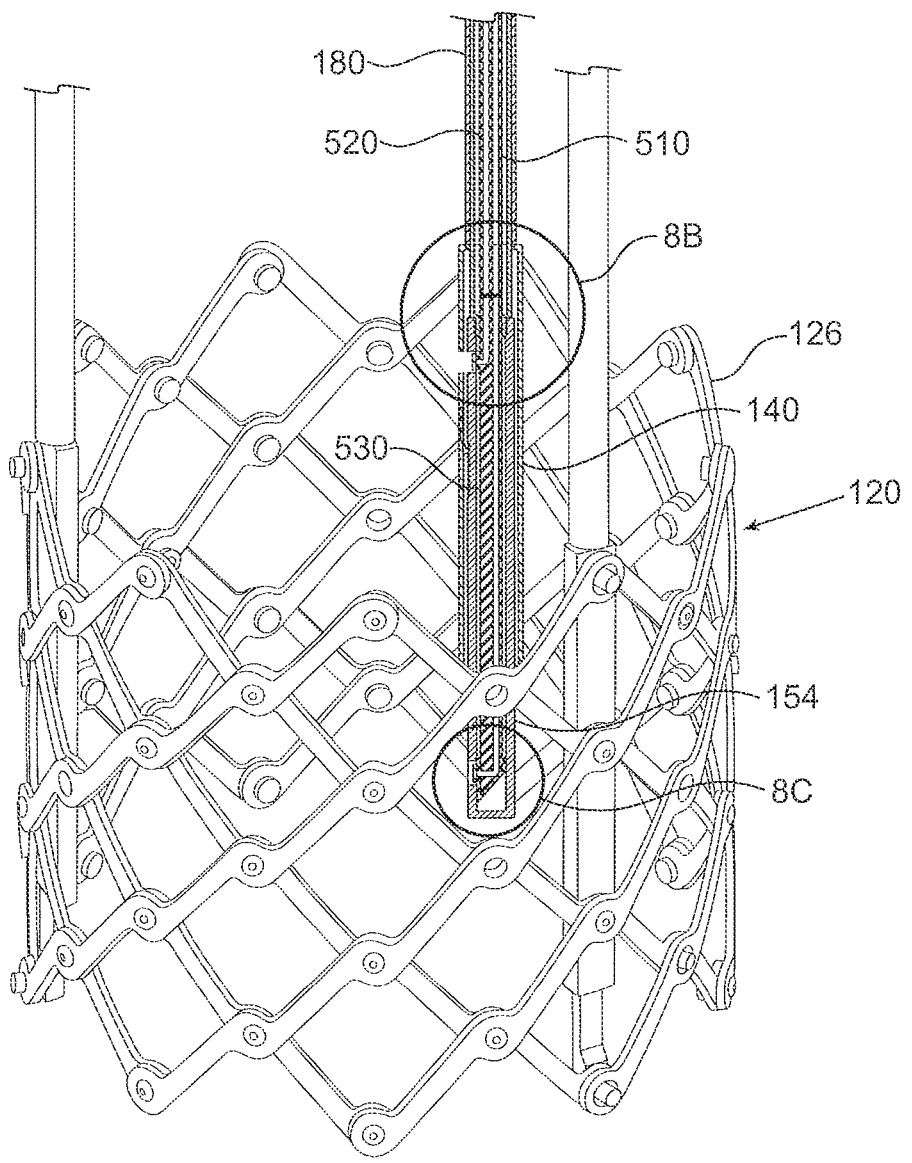
FIGS. 8A-8D show different views of a delivery assembly equipped with a multi-core optic fiber assembly, according to some embodiments.
Figures 8B, 8C:
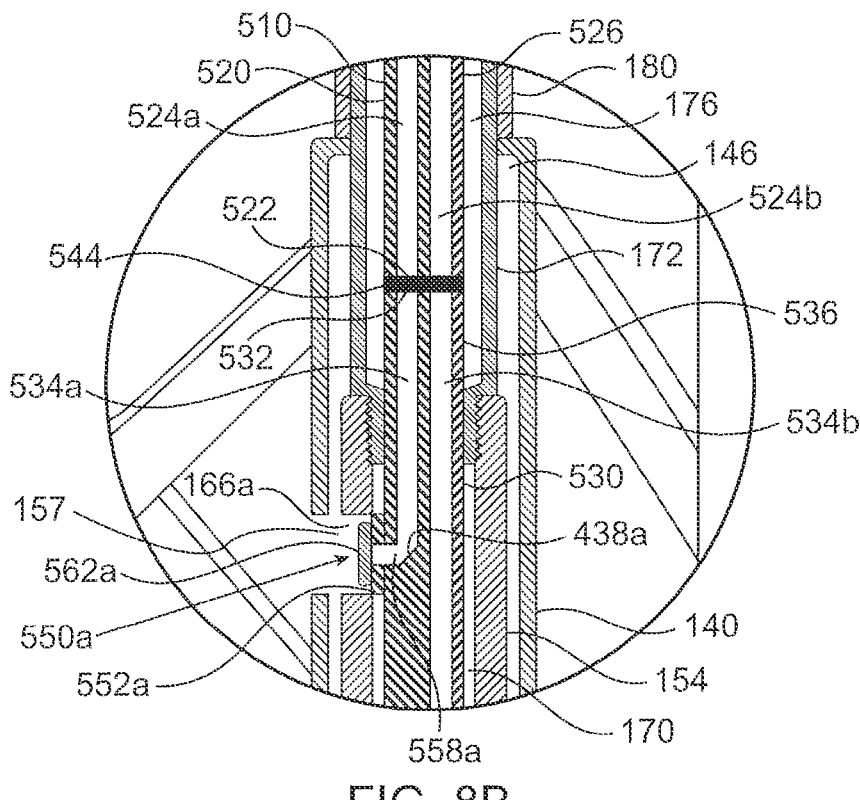

FIG. 8A shows a view in perspective of a mechanically expandable valve 120 having its actuation assemblies 138 connected to actuation members 172, wherein a fiber optic assembly 510 extends through an actuation member 172 toward the inner member 154. FIG. 8B shows a zoomed in view of region 8B in FIG. 8A. FIG. 8C shows a zoomed in view of region 8C in FIG. 8A.

According to some embodiments, any optic fiber of the current disclosure, including any previous embodiments of optic fiber assemblies or continuous optic fibers, can include a plurality of internal cores, surrounded by the optic fiber cladding. Each optic core may include, or be attached to, a separate pressure sensing head at its distal end. Thus, a multi-core optic fiber can advantageously enable pressure measurements along a plurality of axially-spaced measurement points, dictated by different axial positions of the sensing heads, provided on a single optic fiber.

Multi-core optic fiber assembly 510 is generally similar in structure to fiber optic assembly 410, with the exception that each of the first and second optic fiber sections 520 and 530, comprises a plurality of optic cores 524 and 534, respectively, and a plurality of lateral pressure sensing heads 550 at the end of respective second optic cores 534.

The exemplary multi-core fiber optic assembly 510 shown in FIGS. 8A-8C includes two first optic cores 524a and 524b surrounded by the first fiber cladding 526, and two second optic cores 534a and 534b surrounded by the second fiber cladding 536. The structure and function of the lateral pressure sensing head 550a at the distal end of second optic core 534a, and the lateral pressure sensing head 550b at the distal end of second optic core 534b, are similar to those of lateral pressure sensing head 450 described in conjunction with FIG. 7B above, including the second optic cores 534a and 534b terminating at inclined surfaces 538a and 538b, respectively. Accordingly, description of these elements and their operation will not necessarily be repeated with respect to the embodiments presented and discussed in conjunction with FIGS. 8A-8C.

According to some embodiments, the plurality of lateral pressure sensing heads 550 are axially spaced from each other, to provide pressure measurements at different axial positions along the second optic fiber section 530. In the exemplary embodiment of FIGS. 8A-8C, the lateral pressure sensing head 550a is closer to the valve outflow end 123 than the lateral pressure sensing head 550b. In other words, the lateral pressure sensing head 550a is positioned proximal to the lateral pressure sensing head 550b. According to some embodiments, one lateral pressure sensing head 550a may be positioned in the region of the outflow end portion 122 of the prosthetic valve 120, while another lateral pressure sensing head 550b may be positioned in the region of the inflow end portion 124, such that pressure difference across the valve 120 may be calculated.

According to some embodiments, as illustrated in FIGS. 8A-8D, the first optic fiber section 520 extends through an actuation member internal channel 176, and at least a portion of the second optic fiber section 530 extends through an inner member internal channel 170.

According to some embodiments, the inner member 154 comprises a plurality of inner member side openings 166 each extending radially outwards from the inner member channel 170, the plurality member side openings 166 being axially spaced from each other. In the exemplary embodiment of FIGS. 8A-8D, the inner member 154 comprises two side openings 166a and 166b, wherein the side diaphragm 562a of the optic fiber assembly lateral pressure sensing head 550a is co-axially aligned with the inner member side opening 166a along its side cavity axis 560a, and wherein the side diaphragm 562b of the optic fiber assembly lateral pressure sensing head 550b is co-axially aligned with the inner member side opening 166b along its side cavity axis 560b. The housing 140 may also include at least one outer member side opening 157 extending radially outwards from the outer member lumen 146 at a position such that the side diaphragm 562a pressure sensing head 450a at the outflow end portion 122, is co-axially aligned with inner member side opening 166a and the outer member side opening 157.

The dimensions of each of the plurality of inner member side openings 166, the relative position of each optic fiber assembly lateral pressure sensing heads 550 relative to its respective side opening 166, and the circumferential orientation of each optic fiber assembly lateral pressure sensing head 550, are similar to those illustrated and described above for inner member side opening 166 and optic fiber assembly lateral pressure sensing head 450 in conjunction with FIGS. 7A-C, and are thus not described again herein.

According to some embodiments, the outer member side opening 157 is dimensioned so as to expose the side diaphragm 562a to the surrounding environment, such as the blood flow. In cases in which the inner member 154 is axially movable relative to the outer member 140, the axial position of the pressure sensing head 450a may change during valve expansion or compression. In such cases, it is desirable that the outer member side opening 157 will be formed and dimensioned so as to allow exposure of the side diaphragm 562a to the surrounding environment during the entire working range of the prosthetic valve 120, preferably between a fully compressed state and a fully expanded state of the valve. According to some embodiments, the outer member side opening 157 is a longitudinal slot, having an axial length suitable to expose the side diaphragm 562a, optionally through an inner member side opening 166a, to the surrounding environment along an axial path range of the pressure sensing head 450a between compressed and expanded states of the prosthetic valve 120. In such embodiments, the width of the outer member side opening 157 may be substantially equal to the width of the inner member side opening 166a, while the axial length of the outer member side opening 157 may be longer than the axial length of the inner member side opening 166a.

The detachable optical coupling between the first optic fiber section 520 and the second optic fiber section 530, including the function and structure of interface 544, are similar to the detachable optical coupling, including interface 244, shown and described above in conjunction with FIGS. 5A-5C, and are thus not described again herein except with regard to the differences between optically coupling single-core optic fiber segments and multiple-core optic fiber segments. In this regard, a PC connection between the first optic fiber section 520 and the second optic fiber section 530 may be realized by aligning each of the first optic cores 524 with the respective second optic cores 534. For example, aligning first optic core 524a with second optic core 534a, aligning first optic core 524b with second optic core 534b, and so on.

Figure 8D:
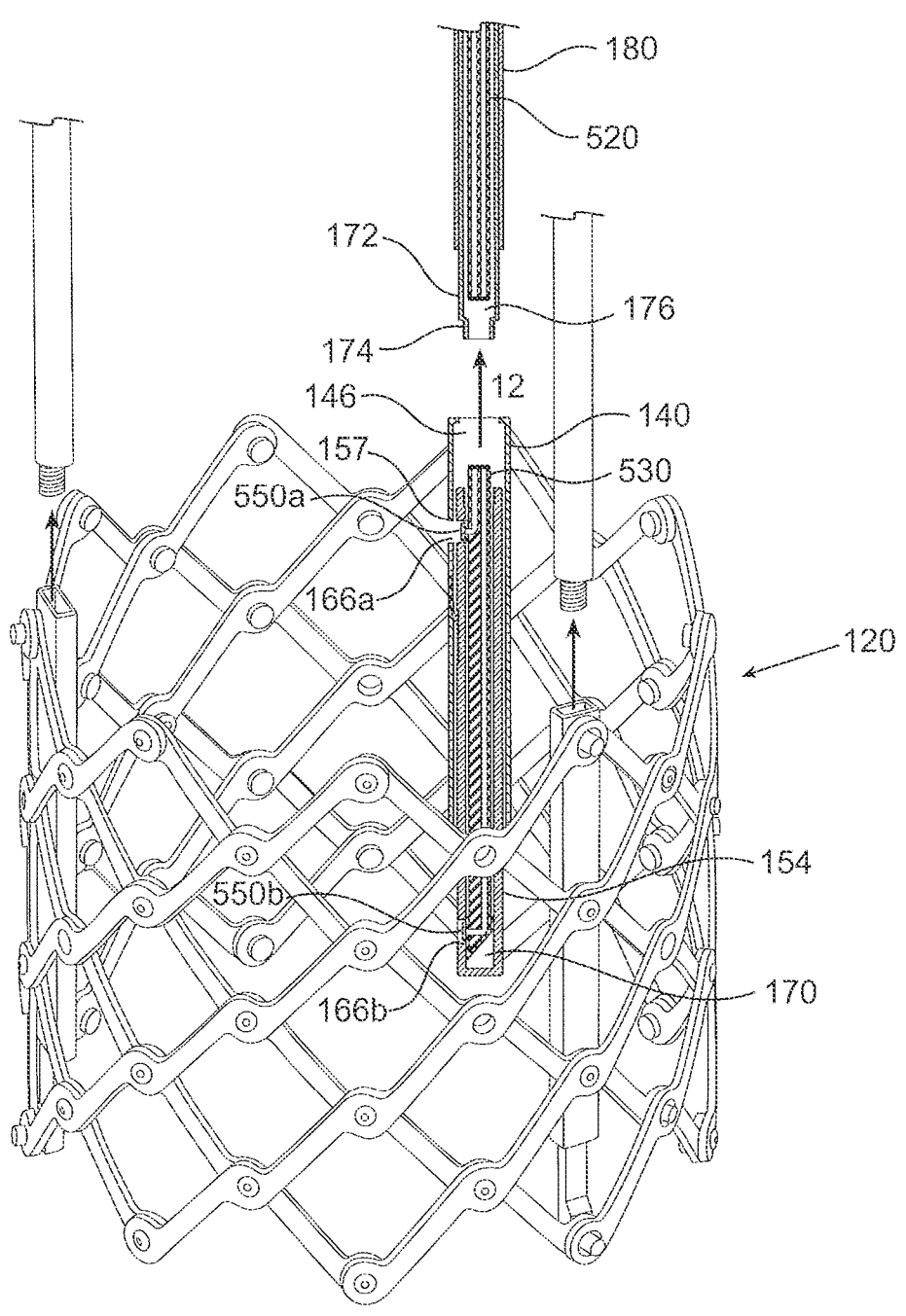

FIG. 8D shows the actuation member 172 disengaged from the actuator assembly 138, for example after being rotated around its longitudinal axis and pulled in a proximally oriented direction 12. In this state, the first optic fiber section 520, which is connected to the delivery apparatus 102, is pulled therewith after being disconnected from the second optic fiber section 530, which remains connected to the valve 120, and more specifically, to the inner member 154.

Although two cores with two corresponding optic fiber assembly lateral pressure sensing heads 550 are shown in FIGS. 8A-8D, the number of cores and respective optic fiber assembly lateral pressure sensing heads 550 may be higher than two. Advantageously, utilization of a plurality of pressure sensing heads along the valve's flow path provides a higher resolution due to a larger number of measurement points, thereby enabling to derive more accurate pressure recovery profiles.

FIGS. 8A-8D show one embodiment of a multi-core fiber optic assembly 510 equipped with a plurality of lateral pressure sensing heads 550. According to alternative or additional embodiments, although not shown explicitly, a multi-core fiber optic assembly 510 may comprise at least one axial pressure sensing head and at least one lateral pressure sensing head 550. The at least one axial pressure sensing head is similar in structure and function to the axial pressure sensing head 350 described above, and is attached to or formed at the distal end of one of the second optic cores 534, such that the axial pressure sensing head is located at the second fiber distal end 540. The at least one lateral pressure sensing heads 550 is thereby positioned proximal to the axial pressure sensing head.

In such embodiments, the inner member 154 comprises both an inner member distal opening 168, and at least one side opening 166, such that the front diaphragm of the axial pressure sensing head is either flush with the inner member distal opening 168 or extending distally therefrom, and each side diaphragm 560 of a lateral pressure sensing heads 550 is co-axially aligned with a corresponding inner member side opening 166 and potentially with or along the axial length of an outer member side opening 157.

According to some embodiments, a plurality of axially spaced pressure sensor heads are attached to the delivery apparatus 102, such that each of the pressure sensor heads is proximal to the valve's outflow portion 122. According to some embodiments, a plurality of axially spaced pressure sensor heads are attached to at least one actuation arm assembly 171. According to some embodiments, a plurality of continuous optic fibers, each equipped with at least one pressure sensing head, are attached to at least one actuation arm assembly 171. According to some embodiments, at least one multi-core continuous optic fiber, equipped with a plurality of axially spaced pressure heads, is attached to at least one actuation arm assembly 171.

Figure 9A:
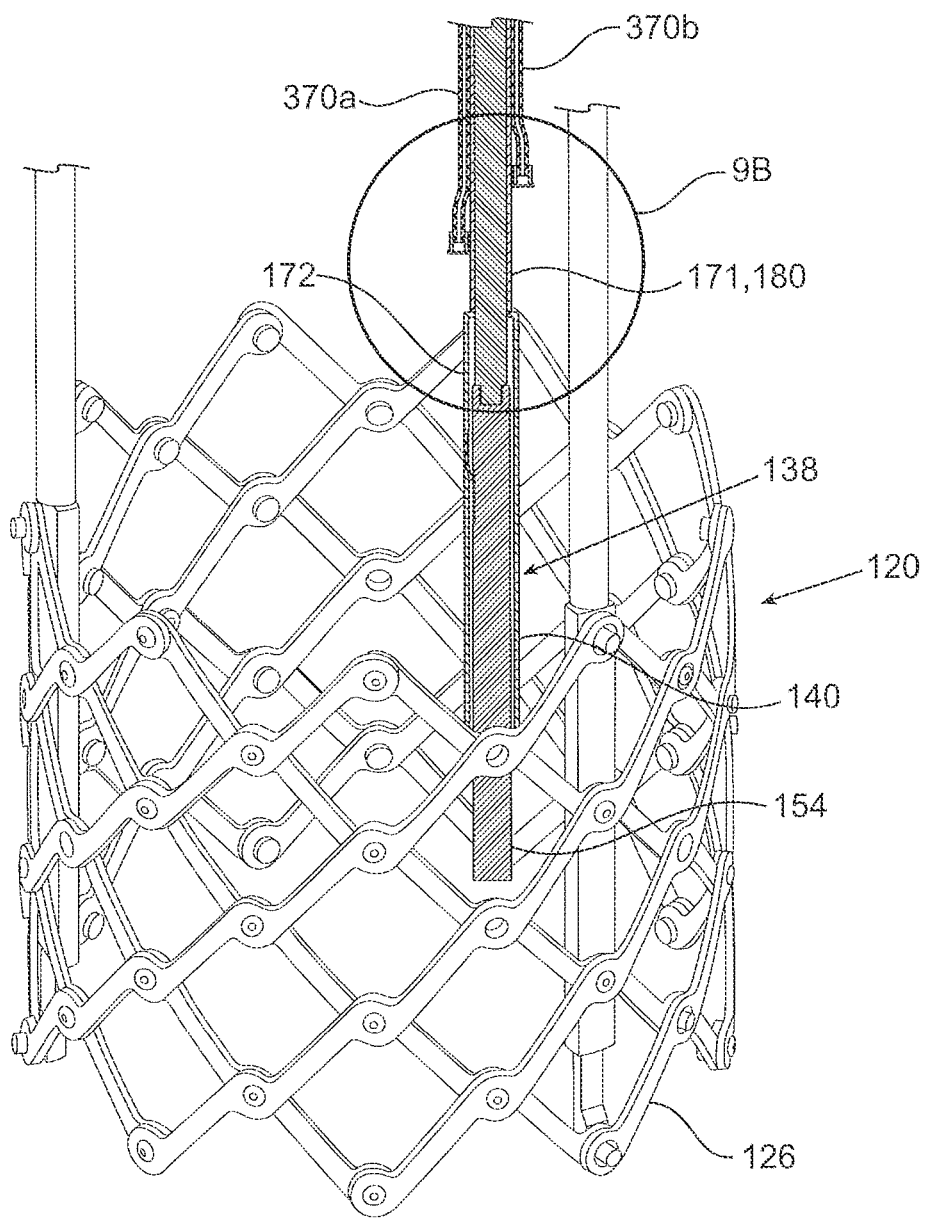
FIGS. 9A-9C show different views of a delivery assembly equipped with a plurality of continuous optic fibers, according to some embodiments.
Figure 9B:
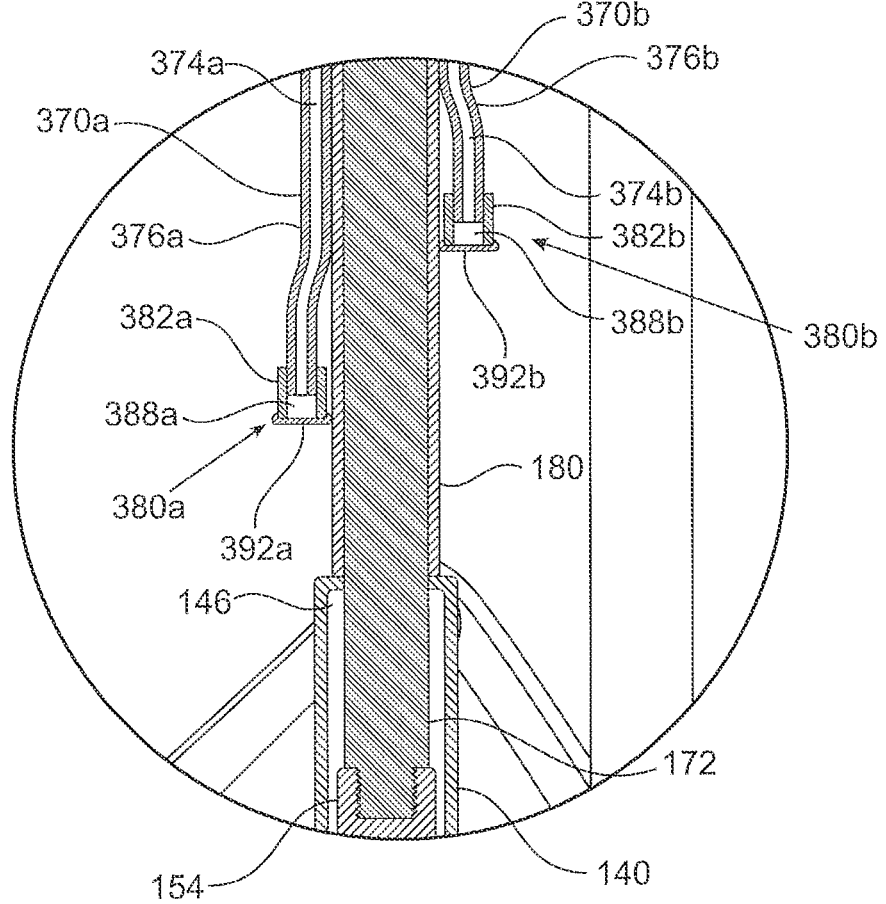
Figure 9C:
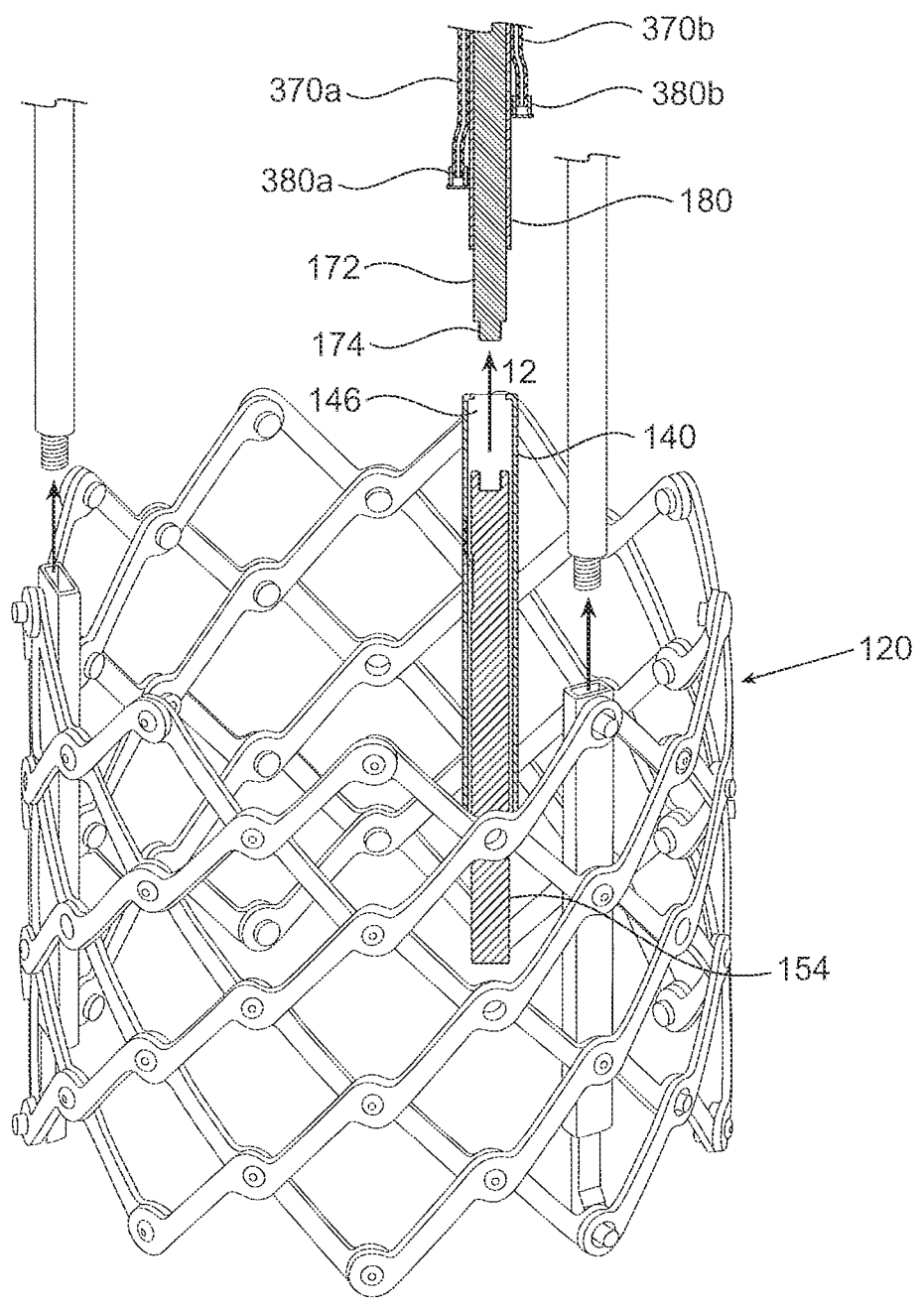

An exemplary configuration of attaching continuous optic fibers to a delivery apparatus 102 is shown in FIGS. 9A-9C. According to some embodiments, a plurality of continuous optic fibers 370 are attached to at least one component of the delivery apparatus 102, such as at least one actuation arm assembly 171. According to some embodiments, a plurality of continuous optic fibers 370 are attached to a support sleeve 180. FIG. 9A shows a view in perspective of a mechanically expandable valve 120 having its actuation assemblies 138 connected to actuation members 172, wherein two continuous optic fibers 370a and 370b are attached to, and extending along, the support sleeve 180. FIG. 9B shows a zoomed-in view of region 9B in FIG. 9A.

The plurality of axial pressure sensing heads 380 are axially spaced from each other, to provide pressure measurements at different axial positions along the support sleeve 180. In the exemplary embodiment of FIGS. 9A-9B, the axial pressure sensing head 380a is axially closer to the valve outflow end portion 122, that is to say that the position of the axial pressure sensing head 380a is distal to the position of axial pressure sensing head 380b. Preferably, at least one of the plurality of pressure sensing heads 380 is positioned in a relative close proximity to the valve's outflow end 123. For example, the most distal axial pressure sensing head 380a can be positioned at or in close proximity to the support member distal lip 182.

According to some embodiments, as shown in the arrangement exemplified in FIGS. 9A-9B, the delivery assembly 100 does not include optic fiber assemblies attached to the valve 120. Rather, according to some embodiments, the delivery assembly 100 comprises a plurality of continuous optic fibers attached to the delivery apparatus 102, for example to at least one actuation arm assembly 171. Such configurations rely on an assumption that the pressure at the inflow region of the valve 120, which is not measured directly in the absence of an optic fiber assembly attached to the valve 120, can be mathematically extrapolated from the pressure readings received from the plurality of the pressure sensing heads proximal to the valve 120, in order to derive an estimated complete pressure recovery profile across the valve 120.

Although both continuous optic fibers 370a and 370b, and specifically both axial pressure sensing heads 380a and 380b, are illustrated in FIGS. 9A-9B attached to the support sleeve 180 at diametrically opposing positions, it will be understood that any other relative circumferential positions are applicable across the circumference of the actuation arm assembly 171.

FIG. 9C shows the actuation member 172 and its support sleeve 180 disengaged from the actuator assembly 138, for example after being rotated around its longitudinal axis and pulled in a proximally oriented direction 12. In this state, all of the continuous optic fibers 370 are pulled therewith, while the valve 120 remains at the implantation site without having any excessive components attached thereto.

Although two continuous optic fibers 370 are shown in FIGS. 9A-9C, the number of continuous optic fibers 370 may vary. Advantageously, utilization of a plurality of pressure sensing heads along the valve's flow path provides a higher resolution due to a larger number of measurement points, thereby enabling to derive more accurate pressure recovery profiles.

While both of the continuous optic fibers 370a and 370b shown in FIGS. 9A-9C extend along the same support sleeve 180, alternative or additional configurations may include at least one continuous optic fiber 370a extending along one support sleeve 180, and at least one other continuous optic fibers 370b extending along a different support sleeve 180 (alternative configuration not shown). Such a configuration may be feasible as pressure is substantially homogenous across the circumferential area at each axial point under ideal conditions.

Additional optional configurations may include at least one continuous optic fiber 370 extending along one support sleeve 180, and a plurality of other continuous optic fibers 370 extending along another support sleeve 180 (configurations not shown).

Figure 10A:
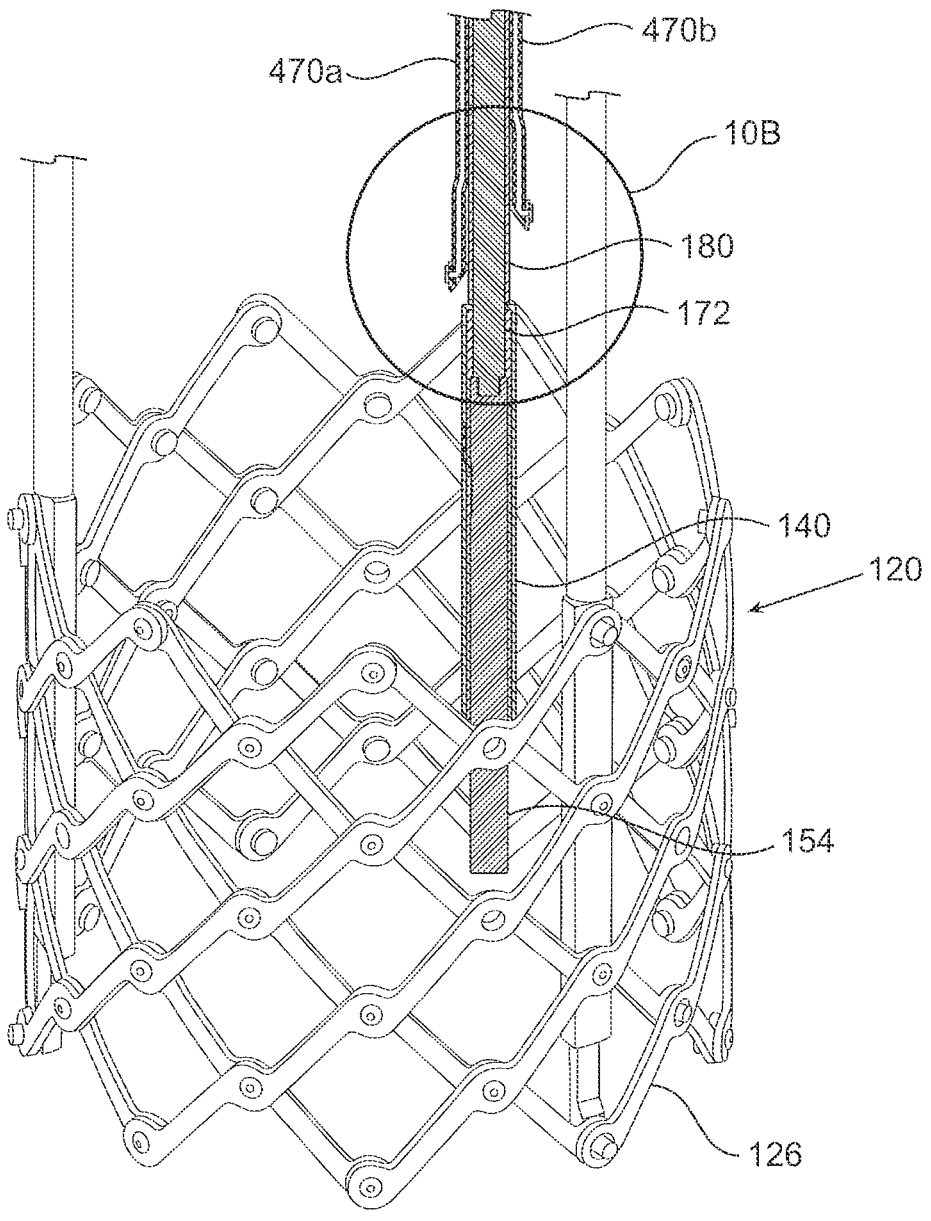
FIGS. 10A-10C show different views of a delivery assembly equipped with a plurality of continuous optic fibers, according to some embodiments.
Figure 10B:
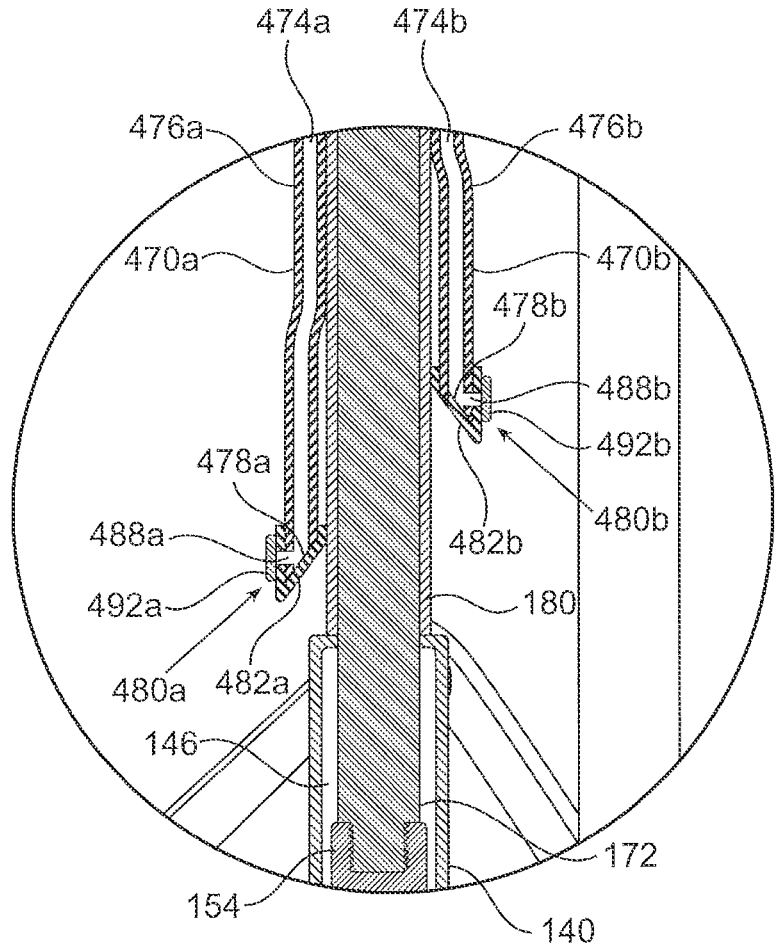
Figure 10C:
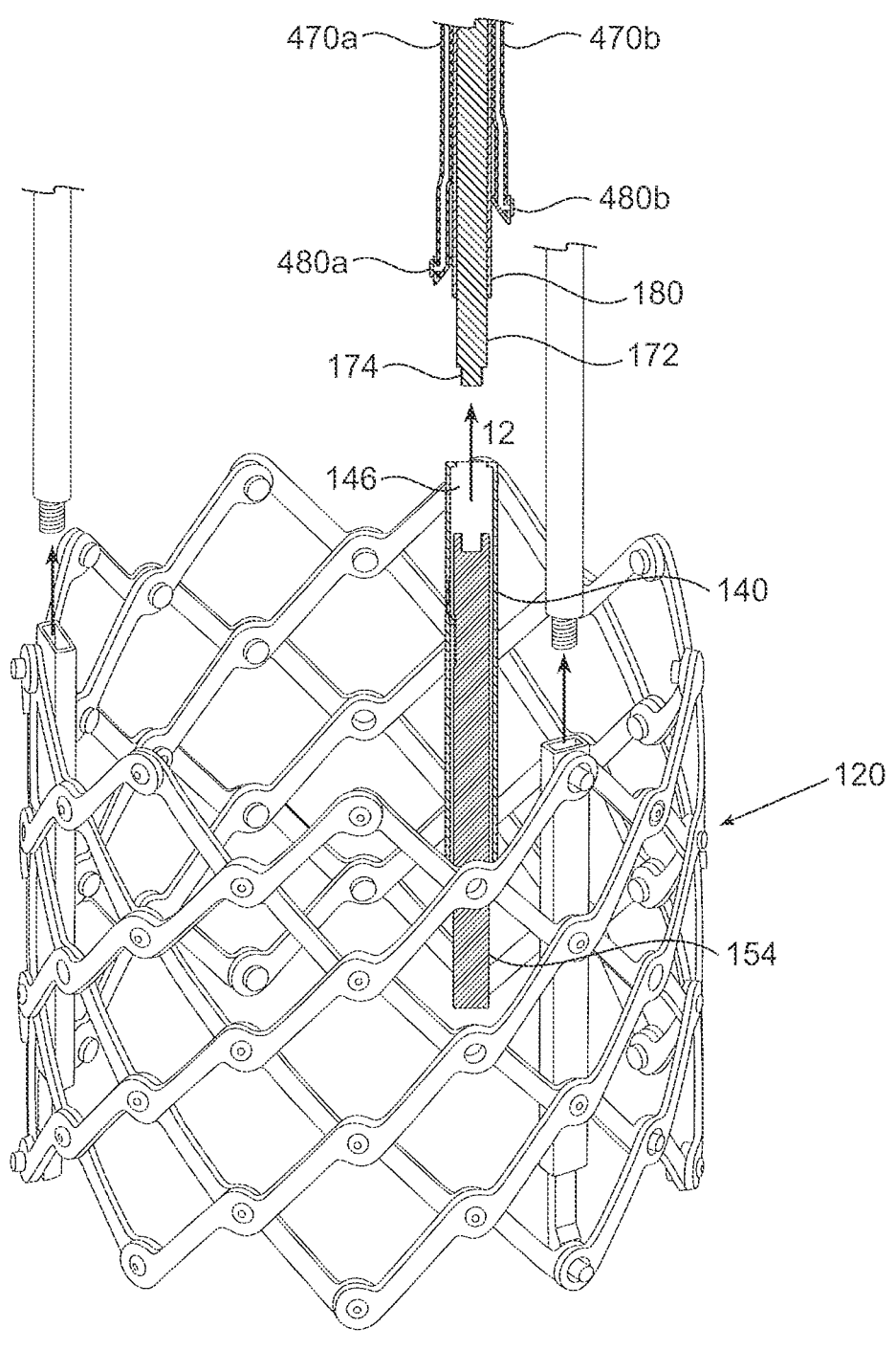

An additional configuration of attaching continuous optic fibers to a delivery apparatus 102 is shown in FIGS. 10A-10C. The configuration shown in FIGS. 10A-10C is similar to that shown in FIGS. 9A-9C, except that a plurality of continuous optic fibers 470 are equipped with axially spaced lateral pressure sensing heads 480. In this configuration, the continuous optic fibers 470 are attached to at least one actuation arm assembly 171, for example to at least one support sleeve 180. FIG. 10A shows a view in perspective of a mechanically expandable valve 120 having its actuation assemblies 138 connected to actuation members 172, wherein two continuous optic fibers 470a and 470b are attached to, and extending along, a support sleeve 180. FIG. 10B shows a zoomed in view of region 10B in FIG. 10A.

The plurality of lateral pressure sensing heads 480 are axially spaced from each other, to provide pressure measurements at different axial positions along the support sleeve 180. In the exemplary embodiment of FIGS. 10A-10B, the position of the axial pressure sensing head 480a is distal to the position of axial pressure sensing head 480b. The general consideration regarding axial and/or lateral positions described in connection with the plurality of axial pressure sensing heads 380 similarly apply to the plurality of lateral pressure sensing heads 480.

FIG. 10C shows the actuation member 172 and its support sleeve 180 disengaged from the actuator assembly 138, for example after being rotated around its longitudinal axis and pulled in a proximally oriented direction 12. In this state, all of the continuous optic fibers 470 are pulled therewith, while the valve 120 remains at the implantation site without having any excessive components attached thereto, exhibiting the same advantage as described above for the configuration of the plurality of continuous optic fibers 370 attached to the support sleeve 180.

According to some embodiments, although not explicitly shown, a plurality of continuous optic fibers 470 equipped with axially spaced lateral pressure sensing heads 480 are attached to an actuation member 172 instead of to a support sleeve 180. The general considerations regarding arrangement and positioning of the continuous optic fibers 470 and the axially spaced lateral pressure sensing heads 480, when attached to an actuation member 172, are similar to those described above for the same components when attached to a support member 180.

According to some embodiments, a plurality of continuous optic fibers 470 may extend through the support sleeve lumen 184, for example attached to the outer surface of the actuation member 172. In such embodiments, the support sleeve 180 may include a plurality of support sleeve side openings 186, wherein each support sleeve side opening 186 is aligned with a respective lateral pressure sensing head 480, and is dimensioned so as to expose the corresponding side diaphragm 492 to the surrounding environment, such as the blood flow.

According to yet other embodiments, a plurality of continuous optic fibers 470 may extend through an actuation member channel 176. The actuation member 172 may include a plurality of actuation member side openings 178, and the support sleeve 180 may include a plurality of support sleeve side openings 186, such that each support sleeve side opening 186 is aligned with both a respective actuation member side opening 178 and a lateral pressure sensing head 480. The support sleeve side openings 186 and the actuation member side openings 178 are dimensioned so as to expose the corresponding side diaphragms 492 to the surrounding environment, such as the blood flow.

Figure 11A:
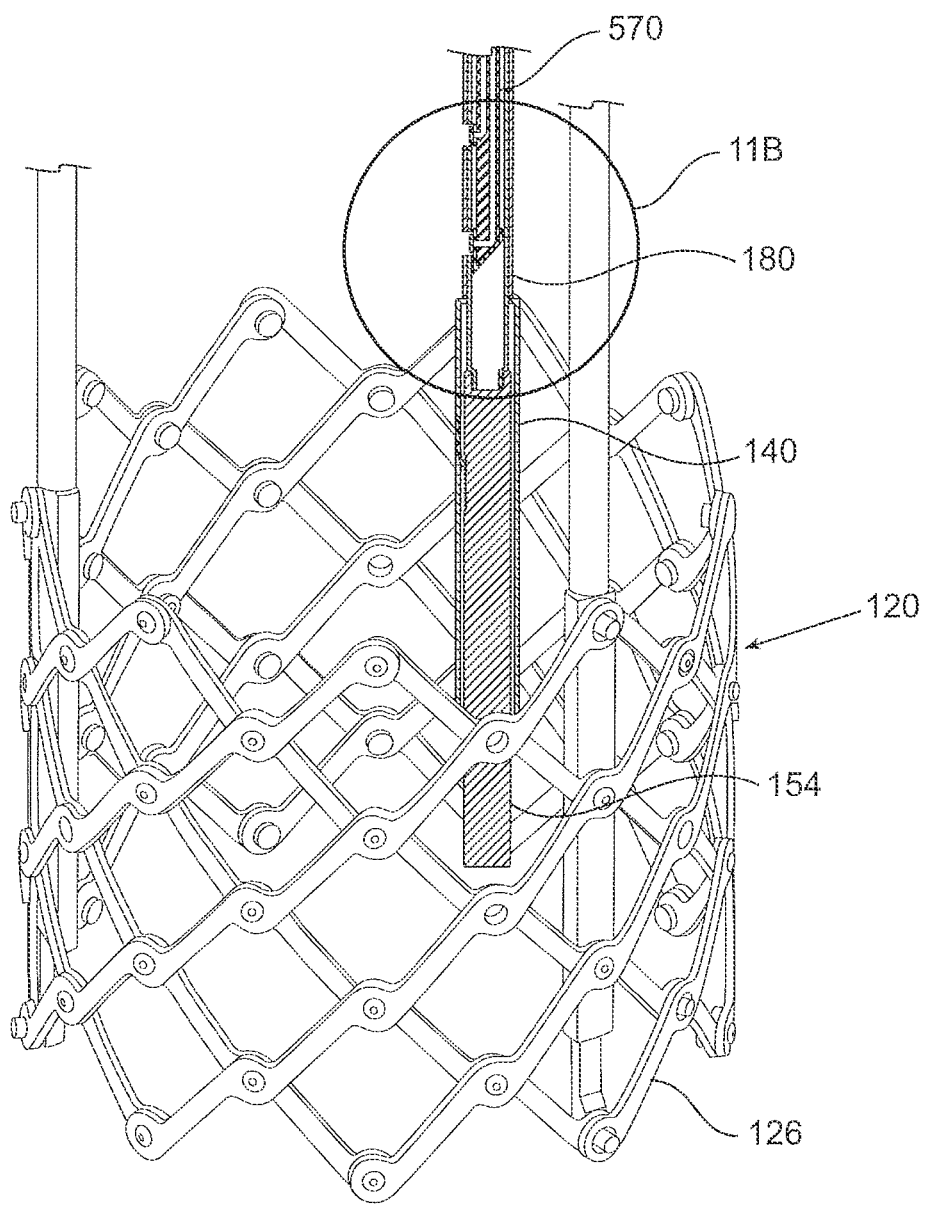
FIGS. 11A-11C show different views of a delivery assembly equipped with a multi-core continuous optic fiber, according to some embodiments.
Figure 11B:
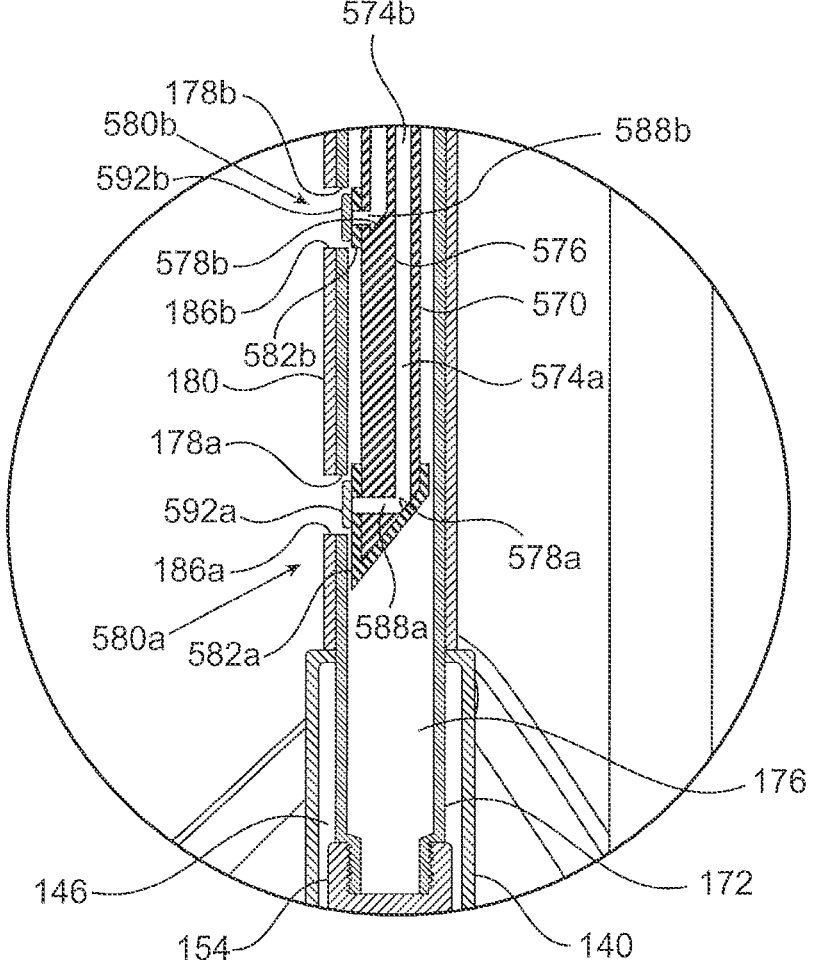
Figure 11C:
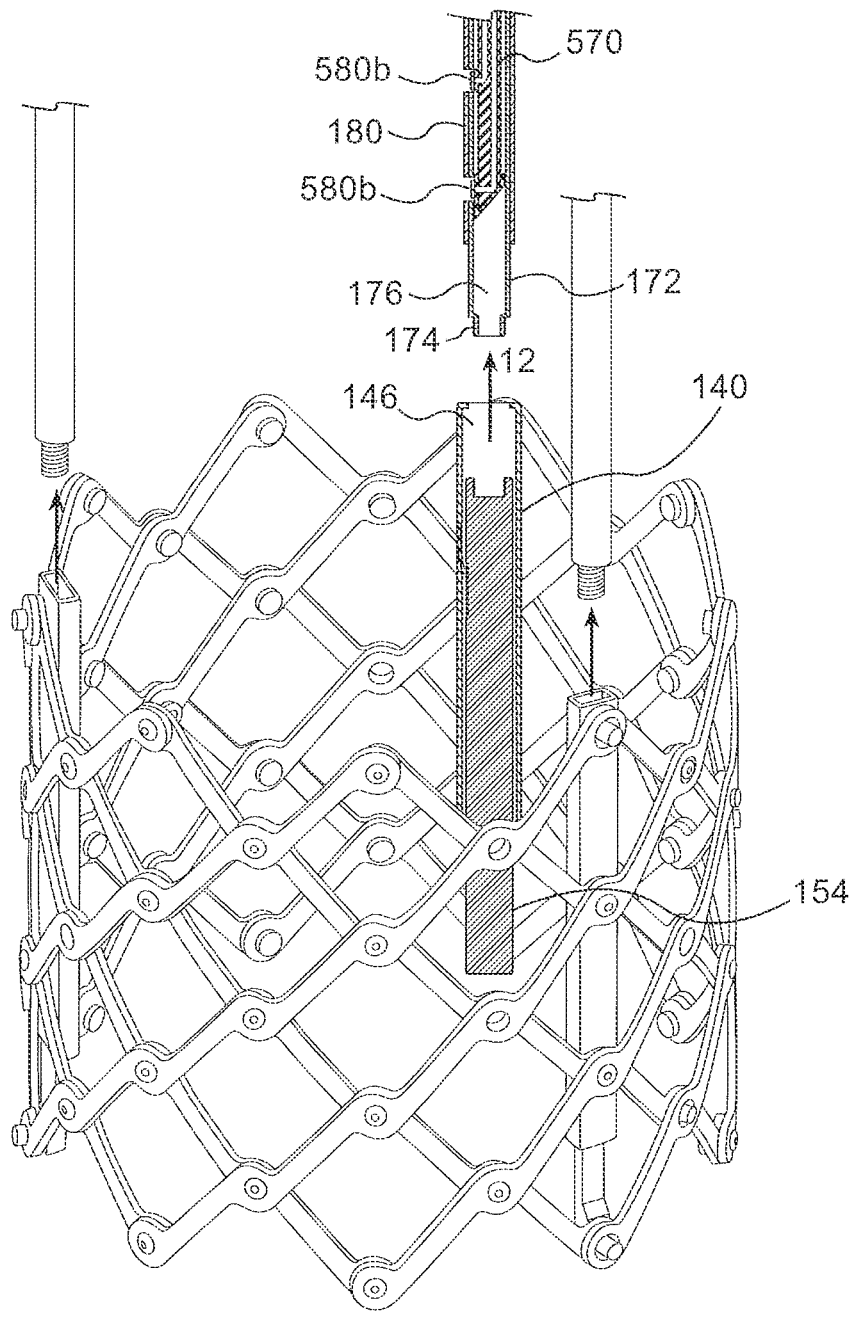

Reference is now made to FIGS. 11A-11C, showing further embodiments of a delivery assembly 100 equipped with a mechanically expandable valve 120, having at least one multi-core continuous optic fiber 570 extending through an actuation member channel 176. FIG. 11A shows a view in perspective of a mechanically expandable valve 120 having its actuation assemblies 138 connected to actuation members 172, wherein a continuous optic fiber 570 extends through an actuation member channel 176, and may be attached to an inner surface of the actuation member channel 176. FIG. 11B shows a zoomed in view of region 11B in FIG. 11A.

Continuous optic fiber 570 is generally similar in structure to continuous optic fiber 470, with the exception that it comprises a plurality of continuous optic cores 574 and a plurality of lateral pressure sensing heads 580 at the end of respective continuous optic cores 574. The exemplary multi-core continuous optic fiber 570, shown in FIGS. 11A-11B includes two continuous optic cores 574a and 574b surrounded by the fiber cladding 576.

The structure and function of the lateral pressure sensing head 580a at the distal end of continuous optic core 574a, and the lateral pressure sensing head 580b at the distal end of continuous optic core 574b, are similar to those of lateral pressure sensing heads 480 described in conjunction with FIG. 7C above, including the continuous optic cores 574a and 574b terminating at inclined distal continuous core surfaces 578a and 578b, respectively. Accordingly, description of these elements and their operation will not necessarily be repeated with respect to the embodiments presented and discussed in conjunction with FIGS. 11A-11C.

The plurality of lateral pressure sensing heads 580 are axially spaced from each other, to provide pressure measurements at different axial positions along the continuous optic fiber 570. In the exemplary embodiment of FIGS. 11A-11B, the lateral pressure sensing head 580a is axially closer to the valve's outflow end portion 122, that is to say that the position of the lateral pressure sensing heads 580a is distal to the position of lateral pressure sensing head 580b. The general considerations regarding axial positions described in connection with the plurality of axial pressure sensing heads 380 of separate continuous optic fibers 370 similarly apply to the plurality of lateral pressure sensing heads 580 of a single multi-core continuous optic fiber 570.

In the exemplary embodiment of FIGS. 11A-11B, the actuation member 172 comprises two side openings 178a and 178b, and the support sleeve 180 comprises two side openings 186a and 186b, wherein the side diaphragm 592a of the continuous optic fiber lateral pressure sensing head 580a is co-axially aligned with the actuation member side opening 178a and the support sleeve side opening 186a along its side cavity axis 590a, and wherein the side diaphragm 592b of the continuous optic fiber's lateral pressure sensing head 580b is co-axially aligned with the actuation member side opening 178b and the support sleeve side opening 186b along its side cavity axis 590b (axes 590a and 590b not shown explicitly in FIGS. 11A-11C to avoid clutter).

FIG. 11C shows the actuation member 172 and its support sleeve 180 disengaged from the actuator assembly 138, for example after being rotated around its longitudinal axis and pulled in a proximally oriented direction 12. In this state, the multi-core continuous optic fiber 570 is pulled therewith, while the valve 120 remains at the implantation site without having any excessive components attached thereto, exhibiting the same advantage as described above for the configuration of the plurality of continuous optic fibers 370 or 470 attached to the support sleeve 180.

Although two continuous cores 574 with two corresponding continuous optic fiber's lateral pressure sensing head 580 are shown in FIGS. 11A-11C, the number of cores 574 and respective continuous optic fiber's lateral pressure sensing heads 580 may vary. The general considerations regarding the amount of fibers described in connection with a plurality of continuous optic fibers 370 described above and illustrated in FIGS. 9A-9C, similarly apply to the number of continuous cores 574 within a single multi-core continuous optic fiber 570.

FIGS. 11A-11C show one embodiment of a multi-core continuous optic fiber 570 equipped with a plurality of lateral pressure sensing heads 580. According to alternative embodiments, although not shown explicitly, a multi-core continuous optic fiber 570 may comprise at least one axial pressure sensing head and at least one lateral pressure sensing heads 580. The at least one axial pressure sensing head is similar in structure and function to the axial pressure sensing head 380 described above, and is attached to, or formed at, the distal end of one of the continuous optic cores 574, such that the axial pressure sensing head is located at the fiber distal end 572. The at least one lateral pressure sensing heads 580 is thereby positioned proximal to the axial pressure sensing head. Such embodiments are mainly applicable for configurations having the multi-core continuous optic fiber 570 attached to the outer surface of a support sleeve 180, wherein the axial pressure sensing head may be positioned in close vicinity to the valve's proximal end 122.

According to yet further alternative embodiments, a multi-core continuous optic fiber 570 equipped with a plurality of lateral pressure sensing head 580 may extend through the support sleeve lumen 184, for example, by being attached to an outer surface of the actuation member 172, wherein the support sleeve 180 comprises a plurality of support sleeve side openings 186 positioned in alignment with the plurality of lateral pressure sensing head 580.

Figure 12A:
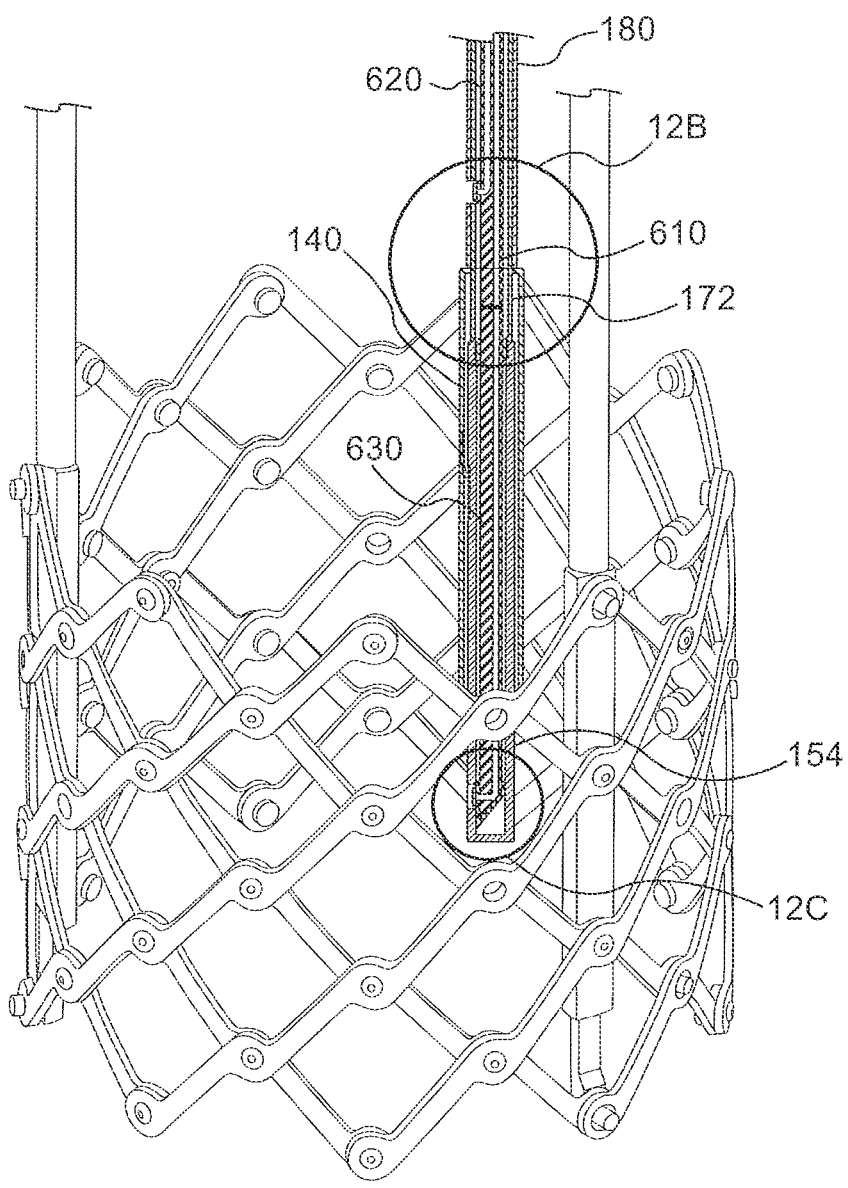
FIGS. 12A-12D show different views of a delivery assembly equipped with a multi-core optic fiber assembly, according to some embodiments.
Figures 12B, 12C:
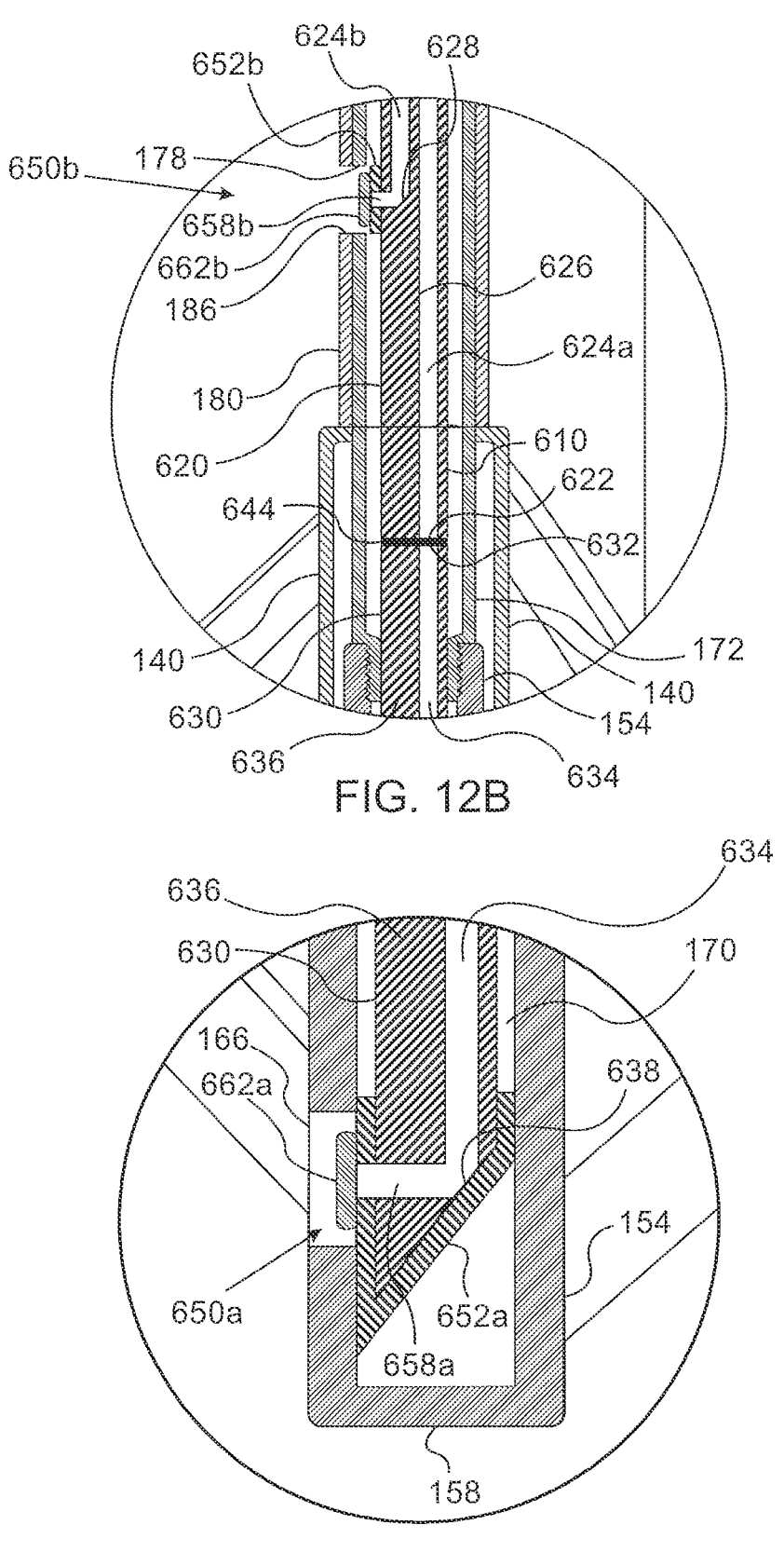

Reference is now made to FIGS. 12A-12D, showing further embodiments of a delivery assembly 100 equipped with a mechanically expandable valve 120, having at least one multi-core optic fiber assembly 610 extending through the delivery apparatus 102 and attached at its distal portion to the frame 126. FIG. 12A shows a view in perspective of a mechanically expandable valve 120 having its actuation assemblies 138 connected to actuation members 172, wherein a fiber optic assembly 610 extends through an actuation member 172 toward the inner member 154. FIG. 12B shows a zoomed in view of region 12B in FIG. 12A, and FIG. 12C shows a zoomed in view of region 12C in FIG. 12A.

Fiber optic assembly 610 is generally similar in structure to fiber optic assembly 510, with the exception that the second optic fiber section 630 comprises at least one second optic core 634 having a corresponding pressure sensing head, such as a lateral pressure sensing head 650, and the first optic fiber section 620 also comprises at least one first optic core 624 which does not extend into the second optic fiber section 630, wherein the at least one first optic core 624 is equipped a corresponding lateral pressure sensing head 650.

The exemplary multi-core fiber optic assembly 610 shown in FIGS. 12A-12D includes two first optic cores 624a and 624b surrounded by the first fiber cladding 626, and a single optic core 634 surrounded by the second fiber cladding 636. The structure and function of the lateral pressure sensing head 650a at the distal end of second optic core 634, and the lateral pressure sensing head 650b at the distal end of first optic core 624b, are similar to those of lateral pressure sensing head 450 illustrated and described in conjunction with FIG. 7B above, including the second optic core 634 terminating at a second fiber core inclined distal surface 638, and the first optic core 624b terminating at a first fiber core's inclined distal surface 628, respectively. Accordingly, description of these elements and their operation will not necessarily be repeated with respect to the embodiments presented and discussed in conjunction with FIGS. 12A-12D.

According to some embodiments, as illustrated in FIGS. 12A-12C, the first optic fiber section 620 extends through an actuation member internal channel 176, and at least a portion of the second optic fiber section 630 extends through an inner member internal channel 170.

According to some embodiments, the inner member 154 comprises at least one inner member side opening 166 extending radially outwards from the inner member, the actuation member 172 comprises at least one actuation member side opening 178 extending radially outwards from the actuation member internal channel 176, and the support sleeve 180 comprises at least one corresponding support sleeve side opening 186 extending radially outwards positioned in alignment with the respective actuation member side opening 178.

In the exemplary embodiment of FIGS. 12A-12D, the inner member 154 comprises one side openings 166, wherein the side diaphragm 662a of the optic fiber assembly lateral pressure sensing head 650a is co-axially aligned with the inner member side opening 166 along its side cavity axis 660a. Similarly, the actuation member 172 and support sleeve 180 comprise a single actuation member side opening 178 and a single support sleeve side opening 186, respectively, wherein the side diaphragm 662b of the optic fiber assembly lateral pressure sensing head 650b is co-axially aligned with both the actuation member side opening 178 and the support sleeve side opening 186 along its side cavity axis 660b (axes 660a, 660b not explicitly shown in FIGS. 12A-12D to avoid clutter).

The detachable optical coupling between the first optic fiber section 620 and the second optic fiber section 630, including the function and structure interface 644, are similar to the detachable optical coupling, including interface 244, shown and described above in conjunction with FIGS. 5A-5C, and are thus not described again herein. Nevertheless, it should be emphasized that the interface 644 optically aligns between cores that may form an axial continuous optic path along the multi-core optic fiber assembly 610, such as the first optic core 624a and the second optic core 634, while first optic cores provided with, or ending at, pressure sensor heads, such as the first optic core 624b illustrated in FIG. 12B, terminate proximal to the interface 644.

Figure 12D:
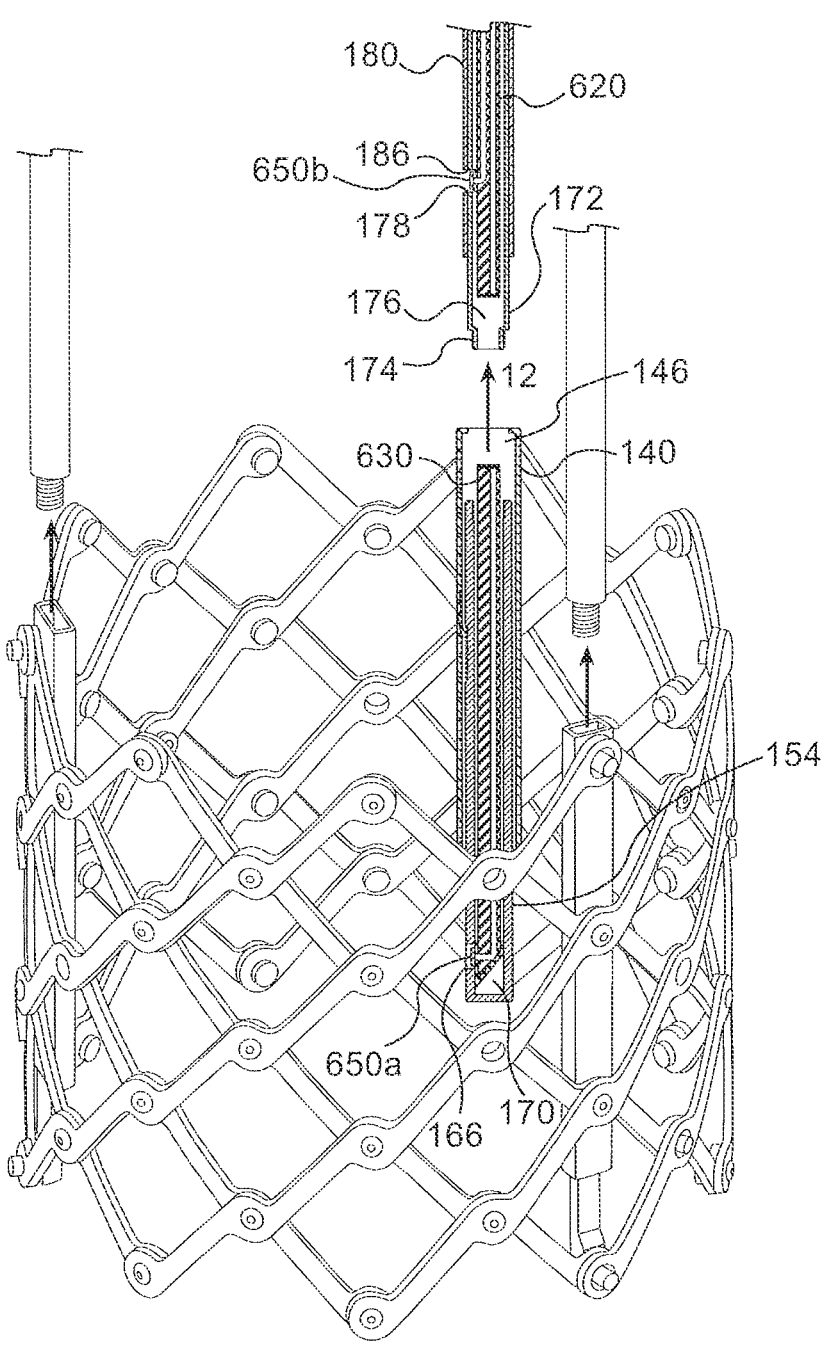

FIG. 12D shows the actuation member 172 disengaged from the actuator assembly 138, for example after being rotated around its longitudinal axis and pulled in a proximally oriented direction 12. In this state, the first optic fiber section 620, which is connected to the delivery apparatus 102, is pulled therewith after being disconnected from the second optic fiber section 630, which remains connected to the valve 120, and more specifically, to the inner member 154.

Although FIGS. 12A-12D illustrate an embodiment of multi-core fiber optic assembly 610 equipped with a single lateral pressure sensing head 650*a* positioned along the inner member 154 and a single lateral pressure sensing head 650*b* positioned along the actuation member 172, the number of cores and respective optic fiber assembly lateral pressure sensing heads 650 disposed along each of the inner member 154 and/or the actuation member 172 may vary.

Moreover, a variant of the multi-core optic fiber assembly 610 illustrated in FIGS. 12A-12D may include at least one second optic core 634 terminating at an axial pressure sensing head instead of, or in addition to, first optic cores terminating at lateral pressure sensing heads as described above.

Figure 13A:
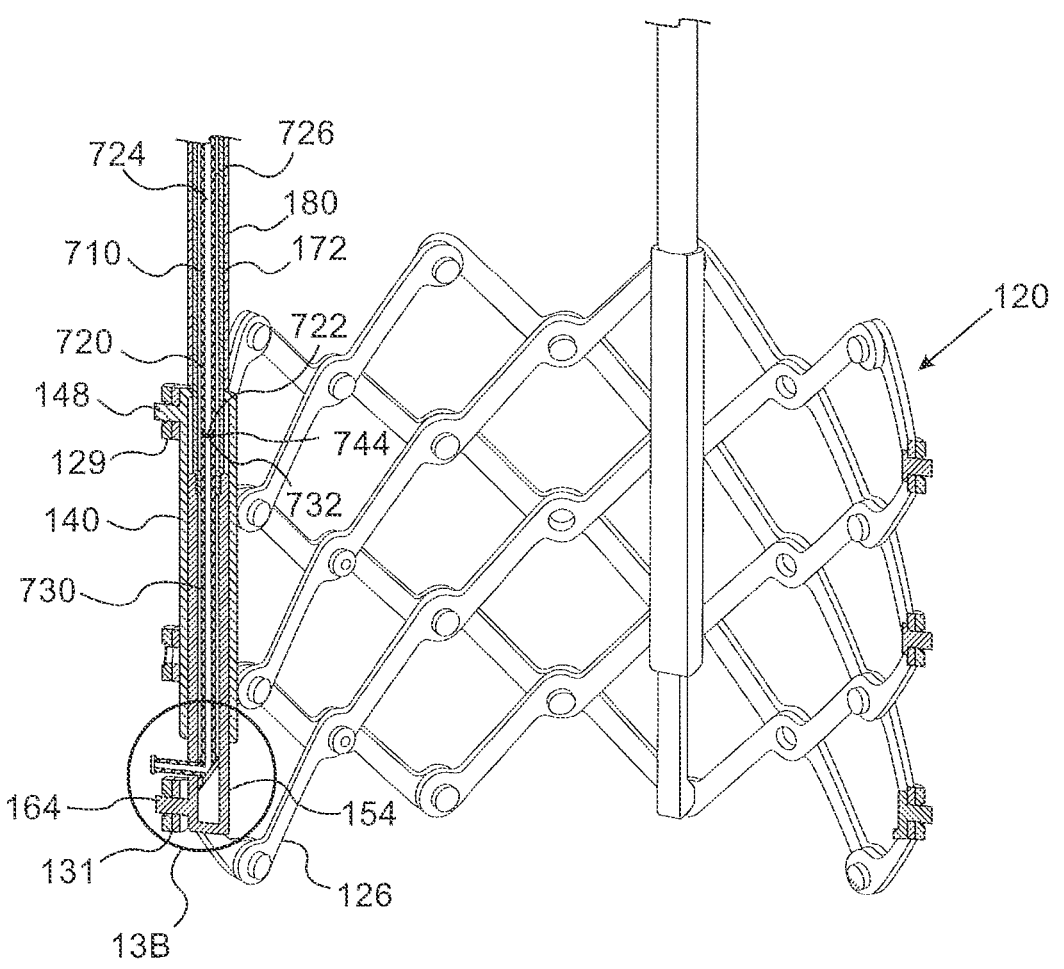
FIGS. 13A-13C show different views of a delivery assembly equipped with an optic fiber assembly, according to some embodiments.
Figure 13B:
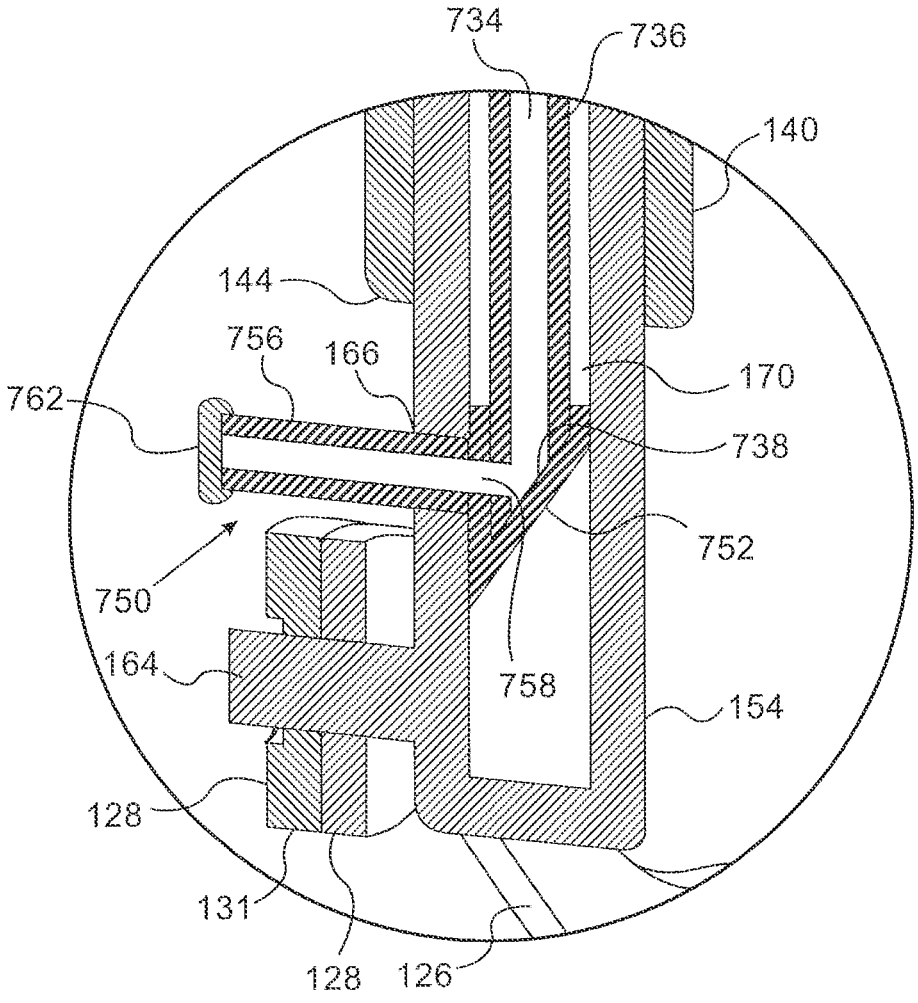
Figure 13C:
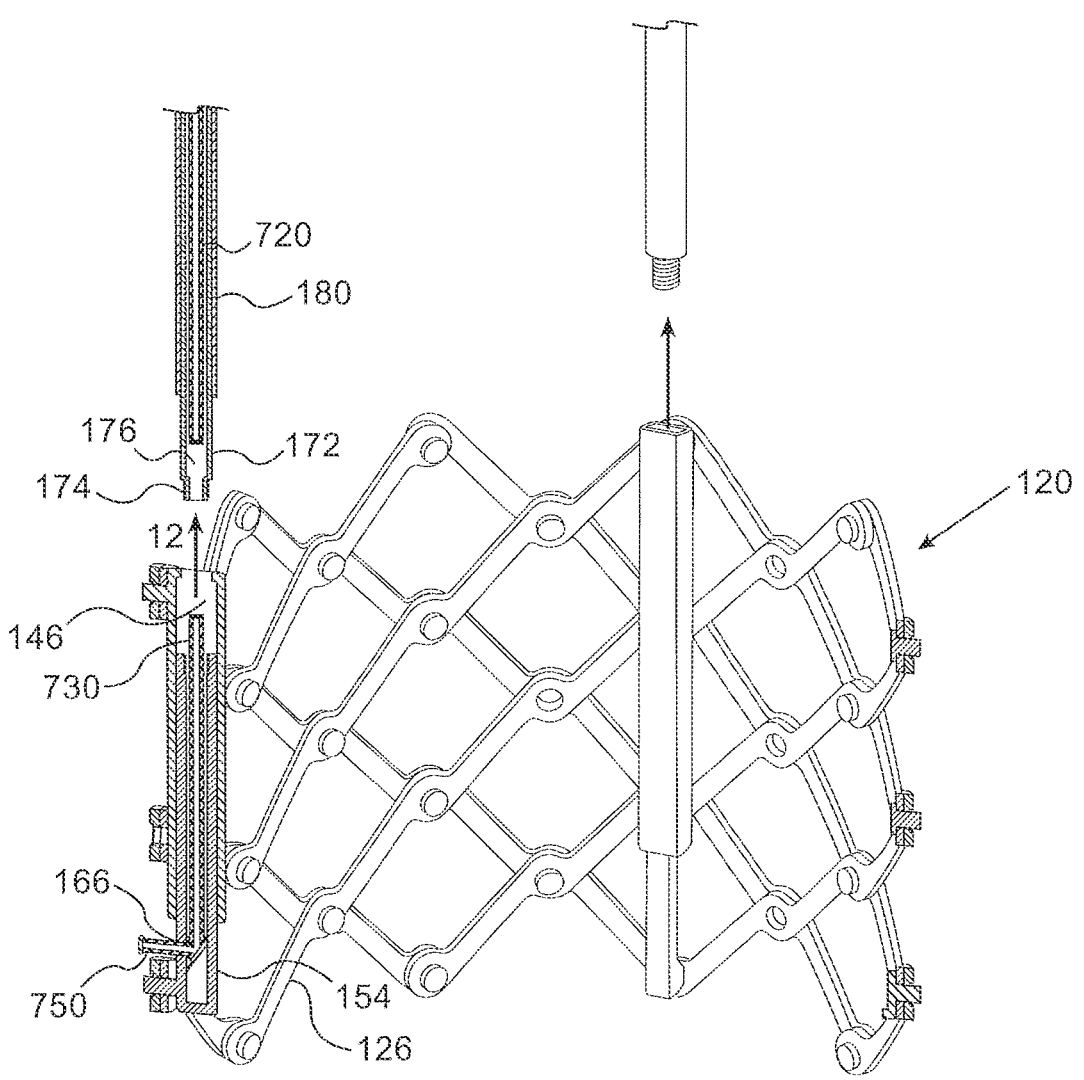

Reference is now made to FIGS. 13A-13C, showing an exemplary embodiment of a delivery assembly 100 equipped with a mechanically expandable valve 120, having at least one optic fiber assembly 710 extending through the delivery apparatus 102 and attached at its distal portion to the frame 126, such as to an actuator member 154. Optic fiber assembly 710 is generally similar to optic fiber assembly 510, the main difference being that the housing 752 of the lateral pressure sensing head 750 further comprises a lateral extension 756, and the side cavity 758 is longer than the side cavity 558. The side diaphragm 762 overlays, and is attached to, the edge of the lateral extension 756 opposite to the second optic core inclined surface 738. FIG. 13B shows a zoomed in view of region 13B in FIG. 13A. FIG. 13C shows the actuation arm assembly member 171 of the delivery apparatus 102 detached from the actuator assembly 138 of the valve 120.

The position, extension and function of each component of the optic fiber assembly 710 relative to other components thereof, and relative to the inner member 154 and the actuation arm assembly member 171, are substantially similar to those shown and described above for the optic fiber assembly 510 in conjunction with FIGS. 7A-C, and are thus not described again herein except with regard to the lateral orientation of the lateral pressure sensing head 750. However, contrary to the lateral/tangential orientation of pressure sensor heads relative to the valve's frame 126 as illustrated the side diaphragm 562 in FIGS. 7A-C, or contrary to alternative embodiments of the pressure sensor heads being oriented radially inward toward a longitudinal axis 121 (not explicitly illustrated), the lateral pressure sensing heads 750 are oriented radially outward, such that their lateral extensions 756, having the side diaphragms 762 attached thereto, are extending beyond the perimeter of the valve frame 126, thereby allowing the side diaphragms 762 to contact the blood vessel wall during valve expansion. This arrangement allows the lateral pressure sensing head 750 to function as a lateral contact-force sensing head, configured to detect and measure a contact force applied by the prosthetic valve 120 when it is in contact with, and is pressed against, the surrounding tissue, such as a native annulus. Such a contact-force sensing head 750 may provide information and feedback to the operator regarding the resistive force being applied to the prosthetic valve 120. For example, when a detected contact force exceeds a predetermined pressure threshold (for example, corresponding to a pressure that may cause tissue damage or potentially even annular rupture during) during valve expansion, the delivery system may produce an alert. For example, the handle 110 may produce a detectable, visual or auditory, alert.

According to some embodiments, additional components of the prosthetic valve 120, such as the skirt 136 or any other relevant component, can be modified by having respective openings through which the lateral extensions 756 can extend in a radially outward orientation relative to the longitudinal axis 121, in order to facilitate contact between the side diaphragms 762 and the surrounding tissue.

The thickness, shape, diameter or material properties of a diaphragm of a pressure sensing head can be chosen to fulfill the requirements of different sensitivities in various applications. For example, a side diaphragms 762 configured to be pressed against a blood vessel wall may be more rigid than a side diaphragm 562 configured to deflect due to contact with blood flow.

Although one optic fiber assembly 710 is illustrated in FIG. 13A, any number of optic fiber assemblies 710 (for example, two, three, etc.) are contemplated. In some cases, it may be preferably to utilize a plurality of optic fiber assemblies 710, having their respective lateral contact-force sensing heads 750 circumferentially disposed at equal or varying distances there-between, around the circumference of a prosthetic valve 120, to provide a more comprehensive landscape of the force applied by the valve 120 on different regions of the surrounding tissue, during expansion thereof.

Advantageously, a lateral contact-force sensing head 750 attached to a prosthetic valve 120 provides valuable feedback to the clinician with respect to the force being applied to the surrounding tissue, which may enable to prevent, or at least reduce, potential trauma to a tissue (for example, the annulus).

According to some embodiments, at least two optic fiber assemblies equipped with lateral pressure sensing heads, such as optic fiber assemble 410, multi-core optic fiber assembly 510 or multi-core optic fiber assembly 610, are attached to a single actuator assembly 138, wherein each of the two corresponding lateral pressure sensing heads is oriented in an opposite directions relative to the longitudinal axis 121.

According to some embodiments, a plurality of optic fiber assemblies may extend through the same actuation arm assembly 171 and the same actuator assembly 138. For example, a plurality of optic fiber assemblies may extend through a single actuation arm channel 176 and a single inner member channel 170.

Figure 14A:
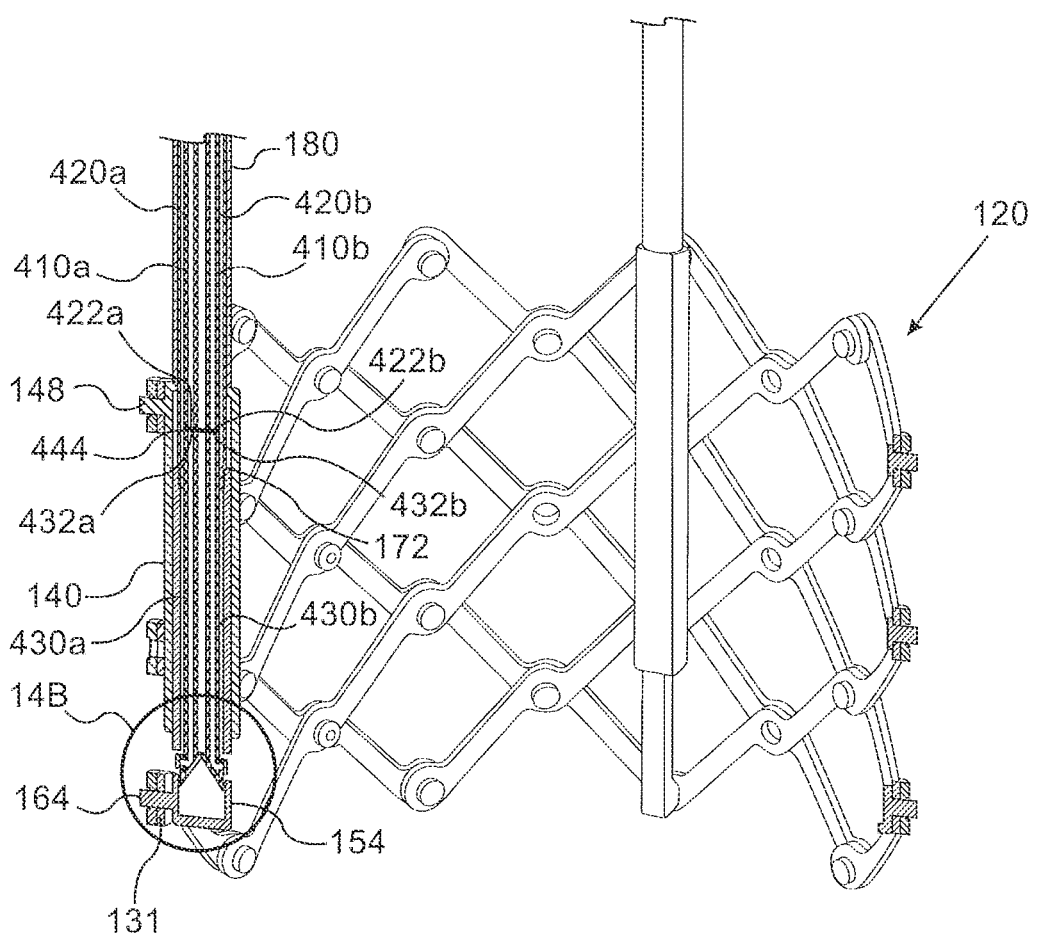
FIGS. 14A-14C show different views of a delivery assembly equipped with a plurality of optic fiber assemblies, according to some embodiments.
Figure 14B:
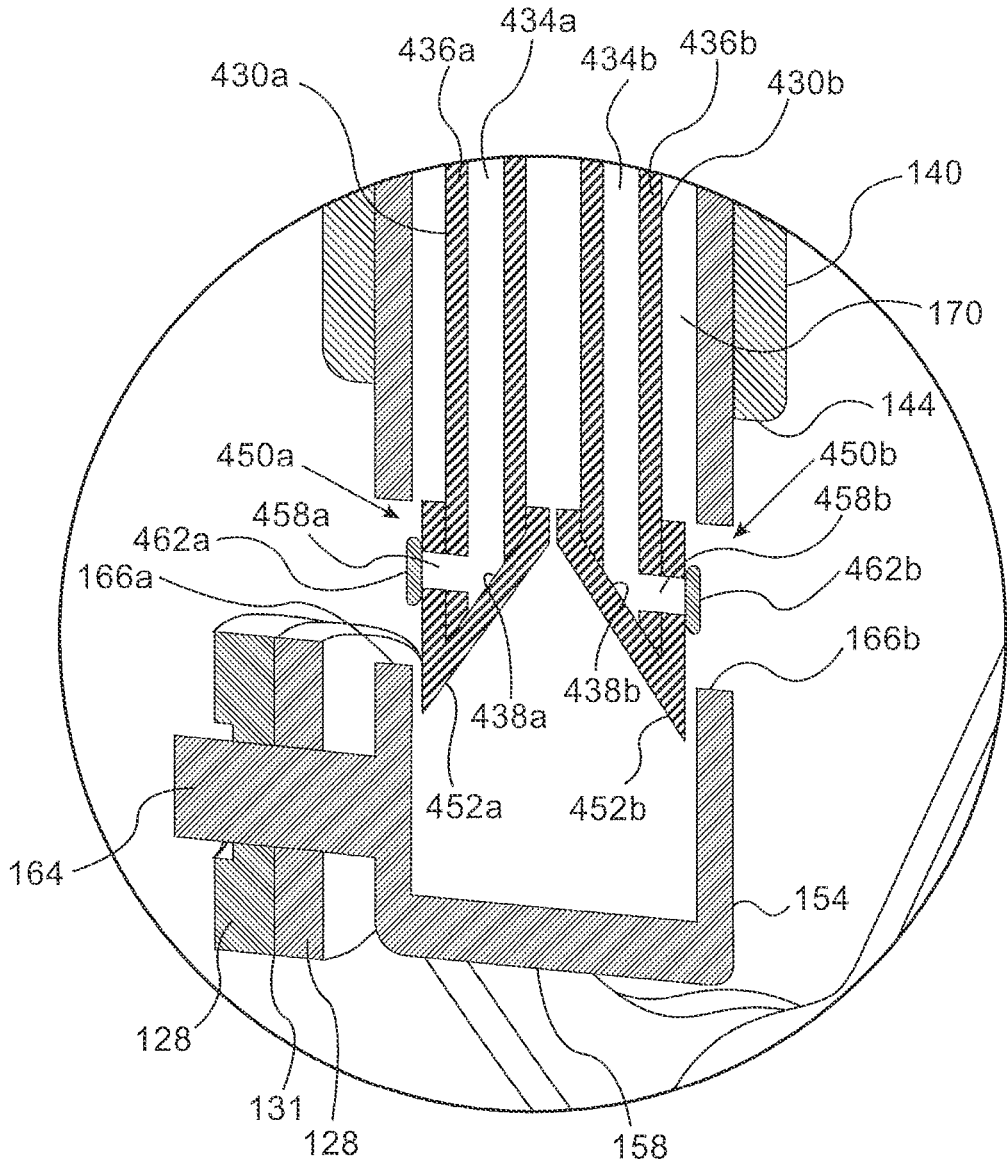
Figure 14C:
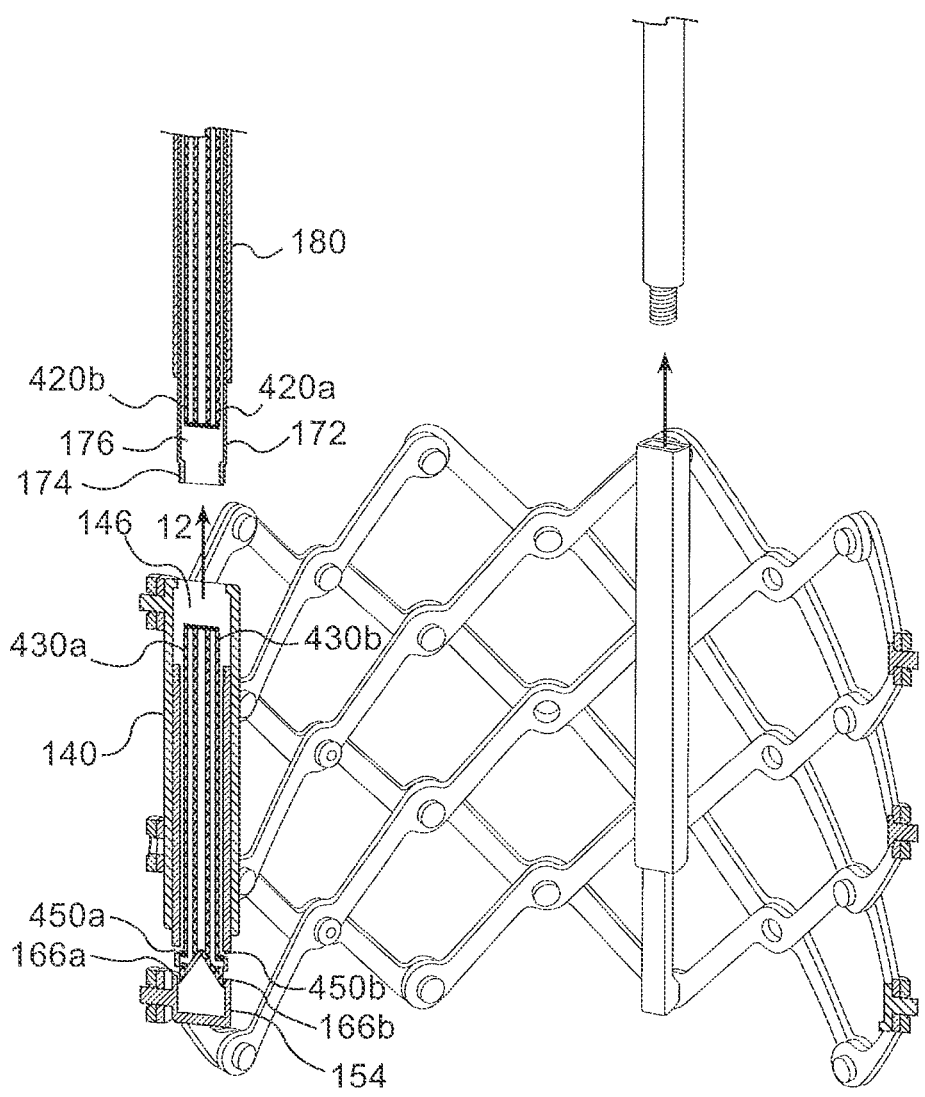

Reference is now made to FIGS. 14A-14C, showing further embodiments of a delivery assembly 100 equipped with a mechanically expandable valve 120, having at least two optic fiber assemblies 410 extending through the delivery apparatus 102 and attached at its distal portion to the frame 126. FIG. 14A shows a view in perspective of a mechanically expandable valve 120 having its actuation assemblies 138 connected to actuation members 172, wherein two optic fiber assemblies 410 extend through the same actuation member 172 toward the same inner member 154. FIG. 14B shows a zoomed-in view of region 14B in FIG. 14A.

In the embodiment illustrated in FIGS. 14A-14C, the at least two first optic fiber sections 420*a* and 420*b* extends through a single internal channel 176 formed within an actuation member 172, and at least a portion of each of the corresponding second optic fiber section 430*a* and 430*b* extends through a single channel 170 formed within an inner member 154.

As further shown, the inner member 154 comprises at least two inner member side openings 166*a* and 166*b* extending from the inner member channel 170 at diametrically opposing radial directions. For example, the side opening 166a may extend radially outward, away from the longitudinal axis 121, and the side opening 166b may extend radially inward, toward the longitudinal axis 121.

According to some embodiments, one side diaphragm 462a of an optic fiber assembly lateral pressure sensing head 450a is co-axially aligned with the side opening 166a that extends radially outward from the longitudinal axis 121, and another side diaphragm 462b of another optic fiber assembly lateral pressure sensing head 450b is co-axially aligned with the opposite side opening 166b that extends radially inward toward the longitudinal axis 121. This configuration enables simultaneous pressure measurements within the valve 120, and outside the valve 120, which can be useful, for example, for detecting hemodynamic disorders both in the Left Ventricle Outflow Tract (LVOT) as well as the internal pressure within the valve itself, assuming that the inflow portion 124 to which both lateral pressure sensing head 450 are attached, extends into the left ventricle. Thus, in this arrangement, two second optic fiber section 430a and 430b are attached to, and optionally extend through, the same actuator assembly 138, such that their respective lateral pressure sensing heads 450a and 450b are oriented at diametrically opposing radial directions.

While both of the side openings 166 and the corresponding pressure sensing heads 450 aligned therewith are illustrated in FIGS. 14A-14B in close proximity to the inner member distal end 158, it will be understood that the side openings 166 can be formed at any other position along the length of the inner member 154, having the corresponding pressure sensing heads 450 aligned therewith.

While both of the side openings 166a and 166b, along with the lateral pressure sensing heads 450a and 450b aligned therewith, are illustrated in FIGS. 14A-14B located at the same axial position, it will be understood that each of the lateral pressure sensing heads 450a and 450b, along with its respective side opening 166a and 166b, can be located at a different axial position along the length of the inner member 154, such that the pressure sensing heads 450a and 450b are both axially spaced from each other, and oriented at diametrically opposing radial directions.

An outwardly oriented pressure sensing head, such as the pressure sensing head 450b of FIGS. 14A-B, may be further useful for detection of paravalvular leakage during prosthetic valve 120 implantation.

According to some embodiments, optical coupling between the at least two first optic fiber sections 420a and 420b and the at least two second optic fiber sections 430a and 430b requires careful alignments of the corresponding optic cores. According to some embodiments, the actuation member channel 176 and/or the inner member channel 170 comprise a non-circular cross-sectional profile, for example in the form of the number eight, to facilitate proper positioning and alignment of the first optic fiber sections 420a, 420b, and/or the second optic fiber sections 430a, 430b, therein (embodiments not shown).

While both optic fiber assemblies 410a and 410b are shown in the embodiment of FIGS. 14A-14B extending through a single actuation member channel 176 and a single inner member channel 170, other embodiments may include at least two separate actuation member channels 176 extending through the same actuation member 172, and at least two separate actuation member channels 176 extending through the same inner member 154, wherein each separate channel is configured to accommodate a single optic fiber section, thereby facilitating easier alignment of their respective optic cores at interface 444.

FIG. 14C shows the actuation member 172 disengaged from the actuator assembly 138, for example after being rotated around its longitudinal axis and pulled in a proximally oriented direction 12. In this state, the at least two first optic fiber sections 420a and 420b, which are connected to the delivery apparatus 102, are pulled therewith after being disconnected from the respective at least two second optic fiber sections 430a and 430b, which remain connected to the valve 120, and more specifically, to the inner member 154.

According to some embodiments, a multi-core optic fiber assembly equipped with at least two lateral pressure sensing heads, may extend through an actuation arm assembly 171 and an actuator assembly 138, for example through an actuation arm channel 176 and an inner member channel 170, having both lateral pressure sensing heads attached to the actuator assembly 138 and oriented at diametrically opposing radial directions.

Figure 15A:
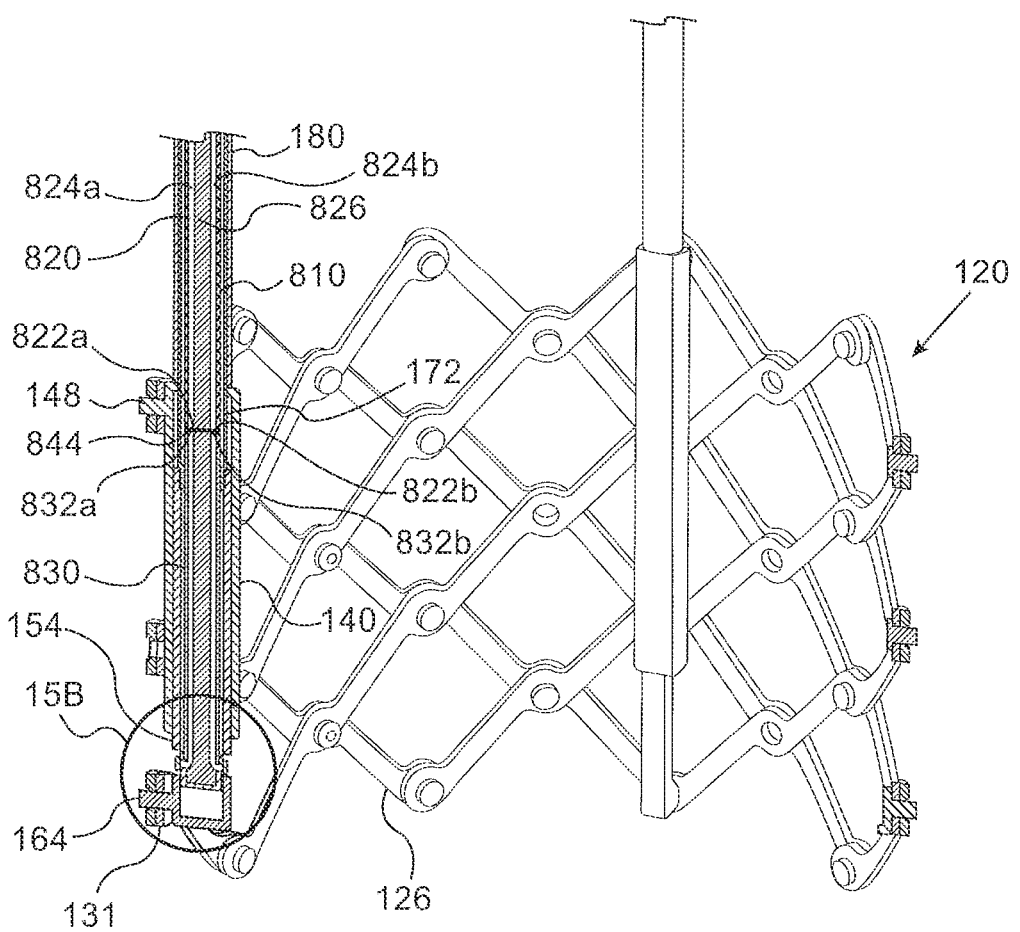
FIGS. 15A-15C show different views of a delivery assembly equipped with a multi-core optic fiber assembly, according to some embodiments.
Figure 15B:
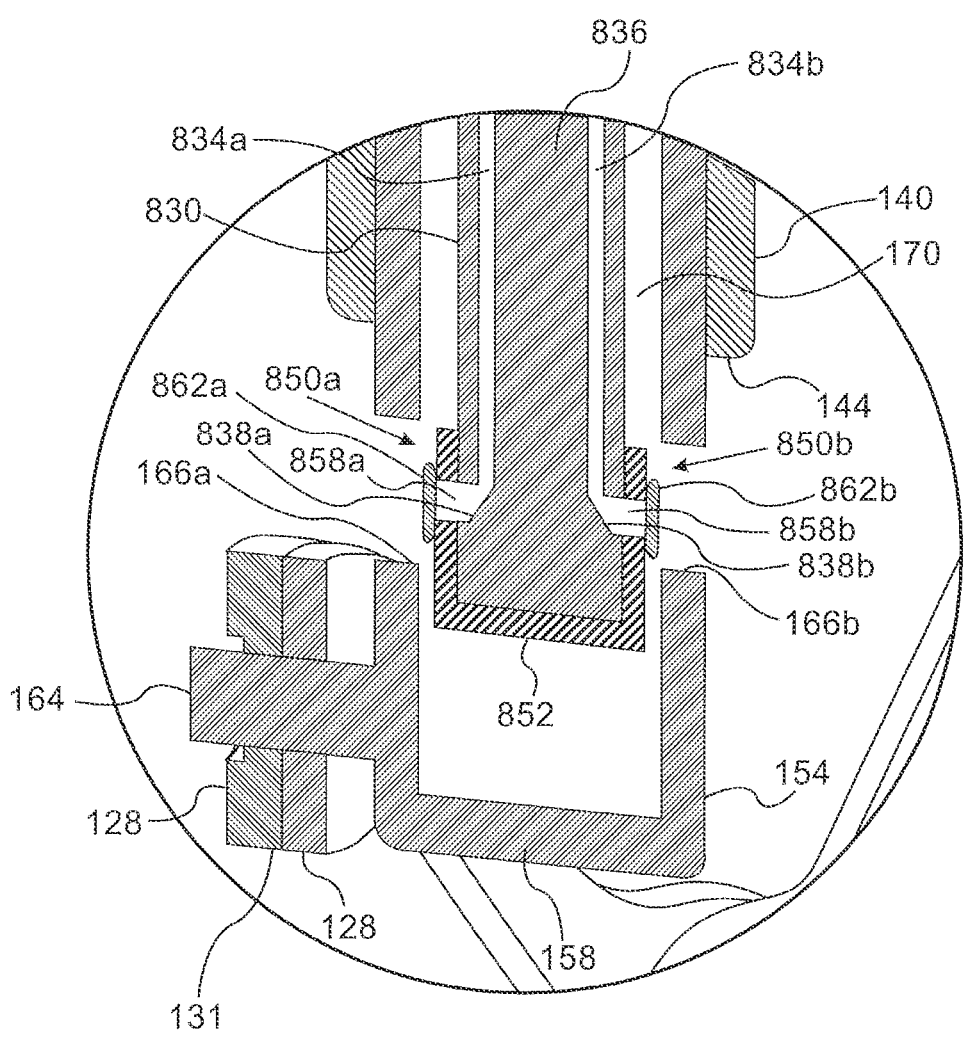
Figure 15C:
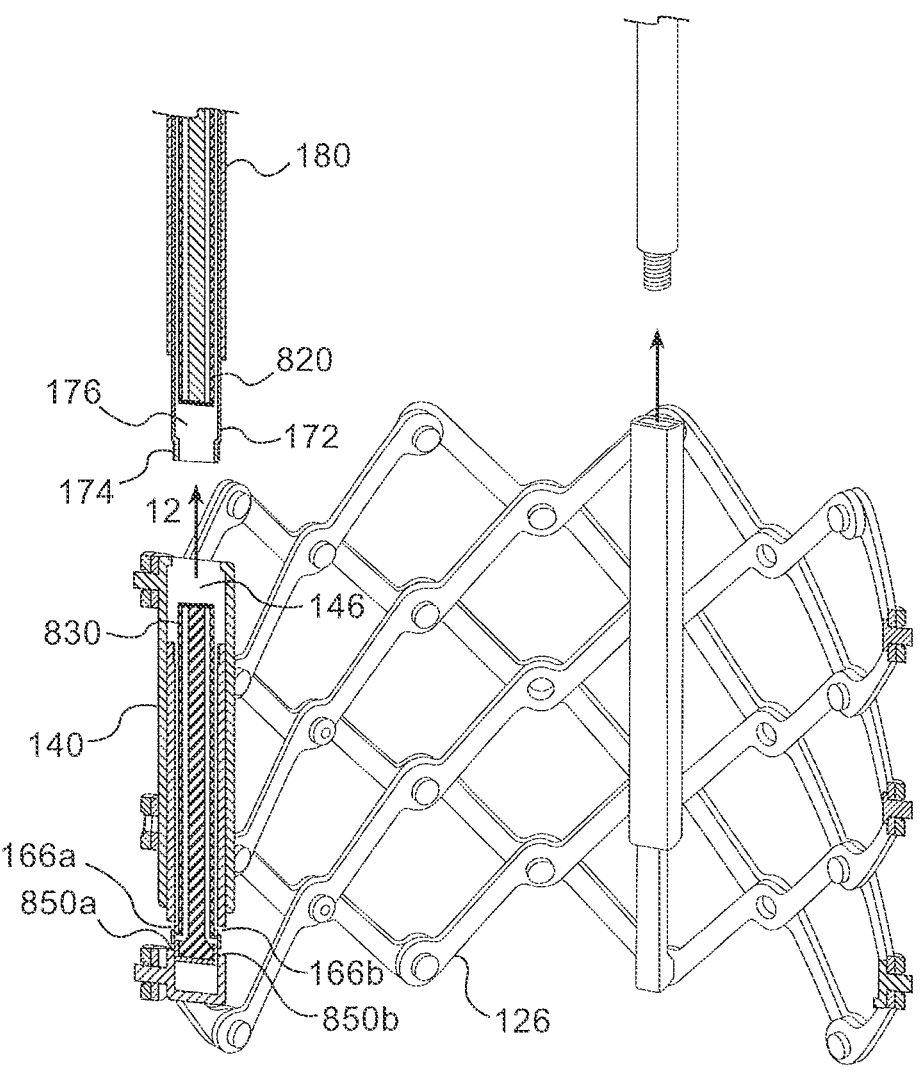

Reference is now made to FIGS. 15A-15C, showing embodiments of a delivery assembly 100 equipped with a mechanically expandable valve 120, having at least one multi-core optic fiber assembly 810 extending through the delivery apparatus 102, and attached at its distal portion, to the frame 126. FIG. 15A shows a view in perspective of a mechanically expandable valve 120 having its actuation assemblies 138 connected to actuation members 172, wherein a multi-core fiber optic assembly 810 extends through an actuation member 172 toward the inner member 154. FIG. 15B shows a zoomed-in view of region 15B in FIG. 15A.

Multi-core fiber optic assembly 810 is generally similar in structure to multi-core fiber optic assembly 510, comprising at least two optic cores extending through the first and second optic fiber sections 820 and 830, with the exception that at least two lateral pressure sensing heads 850a and 850b at the distal ends of corresponding second optic cores 834a and 834b, respectively, are oriented at diametrically opposing radial directions.

The exemplary multi-core fiber optic assembly 810 shown in FIGS. 15A-15C includes two first optic cores 824a and 824b surrounded by the first fiber cladding 826, and two second optic cores 834a and 834b surrounded by the second fiber cladding 836. The structure and function of the lateral pressure sensing head 850a at the distal end of second optic core 834a, and the lateral pressure sensing head 850b at the distal end of second optic core 834b, are similar to those of lateral pressure sensing head 850 described in conjunction with FIG. 7B above, including the second optic cores 834a and 834b terminating at second optic core inclined distal surfaces 838a and 838b, respectively. Accordingly, description of these elements and their operation will not necessarily be repeated with respect to the embodiments presented and discussed in conjunction with FIGS. 15A-15C.

According to some embodiments, as illustrated in FIGS. 15A-15C, the first optic fiber section 820 extends through an actuation member internal channel 176, and at least a portion of the second optic fiber section 830 extends through an inner member internal channel 170.

Similar to the embodiments described above in conjunction with FIGS. 14A-14C, the inner member 154 may comprises at least two inner member side openings 166a and 166b extending from the inner member channel 170 at diametrically opposing radial directions. As shown in the exemplary embodiment of FIGS. 15A-15B, the side opening 166a extends radially outward, away from the longitudinal axis 121, and the side opening 166b extends radially inward, toward the longitudinal axis 121.

One side diaphragm 862*a* of an optic fiber assembly lateral pressure sensing head 850*a* is co-axially aligned with the side opening 166*a* that extends radially outwards from the longitudinal axis 121, and another side diaphragm 862*b* of another optic fiber assembly lateral pressure sensing head 850*b* is co-axially aligned with the opposite side opening 166*b* that extends radially inwards from the longitudinal axis 121. This configuration enables simultaneous measurements within the valve 120, and outside the valve 120, which can be useful for the same applications described above in conjunction with FIGS. 14A-14C.

While both of the side openings 166 and the corresponding pressure sensing heads 850 aligned therewith are illustrated in FIGS. 15A-15B in close proximity to the inner member distal end 158, it will be understood that the side openings 166 can be formed at any other position along the length of the inner member 154, having the corresponding pressure sensing heads 850 aligned therewith.

While both of the side openings 166*a* and 166*b*, along with the pressure sensing heads 850*a* and 850*b* aligned therewith, are illustrated in FIGS. 15A-15B in the same axial position, it will be understood that each of the lateral pressure sensing heads 850*a* and 850*b*, along with its respective side opening 166*a* and 166*b*, can be located at a different axial position along the length of the inner member 154, such that the pressure sensing heads 850*a* and 850*b* of a single a single second optic fiber section 830 can be both axially spaced from each other, and oriented at diametrically opposing radial directions.

The detachable optical coupling between the first optic fiber section 820 and the second optic fiber section 830, including the function and structure interface 844, are similar to the detachable optical coupling, including interface 544, shown and described above in conjunction with FIGS. 8A-8C, and are thus not described again herein.

FIG. 15C shows the actuation member 172 disengaged from the actuator assembly 138, for example after being rotated around its longitudinal axis and pulled in a proximally oriented direction 12. In this state, the first optic fiber section 820, which is connected to the delivery apparatus 102, is pulled therewith after being disconnected from the second optic fiber section 830, which remains connected to the valve 120, and more specifically, to the inner member 154.

A delivery assembly 100 may have various other configurations based on combinations of the optic fiber types and arrangements described herein above.

According to another aspect, a delivery assembly 100 comprises at least one multi-core optic fiber 1100 attached to either a component of the delivery apparatus 102 and/or to a component of the prosthetic valve 120, having axially spaced pressure sensing heads 1200. The multi-core optic fiber 1100 may take the form of any of the above described multi-core optic fibers, such as multi-core optic fiber assemblies 510, 610, 810, or multi-core continuous optic fiber 570. A pressure sensing head 1200 may take the form of any of the above described pressure sensing heads, such as axial pressure sensing heads 350, 380 or lateral pressure sensing heads 450, 480, 650, 750, 850.

According to an alternative aspect, a delivery assembly 100 comprises at least two optic fibers 1000, each equipped with at least one pressure sensing head 1200, wherein at least two pressure sensing heads are axially spaced from each other, and wherein each of the optic fibers is attached to either a component of the delivery apparatus 102 and/or to a component of the prosthetic valve 120. The optic fiber 1000 may take the form of any of the above described optic fibers having at least one optic core terminating at a pressure sensing head 1200, such as optic fiber assemblies 310, 410, 710, continuous optic fibers 370, 470, and/or multi-core optic fiber 1100.

Potential configurations may include at least one optic fiber assembly 1010 attached to a component of the prosthetic valve 120, such as an inner member 154, and at least one continuous optic fiber 1070 attached to a component of the delivery apparatus 102, such as the actuation member 172 and/or the support sleeve 180 of at least one actuation arm assembly 171. The optic fiber assembly 1010 may take the form of any of the above described optic fiber assemblies, such as optic fiber assemblies 310, 410, 710, and/or multi-core optic fiber assemblies 510, 610, 810. The continuous optic fiber 1070 may take the form of any of the above described continuous optic fibers, such as continuous optic fibers 370, 470, and/or multi-core continuous optic fiber 570.

An arrangement of at least one optic fiber assembly 1010 attached to an inner member 154, extending for example through an inner member channel 170, may be similar to the attachment and operation of optic fiber assembly 310 as presented and discussed in conjunction with FIGS. 6A-6D, may be similar to the attachment and operation of optic fiber assembly 410 as presented and discussed in conjunction with FIGS. 7A-7D, may be similar to the attachment and operation of multi-core optic fiber assembly 510 as presented and discussed in conjunction with FIGS. 8A-8C, may be similar to the attachment and operation of multi-core optic fiber assembly 610 as presented and discussed in conjunction with FIGS. 12A-12D, may be similar to the attachment and operation of optic fiber assembly 710 as presented and discussed in conjunction with FIGS. 13A-13C, may be similar to the attachment and operation of optic fiber assemblies 410 as presented and discussed in conjunction with FIGS. 14A-14C, or may be similar to the attachment and operation of multi-core optic fiber assembly 810 as presented and discussed in conjunction with FIGS. 15A-15C.

Alternatively or additionally, an optic fiber assembly 1010, and more specifically, a second optic fiber of an optic fiber assembly 1010, may be attached to other regions of the actuator assembly 138, such as, but not limited to, an outer surface of the inner member 150, an inner surface of the outer member lumen 146, and/or an outer surface of the outer member 140. Moreover, an optic fiber assembly 1010, and more specifically, a second optic fiber of an optic fiber assembly 1010, may be alternatively or additionally attached to other portions of the prosthetic valve 120, such as the frame 126, including apices 129, 131 and/or other junctions 130 thereof.

An arrangement of at least one continuous optic fiber 1070 attached to the actuation member 172 and/or the support sleeve 180 may be similar to the attachment and operation of continuous optic fiber 370 as presented and discussed in conjunction with FIGS. 6A-6D, may be similar to the attachment and operation of continuous optic fiber 470 as presented and discussed in conjunction with FIGS. 7A-7D, may be similar to the attachment and operation of a plurality of continuous optic fibers 370 as presented and discussed in conjunction with FIGS. 9A-9C, may be similar to the attachment and operation of a plurality of continuous optic fibers 470 as presented and discussed in conjunction with FIGS. 10A-10C, or may be similar to the attachment and operation of multi-core continuous optic fiber 570 as presented and discussed in conjunction with FIGS. 11A-11C.

While the embodiments depicted in FIGS. 5A-15C show optic fibers 1000 attached to or embedded within one actuator assembly 138 and/or one actuation arm assembly 171, it should be understood that optic fibers 1000 according to any of the embodiments described herein above, can be attached to or embedded within a plurality, and potentially all of the actuator assemblies 138 and/or actuation arm assemblies 171 of a delivery assembly 100.

While illustrated embodiments having at least one optic fiber assembly 1010 attached to the prosthetic valve 120, and at least one continuous optic fiber 1070 attached to the delivery apparatus 102, show the continuous optic fiber 1070 attached to the same actuation arm assembly 171 through which or along which the optic fiber assembly 1010 extends, for example toward the actuator assembly 138, it will be clear that the continuous optic fiber 1070 may be attached to a different actuation arm assembly 171, not connected to the actuator assembly 138 to which the optic fiber assembly 1010 is attached.

One specific arrangement may include a plurality of optic fiber assemblies 310 equipped with respective axial pressure sensing heads 350, attached to the prosthetic valve 120 and positioned such that the respective axial pressure sensing heads 350 are circumferentially distanced from each other around the valve 120. In some implementations, the axial pressure sensing heads 350 are positioned at the outflow end portion 122. In particular implementations, the respective plurality of the diaphragms 362 of the axial pressure sensing heads 350 are flush with or distal to the respective inner member distal openings 168. Such an arrangement is particularly useful if a prosthetic valves 168 is mounted against the aortic annulus, such that its distal end 124 protrudes into the left ventricle, or more specifically, into the LVOT (not shown).

Incorporating at least two axial pressure sensing heads 350 configured to provide reading from two circumferentially distanced LVOT regions may provide simultaneous measurement of flow at these regions, and comparison between such measurements for detection of abnormal flow patterns and hemodynamic disturbances, which may depend, for example, on the orientation and depth of the valve 120 within the LVOT. Advantageously, real-time detection of flow disturbances in the LVOT can be followed by corrective actions, such as valve repositioning. As stated above, time-resolved pressure measurement can be correlated to flow using known empirical relationships established in clinical literature. Thus, flow patterns, such as in the region of the LVOT, may be derived from pressure measurements acquired by pressure sensing heads 1200.

In other implementations, a plurality of optic fiber assemblies 410 equipped with respective lateral pressure sensing heads 450, are attached to the prosthetic valve 120 and positioned such that the respective lateral pressure sensing heads 450 are circumferentially distanced from each other around the valve 120. In some implementations, the lateral pressure sensing heads 450 are positioned at the outflow end portion 122.

It is to be understood that continuous optic fibers can be similarly used, such as continuous optic fibers 370 having circumferentially distanced axial pressure sensing heads 380, instead of optic fiber assemblies 310, and such as continuous optic fibers 470 having circumferentially distanced lateral pressure sensing heads 480, instead of optic fiber assemblies 410, mutatis mutandis. The continuous optic fibers 370, 470 can be coupled to the valve 120 in a releasable manner, such as via frangible attachments, such that upon application of a pulling force thereto, exceeding a certain threshold, the continuous optic fibers 370, 470 can be forcibly detached (for example, by tearing temporary sutures, breaking relatively weak gluing bonds, and the like), enabling such assemblies to be retracted from the patient's body, along with the remainder of the delivery apparatus 102, at the end of the implantation procedure.

According to some embodiments, optic fibers according to any of the embodiments of the current disclosure are operatively coupled to a control unit (not shown). According to some embodiments, the control unit is configured to receive signals, such as optic signals, from at least one optic fiber assembly 210, representative of the axial strain of a component of the prosthetic valve 120. The control unit can be configured to continuously calculate the diameter and the radial force of the prosthetic valve 120 as it expands, based on measurement inputs provided by at least one optic fiber assembly 210.

According to some embodiments, the control unit is configured to receive signals from at least two pressure sensing heads 1200 axially spaced from each other, representative of the pressure in the vicinity of each of the corresponding pressure sensing heads 1200. The control unit can be configured to continuously calculate the pressure drop across the prosthetic valve 120, based on measurement inputs provided by at least two pressure sensing heads 1200. The control unit may include a software for interpreting and/or displaying data. For example, the control unit may provide for multiple measurements to be averaged over several cycles, and/or may provide for cycle-to-cycle variations to be visualized. Thus, an operator of the delivery assembly 100 according to any of the embodiments of the current disclosure, can quickly and easily obtain transvalvular pressure gradients measurement.

According to some embodiments, the pressure sensing heads 1200 can detect pressure variations associated with the change in flow velocity. For example, according to Bernoulli's principle, an increase in the speed of a fluid can occur simultaneously with a decrease in pressure.

According to some embodiments, the control unit is configured to receive signals from at least two pressure sensing heads 1200 oriented at diametrically opposite directions relative to the longitudinal axis 121, representative of the pressure in the vicinity of the membranes of each of the corresponding pressure sensing heads 1200. The control unit can be configured to continuously calculate the pressure difference between the outer and inner prosthetic valve regions, based on measurement signals provided by the at least two diametrically opposing pressure sensing heads 1200.

According to some embodiments, the control unit is configured to receive signals, such as optical signals, from at least one pressure sensing head 750, configured to contact the tissue surrounding the prosthetic valve 120 during valve expansion, representative of the radial force applied by the surrounding tissue on the sensor, responsive to the valve's expansion. The control unit can be configured to continuously calculate the radial force exerted by the prosthetic valve 120 on the surrounding tissue as it expands, based on measurement inputs provided by at least one pressure sensing head or contact force sensing head 750 when in contact with the surrounding tissue.

According to some embodiments, optic fibers according to any of the embodiments of the current disclosure are operatively coupled to a digital display 116 or led lights 118. According to some embodiments, optic fibers are operatively coupled to the digital display 116 or led lights 118 via the control unit. The digital display 116 may comprise a digital screen, which may present numerical values indicative of the prosthetic valve's 120 current diameter, the strain measured on the valve 120, the pressure drop across the prosthetic valve 120, the pressure difference between regions radially outside of and inside of the valve's frame 126, flow velocity derived from pressure variation measurements, the force exerted by the valve 120 on the surrounding tissue, and/or the reactive force exerted by the surrounding tissue, responsive to the valve's expansion. The digital display 116 may similarly display other icons, textual messages and/or graphical symbols. Additionally or alternatively, led lights 118, lamps or other visual elements, can be configured to provide the user with a visual indication regarding the above mentioned parameters. According to some embodiments, the control unit is configured to display the above mentioned parameters on the digital display 116 in real-time as the prosthetic valve 120 is expanded and/or compressed during an implantation procedure.

According to some embodiments, the control unit further comprises a memory member, and selected data, such as raw signal data or calculated data, can be stored in the memory member. A memory member may include a suitable memory chip or storage medium such as, for example, a PROM, EPROM, EEPROM, ROM, flash memory, solid state memory, or the like. A memory member can be integral with the control unit or may be removably coupled to the control unit. According to some embodiments, the control unit is configured to log data during the implantation procedure in the memory member. According to some embodiments, the control unit is configured to transmit logged data from the memory member, and/or real-time data, to a remote device.

According to some embodiments, the control unit is configured to provide an alert to an operator in the event that any of the above mentioned parameters exceeds a predefined threshold. For example, an alert may be provided if the prosthetic valve 120 is over-expanded within a native annulus. The alert can be an audible alert, a visual alert, a tactile alert, etc.

According to some embodiments, the control unit can be further configured to control the actuation members 172 to expand the prosthetic valve 120 according to pre-programmed expansion algorithms.

According to some embodiments, the control unit and or the digital display 116 can be formed separately from the delivery apparatus 102 and operatively connected thereto, for example using wires or cables. According to additional embodiments, the control unit and/or the digital display 116 can be formed integrally with the handle 110. For example, a processor and other electrical components of a control unit can be located within the handle 110, and the digital display 116 can be located on an exterior surface of the handle 110, as shown in FIG. 1, such that it can be viewed by a clinician during the implantation procedure.

It is appreciated that certain features, which are, for clarity, described in the context of separate embodiments, may also be provided in combination in a single embodiment. Conversely, various features, which are, for brevity, described in the context of a single embodiment, may also be provided separately or in any suitable sub-combination or as suitable in any other described embodiment described herein. No feature described in the context of an embodiment is to be considered an essential feature of that embodiment, unless explicitly specified as such.

Although specific embodiments are described herein, numerous alternatives, modifications and variations that are apparent to those skilled in the art may exist. It is to be understood that the embodiments described herein are not necessarily limited in their applications to the details of construction and the arrangement of the components and/or methods set forth herein. Other embodiments may be practiced, and an embodiment may be carried out in various ways. Accordingly, the embodiments described herein embrace all such alternatives, modifications and variations that fall within the scope of the appended claims.

The invention claimed is:

1. A delivery assembly comprising:
a prosthetic valve radially expandable and compressible between a radially compressed state and a radially expanded state, the prosthetic valve comprising an outflow end portion, an inflow end portion, and at least one actuator assembly, each actuator assembly comprising:
an outer member defined between an outer member proximal end and an outer member distal end, the outer member being secured to a first location of the valve; and
an inner member secured to a second location of the valve, axially spaced from the first location;
a delivery apparatus comprising a handle and at least one actuation arm assembly extending from the handle, the at least one actuation arm assembly comprising:
an actuation member releasably coupled to the inner member; and
a support sleeve surrounding the actuation member;
at least one optic fiber assembly comprising:
a first optic fiber section, connected to the delivery apparatus, the first optic fiber section comprising at least one first optic core;
a second optic fiber section, connected to the prosthetic valve, the second optic fiber section comprising at least one second optic core; and
an interface between the first optic fiber section and the second optic fiber section,
wherein the interface is configured to provide detachable optical coupling between the first optic fiber section and the second optic fiber section;
wherein the prosthetic valve is expandable from the radially compressed state to the radially expanded state upon actuating the at least one actuator assembly to approximate the second location to the first location;
wherein the prosthetic valve is releasable from the delivery apparatus by decoupling each of the at least one actuation arm assemblies from each corresponding actuator assembly; and
wherein the second optic fiber section is configured to be decoupled from the first optic fiber section, upon releasing the prosthetic valve from the delivery apparatus.

2. The delivery assembly of claim 1, wherein the at least one second optic fiber section comprises a plurality of axially spaced Fiber Bragg Gratings disposed along at least a portion of its second optic core.

3. The delivery assembly of claim 1, wherein the second optic fiber section comprises at least one pressure sensing head.

4. The delivery assembly of claim 3, wherein the at least one pressure sensing head is an axial pressure sensing head comprising: a front diaphragm, and a front cavity between the at least one second optic core and the front diaphragm, wherein both of the front diaphragm and the front cavity are coaxially aligned with the at least one second optic core.

5. The delivery assembly of claim 3, wherein the at least one second optic core comprises an inclined distal core surface, wherein the at least one pressure sensing head is a lateral pressure sensing head comprising: a side diaphragm, and a side cavity between the inclined distal core surface and the side diaphragm, and wherein both of the side diaphragm and the side cavity are cross-axially aligned with the at least one second optic core.

6. The delivery assembly of claim 3, wherein the at least one optic fiber assembly is a multi-core optic fiber assembly comprising a plurality of axially spaced pressure sensing heads, wherein the first optic fiber section comprises a plurality of first optic cores.

7. The delivery assembly of claim 6, wherein the second optic fiber section comprises a plurality of cores and a plurality of axially spaced pressure sensing heads, wherein at least one of the plurality of pressure sensing heads is positioned in the outflow end portion of the prosthetic valve, and wherein at least another one of the plurality of pressure sensing heads is positioned in the inflow end portion of the prosthetic valve.

8. The delivery assembly of claim 6, wherein the first optic fiber section comprises at least two cores and at least one pressure sensing head, and wherein the second optic fiber section comprises at least one pressure sensor head.

9. The delivery assembly of claim 5, wherein the at least one lateral pressure sensing head is a contact-force sensing head, further comprising a lateral extension.

10. The delivery assembly of claim 5, comprising at least two optic fiber assemblies attached to the same actuator assembly, wherein each optic fiber assembly comprises a lateral pressure sensing head, such that the at least two lateral pressure sensing heads are oriented at diametrically opposing radial directions.

11. The delivery assembly of claim 5, wherein the at least one optic fiber assembly is a multi-core optic fiber assembly comprising at least two lateral pressure sensing heads attached to the same actuator assembly and oriented at diametrically opposing radial directions.

12. The delivery assembly of claim 1, wherein the actuation member comprises an actuation member channel, and wherein at least a portion of the at least one first optic fiber section extends through the actuation member channel.

13. The delivery assembly of claim 1, wherein the inner member comprises an inner member channel, and wherein at least a portion of the at least one second optic fiber section extends through the inner member channel.

14. The delivery assembly of claim 1, further comprising at least one continuous optic fiber connected to the delivery apparatus, the at least one continuous optic fiber comprising at least one continuous optic core and at least one pressure sensing head.

15. The delivery assembly of claim 3, wherein the at least one optic fiber assembly comprises a plurality optic fiber assemblies, positioned such that the respective pressure sensing heads are circumferentially distanced from each other around the prosthetic valve.

16. The delivery assembly of claim 15, wherein the pressure sensing heads are positioned at the outflow end portion.

* * * * *